US011827883B2

(12) United States Patent
Kasperkovitz et al.

(10) Patent No.: US 11,827,883 B2
(45) Date of Patent: *Nov. 28, 2023

(54) DOSAGES AND METHODS FOR DELIVERING LIPID FORMULATED NUCLEIC ACID MOLECULES

(71) Applicant: Alnylam Pharmaceuticals, Inc., Cambridge, MA (US)

(72) Inventors: Pia Kasperkovitz, Cambridge, MA (US); Jared Gollob, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 40 days.

This patent is subject to a terminal disclaimer.

(21) Appl. No.: 17/225,943

(22) Filed: Apr. 8, 2021

(65) Prior Publication Data

US 2021/0388355 A1 Dec. 16, 2021

Related U.S. Application Data

(62) Division of application No. 16/261,181, filed on Jan. 29, 2019, now abandoned, which is a division of application No. 14/889,352, filed as application No. PCT/US2014/036915 on May 6, 2014, now Pat. No. 10,246,708.

(60) Provisional application No. 61/820,036, filed on May 6, 2013.

(51) Int. Cl.
| | | |
|---|---|---|
| *C12N 15/113* | (2010.01) | |
| *A61M 5/315* | (2006.01) | |
| *A61K 9/127* | (2006.01) | |
| *A61K 47/60* | (2017.01) | |
| *A61K 47/54* | (2017.01) | |
| *A61K 9/00* | (2006.01) | |
| *A61K 9/51* | (2006.01) | |

(52) U.S. Cl.
CPC .......... *C12N 15/113* (2013.01); *A61K 9/0019* (2013.01); *A61K 9/1271* (2013.01); *A61K 9/1272* (2013.01); *A61K 9/5123* (2013.01); *A61K 9/5146* (2013.01); *A61K 47/543* (2017.08); *A61K 47/60* (2017.08); *A61M 5/31533* (2013.01); *C12N 2310/11* (2013.01); *C12N 2310/14* (2013.01); *C12N 2310/315* (2013.01); *C12N 2310/321* (2013.01); *C12N 2310/322* (2013.01); *C12N 2310/335* (2013.01); *C12N 2310/3515* (2013.01); *C12N 2320/32* (2013.01); *C12N 2320/35* (2013.01); *C12N 2320/53* (2013.01)

(58) Field of Classification Search
None
See application file for complete search history.

(56) References Cited

U.S. PATENT DOCUMENTS

| 2011/0034537 A1 | 2/2011 | De Fougerolles et al. |
| 2013/0289094 A1 | 10/2013 | Hinkle et al. |
| 2017/0307608 A1 | 10/2017 | Bettencourt |

FOREIGN PATENT DOCUMENTS

| WO | 2010083615 A1 | 7/2010 |
| WO | 2012058693 A2 | 5/2012 |
| WO | 2014182661 A2 | 11/2014 |
| WO | 2016033326 A2 | 3/2016 |

OTHER PUBLICATIONS

U.S. Appl. No. 14/889,352 U.S. Pat. No. 10,246,708, filed Nov. 5, 2015 Apr. 2, 2019, US 20160122759, Granted.
U.S. Appl. No. 16/261,181, filed Jan. 29, 2019, US 20190284557, Abandoned.
European Search Report for European Application No. 14795153.7 dated Sep. 12, 2016.
International Search Report and Written Opinion for International Application No. PCT/US2014/036915 dated Nov. 18, 2014.
Suhr et al. "Efficacy and safety of partisiran for familial amyloidotic polyneuropathy: a phase II multi-dose study" Orphanet Journal of Rare Diseases (2015) vol. 10, No. 109, pp. 1-9.
Szebeni et al. "Hemodynamic Changes Induced by Liposomes and Liposome-Encapsulated Hemoglobin in Pigs" Circulation (1999) vol. 99, pp. 2302-2309.
Szebeni, "Hemocompatibility testing for nanomedicines and biologicals: predictive assays for complement mediated Infusion reactions" European Journal of Nanomedicine (2012) vol. 4, No. 1, pp. 33-53.

*Primary Examiner* — Sean McGarry
(74) *Attorney, Agent, or Firm* — McCarter & English, LLP; Maria Laccotripe Zacharakis; Deborah L. Nagle

(57) ABSTRACT

Methods, kits and devices for dosing a subject to reduce a hypersensitivy response to a lipid-formulated nucleic acid (e.g., RNA) molecule are disclosed.

40 Claims, 5 Drawing Sheets

Specification includes a Sequence Listing.

DOSAGES AND METHODS FOR DELIVERING LIPID FORMULATED NUCLEIC ACID MOLECULES

CROSS-REFERENCE TO RELATED APPLICATIONS

This application is a divisional of U.S. application Ser. No. 16/261,181, filed Jan. 29, 2019, now abandoned, which is a divisional of U.S. application Ser. No. 14/889,352, filed Nov. 5, 2015, now U.S. Pat. No. 10,246,708, which is a U.S. National Phase Application under 35 U.S.C. § 371 of International Application No. PCT/US2014/036915, filed May 6, 2014, which claims the benefit of U.S. Provisional Application No. 61/820,036, filed May 6, 2013. The contents of the aforesaid applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on May 2, 2014, is named Sequence_Listing.txt and is 1,785 bytes in size.

BACKGROUND OF THE INVENTION

Infusion-related reactions (IRRs) relate to any signs or symptoms experienced by a subject during infusion of a pharmacological or biological agent (e.g., a drug). These reactions can be acute, and typically occur during the first hour(s) or day after drug administration. Acute infusion-related reactions include a variety of signs and symptoms, including, but not limited to, neurologic (e.g., dizziness, headache, weakness, syncope, seizure), psychiatric (e.g., anxiety), cardiovascular (e.g., tachycardia, hypotension, arrhythmia, chest pain, ischemia or infarction, cardiac arrest), cutaneous (e.g., flushing, erythema, pruritus, urticaria, angioedema, maculopapular rash), and gastrointestinal signs and symptoms. Manifestations of IRRs can vary, and can include hypersensitivity reactions.

Drug hypersensitivity often results from interactions between a pharmacologic agent and the immune system. Identifiable risk factors for drug hypersensitivity reactions include age, female gender, concurrent illnesses, and previous hypersensitivity to related drugs. Drug hypersensitivity reactions can be classified into immune mediated and non-immune mediated hypersensitivity reactions. Immune mediated hypersensitivity reactions are typically associated with specific, adaptive immune responses generated against an antigen, e.g., a drug. These reactions can occur in a sensitized patient, and can be classified into the following types: Type 1 or immediate IgE-mediated response; Type 2 or antibody dependent cytotoxicity; Type 3 or Immune complex mediated; and Type 4 or delayed response (T cell-mediated) (reviewed in "Drug Hypersensitivity Reactions: Risk Assessment and Management, Society for Toxicology Course" (2011)). Non-immune mediated hypersensitivity reactions relate to drug responses initiated by some pharmacological action of the drug; these reactions can involve immune system components.

Non-immune mediated hypersensitivity reactions, also known as pseudoallergic or anaphylactoid reactions, have clinical manifestations that are often indistinguishable from allergic reactions. These reactions are believed to be associated with complement activation, as well as degranulation of mast cells and/or basophils, which in turn causes histamine release and an anaphylactic-like reaction. Non-immune mediated hypersensitivity reactions are not believed to be triggered via IgE and Fc epsilon receptor activation, and no-presensitization is necessary for a response to occur.

Thus, the need exists for developing novel methods and compositions that reduce hypersensitivity reactions to drugs.

SUMMARY OF THE INVENTION

Disclosed herein are methods, kits and devices for dosing a subject to reduce an infusion-related reaction (IRR) and/or a hypersensitivy reaction (e.g., to reduce the incidence and/or severity of an IRR or a hypersensitivity reaction) to a lipid-formulated nucleic acid (e.g., RNA, e.g., a siRNA) molecule. Without wishing to be bound by theory, Applicants have discovered that infusion reactions to compositions that include a lipid formulation and a nucleic acid (e.g., RNA, e.g., a siRNA) molecule tend to be associated with an IRR and/or hypersensitivity reactions, for example, non-immune mediated hypersensitivity reactions (also referred to herein as pseudoallergic reactions). In one embodiment, administration of a first dose (or a pre-dose) of a lipid-formulated RNA molecule corresponding to a portion of a second dose or the total dose, or administration of a first dose at a portion of the rate of infusion of a second dose, over a pre-treatment interval, was found to reduce or prevent the IRR or the hypersensitivity reaction in a subject. Thus, methods, kits and devices for dosing a subject to reduce an IRR or a hypersensitivy reaction to a lipid-formulated nucleic acid molecule are disclosed.

Accordingly, in one aspect, the invention features a method of reducing an infusion-related reaction, or a hypersensitivity reaction, or both, in a subject, to a composition comprising a lipid formulation and a nucleic acid molecule (e.g., an RNA molecule capable of mediating RNA interference). The method includes administering to a subject a first dose and a second dose of said composition. In certain embodiments, the method includes one, two, three, four, five, six, seven or all of a)-h) of the following:

a) the amount of said composition administered in said first dose is no more than 1/X, wherein X is 3, 4, 5, 6, 7, 8, 9, 10, 15, 20, 30, 40 or 50, of the amount of said composition administered in said second dose;

b) the amount of said composition administered in said first dose is no more than 1/X, wherein X is 2, 3, 4, 5, 6, 7, 8, 9, 10, 15, 20, 30, 40 or 50, of the total amount of said composition administered;

c) the first dose is administered over a time period that is no more than 1/X, wherein X is 2, 3, 4, 5, 6, 7, 8, 9 or 10, of the time period over which the second dose is administered;

d) the first dose is administered over a time period that is no more than 1/X, wherein X is 2, 3, 4, 5, 6, 7, 8, 9 or 10, of the time period over which the total dose is administered;

e) the rate of administration, e.g., in mg/min or mL/min, of said first dose is no more than 1/X, wherein X is 2, 3, 4, 5, 6, 7, 8, 9, 10, 15, 20, 30, 40 or 50, of the rate of administration of said second dose, or the rate of administration of the total dose;

f) the amount of said composition administered in said first dose is no more than 1, 2, 5, 10, 20, 30, 40, 50, 60, 70, 80, 90, or 100 µg nucleic acids per kg body weight, and the second dose is greater than said first dose;

g) the amount of said composition administered in said second dose is greater than 25, 50, 100, 200, 300, 400, 500, 600, 700, 800, 900, or 1000 µg nucleic acids per kg body weight, and the second dose is greater than said first dose; or h) the dosages and time periods of administration of said first and second doses are selected such that no substantial IRR and/or hypersensitivity reaction occurs in said subject.

In some embodiments, the method includes one, two, three, four, five, six, seven or all of a)-h) of the following:

a) the amount of said composition administered in said first dose is no more than 1/X, wherein X is 9, 10 or 15, e.g., 10, of the amount of said composition administered in said second dose;

b) the amount of said composition administered in said first dose is no more than 1/X, wherein X is 9, 10 or 15, e.g., 10, of the total amount of said composition administered;

c) the first dose is administered over a time period that is no more than 1/X, wherein X is 2, 3 or 4, e.g., 3, of the time period over which the second dose is administered;

d) the first dose is administered over a time period that is no more than 1/X, wherein X is 3, 4 or 5, e.g., 4, of the time period over which the total dose is administered;

e) the rate of administration, e.g., in mg/min or mL/min, of said first dose is no more than 1/X, wherein X is 2, 3 or 4, e.g., 3, of the rate of administration of said second dose, or the rate of administration of the total dose;

f) the amount of said composition administered in said first dose is no more than 20, 30 or 40 µg, e.g., 30 µg, nucleic acids per kg body weight, and the second dose is greater than said first dose;

g) the amount of said composition administered in said second dose is greater than 100, 200 or 300 µg, e.g., 200 µg, nucleic acids per kg body weight, and the second dose is greater than said first dose; or h) the dosages and time periods of administration of said first and second doses are selected such that no substantial IRR and/or hypersensitivity reaction occurs in said subject.

In another aspect, the invention features a method of reducing the expression of a target gene, or treating a disorder related to the target gene, in a subject. The method includes administering to the subject a first dose and a second dose of a composition, said composition comprising a lipid formulation and a nucleic acid molecule (e.g., an RNA molecule capable of mediating RNA interference), wherein said first and second doses are administered in an amount sufficient to reduce expression of the target gene, or treat the disorder, in the subject. In certain embodiments, the method includes one, two, three, four, five, six or all of a)-g) of the following:

a) the amount of said composition administered in said first dose is no more than 1/X, wherein X is 3, 4, 5, 6, 7, 8, 9, 10, 15, 20, 30, 40 or 50, of the amount of said composition administered in said second dose;

b) the amount of said composition administered in said first dose is no more than 1/X, wherein X is 2, 3, 4, 5, 6, 7, 8, 9, 10, 15, 20, 30, 40 or 50, of the total amount of said composition administered;

c) the first dose is administered over a time period that is no more than 1/X, wherein X is 2, 3, 4, 5, 6, 7, 8, 9 or 10, of the time period over which the second dose is administered;

d) the first dose is administered over a time period that is no more than 1/X, wherein X is 2, 3, 4, 5, 6, 7, 8, 9 or 10, of the time period over which the total dose is administered;

e) the rate of administration, e.g., in mg/min or mL/min, of said first dose is no more than 1/X, wherein X is 2, 3, 4, 5, 6, 7, 8, 9, 10, 15, 20, 30, 40 or 50, of the rate of administration of said second dose, or the total dose;

f) the amount of said composition administered in said first dose is no more than 1, 2, 5, 10, 20, 30, 40, 50, 60, 70, 80, 90, or 100 µg nucleic acids per kg body weight and said first dose is less than said second dose; or g) the amount of said composition administered in said second dose is greater than 25, 50, 100, 200, 300, 400, 500, 600, 700, 800, 900, or 1000 µg nucleic acids per kg body weight, and said second dose is greater than said first dose.

In some embodiments, the method includes one, two, three, four, five, six or all of a)-g) of the following:

a) the amount of said composition administered in said first dose is no more than 1/X, wherein X is 9, 10 or 15, e.g., 10, of the amount of said composition administered in said second dose;

b) the amount of said composition administered in said first dose is no more than 1/X, wherein X is 9, 10 or 15, e.g., 10, of the total amount of said composition administered;

c) the first dose is administered over a time period that is no more than 1/X, wherein X is 2, 3 or 4, e.g., 3, of the time period over which the second dose is administered;

d) the first dose is administered over a time period that is no more than 1/X, wherein X is 3, 4 or 5, e.g., 4, of the time period over which the total dose is administered;

e) the rate of administration, e.g., in mg/min or mL/min, of said first dose is no more than 1/X, wherein X is 2, 3 or 4, e.g., 3, of the rate of administration of said second dose, or the rate of administration of the total dose;

f) the amount of said composition administered in said first dose is no more than 20, 30 or 40 µg, e.g., 30 µg, nucleic acids per kg body weight, and the second dose is greater than said first dose; or g) the amount of said composition administered in said second dose is greater than 100, 200 or 300 µg, e.g., 200 µg, nucleic acids per kg body weight, and the second dose is greater than said first dose.

Exemplary Determination of First and Second Doses and Rates of Administration

The amount, dose and rate of administration can be calculated based on the lipid content of the composition (also referred to herein as the "lipid" amount, dose or dose rate; or based on the RNA molecule content of the composition (referred to herein as "RNA," "iRNA" or "siRNA" amount, dose or dose rate).

In one embodiment, in the microdosing regimen, 1/X of the total dose D (µg/kg) is administered over a first time period $T_1$ (min) and (X−1)/X of the same total dose is administered over a second time period $T_2$ (min) in a subject having a body weight of W (kg). Accordingly, the first dose is administered at a dose rate of $D/X/T_1$ (µg/kg/min) (or $W*D/X/T_1$ (µg/min)) and the second dose is administered at a dose rate of $D/T_2-D/X/T_2$ (µg/kg/min) (or $W*(D/T_2-D/X/T_2)$ (µg/min)). In one exemplary embodiment, the first and second dose rates are obtained as follows: By administering a first dose (e.g., microdosing) of $1/10^{th}$ of the total dose over a first time interval (e.g., 15 minutes), followed by a second dose of 9/10$^{th}$ of total dose over a second time interval (e.g., 60 minutes), in a subject having a body weight of 80 kg. For example, for the first dose rate, 1/10 of the total siRNA dose 300 µg/kg (i.e., 30 µg/kg) is administered over a first time period of 15 minutes, thus resulting in a first dose rate of 2 µg/kg/min (or 160 µg/min) (iRNA dose rate). The remaining dose or second dose ((10-1)/10=9/10 of the total iRNA dose of 300 µg/kg=270 µg/kg) is administered over 60 min, thus resulting in a second dose rate of 4.5 µg/kg/min (or 360 µg/min). In order to calculate a lipid dose rate, we assumed a total lipid/siRNA ratio of 12.23:1 (wt/wt) for conversion. In such embodiments, the first dose is administered at a lipid dose rate of about 24 µg/kg/min (or 1920 µg/min) (or at an iRNA dose rate of about 2 µg/kg/min) over a period of about 15 minutes, and the second dose is administered at a lipid dose rate of about 55 µg/kg/min (or 4400 µg/min) (or at an siRNA dose rate of about 4.5 µg/kg/min) over a period of about 60 minutes.

Values for first and second dose rates can be obtained for other total doses applying the criteria set for above. In one embodiment, the first and second doses are obtained from a composition formulated as an LNP formulation (e.g., an LNP11 formulation as described herein), which is administered at a total dose range of about 0.05 to about 5 mg/kg (e.g., 10, 50, 150 and 300 microgram/kg) of iRNA. The range of total lipid/iRNA ratios is from about 5 to about 30, e.g., about 8 to about 20, or about 10 to about 15.

Applying the same approach to other doses (e.g., 10, 50, and 150 microgram/kg) of iRNA, the following values for first and second dose rates are obtained: 0.07 µg/kg/min (first iRNA dose rate) and 0.15 µg/kg/min (second iRNA dose rate) for 10 µg/kg dose of iRNA, 0.33 µg/kg/min (first iRNA dose rate) and 0.75 µg/kg/min (second iRNA dose rate) for 50 µg/kg dose of iRNA, 1 µg/kg/min (first iRNA dose rate) and 2 µg/kg/min (second iRNA dose rate) for 150 µg/kg dose of iRNA. The dose rates described above can be converted to µg/min based on the body weight of the subject using the calculation methods described herein.

Alternatively, or in combination with the exemplary embodiment above, microdosing at 1/10$^{th}$ of the non-microdosing infusion rate (e.g., 1/10$^{th}$ of the 60 min infusion rate for 15 min (first dose) followed by the remainder of the dose at the non-microdosing 60 min infusion rate (second dose, total dosing time depends on the weight of the subject).

For example, in the non-microdosing regimen, a total dose of D (µg/kg) is administered at a dose rate R (µg/kg/min) over a total time period of T (min). Accordingly, R=D/T. In the corresponding microdosing regimen, the first dose is administered at 1/X of the dose rate R (µg/kg/min) over a first time period T$_1$ (min) and the remaining dose is administered at the dose rate R over a second time period T$_2$ (min). Accordingly, T$_2$=T-T$_1$/X. For example, in the non-microdosing regimen, a total siRNA dose of 300 (µg/kg) is administered at an iRNA dose rate of 300/60=5 µg/kg/min over a total time period of 60 minutes. In the corresponding microdosing regimen, the first dose is administered at 1/10 of the iRNA dose rate 5 µg/kg/min=0.5 µg/kg/min over a first time period 15 minutes and the remaining dose is administered at the siRNA dose rate of 5 µg/kg/min over a second time period 60-15/10=58.5 minutes. In this exemplary calculation, the total lipid/siRNA ratio of 12.23 (wt/wt) is used for conversion. In such embodiments, the first dose is administered at a lipid dose rate of about 6.1 µg/kg/min (or at an iRNA dose rate of about 0.5 µg/kg/min) over a period of about 15 minutes, and the second dose is administered at a lipid dose rate of about 61 µg/kg/min (or at an iRNA dose rate of about 5 µg/kg/min) over a period of about 60 minutes.

Values for first and second dose rates can be obtained for other total doses applying the criteria set for above. In one embodiment, the first and second doses are obtained from a composition formulated as an LNP formulation (e.g., an LNP11 formulation as described herein), which is administered at a total dose range of about 0.05 to about 5 mg/kg (e.g., 10, 50, 150 and 300 microgram/kg) of iRNA. The range of total lipid/iRNA ratios is from about 5 to about 30, e.g., about 8 to about 20, or about 10 to about 15.

Applying the same approach to other doses (e.g., 10, 50, and 150 microgram/kg) of iRNA, the following values for first and second dose rates are obtained: 0.017 µg/kg/min (first iRNA dose rate) and 0.17 µg/kg/min (second iRNA dose rate) for 10 µg/kg dose of iRNA, 0.083 µg/kg/min (first iRNA dose rate) and 0.83 µg/kg/min (second iRNA dose rate) for 50 µg/kg dose of iRNA, 0.25 µg/kg/min (first iRNA dose rate) and 2.5 µg/kg/min (second iRNA dose rate) for 150 µg/kg dose of iRNA. The dose rates described above can be converted to µg/min based on the body weight of the subject using the calculation methods described herein.

As another example, in the non-microdosing regimen, a total dose of D (µg/kg) is administered at a dose rate R (µg/min) over a total time period of T (min) in a subject having a body weight of W (kg). In the corresponding microdosing regimen, the first dose is administered at 1/X of the dose rate R (µg/min) over a first time period T$_1$ (min) and the remaining dose (W*D-T$_1$*R/X (µg)) is administered at the dose rate R over a second time period T$_2$ (min). Accordingly, T$_2$=W*D/R-T$_1$/X. For example, in the non-microdosing regimen, a total siRNA dose of 300 (µg/kg) is administered at an iRNA dose rate of 400 µg/min over a total time period of 60 minutes in a subject having a body weight of 80 kg. In the corresponding microdosing regimen, the first dose is administered at 1/10 of the iRNA dose rate 400 µg/min=40 µg/min over a first time period 15 minutes and the remaining dose (80 (kg)×300 (µg/kg)-40 (µg/min)×15 (min)=23400 µg) is administered at the siRNA dose rate of 400 µg/min over a second time period 23400 (µg)/400 (µg/min)=58.5 min. The total lipid/siRNA ratio of 12.23 (wt/wt) is used for conversion. In such embodiments, the first dose is administered at a lipid dose rate of about 489.2 µg/min (or at an iRNA dose rate of about 40 µg/min) over a period of about 15 minutes, and the second dose is administered at a lipid dose rate of about 4892 µg/min (or at an iRNA dose rate of about 40 µg/min) over a period of about 60 minutes.

Values for first and second dose rates can be obtained for other total doses applying the criteria set for above. In one embodiment, the first and second doses are obtained from a composition formulated as an LNP formulation (e.g., an LNP11 formulation as described herein), which is administered at a total dose range of about 0.05 to about 5 mg/kg (e.g., 10, 50, 150 and 300 microgram/kg) of iRNA. The range of total lipid/iRNA ratios is from about 5 to about 30, e.g., about 8 to about 20, or about 10 to about 15.

Applying the same approach to other doses (e.g., 10, 50, and 150 microgram/kg) of iRNA, the following values for first and second dose rates are obtained for a subject having a body weight of 80 kg: 1.3 µg/min (first iRNA dose rate) and 13.3 µg/min (second iRNA dose rate) for 10 µg/kg dose of iRNA, 6.7 µg/min (first iRNA dose rate) and 66.7 µg/min (second iRNA dose rate) for 50 µg/kg dose of iRNA, 20 µg/min (first iRNA dose rate) and 200 µg/min (second iRNA dose rate) for 150 µg/kg dose of iRNA.

As yet another example, in the non-microdosing regimen, a total dose of 0.30 mg/kg of iRNA is administered at 3 mL/min over a period of 60 minutes. In the corresponding microdosing regimen administered over a period of 70 minutes, a first dose is administered at 1 mL/min over a period of 15 minutes and a second dose is administered at 3 mL/min over a period of 55 minutes (a total dose of 0.30 mg/kg of iRNA in 180 mL).

The following values for the first and second iRNA dose rates are obtained for a subject: 1.67 µg/kg/min (first iRNA dose rate) and 5 µg/kg/min (second iRNA dose rate). The following values for the first and second lipid dose rates (lipid:siRNA ratio=11.6:1) are obtained for a subject: 19.4 µg/kg/min (first lipid dose rate) and 58 µg/kg/min (second lipid dose rate).

Based on the time intervals for administration, the following values for the first and second iRNA doses are obtained for a subject: 25 µg/kg (first iRNA dose) and 275 µg/kg (second iRNA dose). Based on the time intervals for administration, the following values for the first and second lipid doses (lipid:siRNA ratio=11.6:1) are obtained for a subject: 290 µg/kg (first lipid dose) and 3190 µg/kg (second lipid dose).

The dose rates and doses described above can be converted to mg/min based on the body weight of the subject.

The following values for the first and second iRNA dose rates are obtained for a subject having a body weight of 70 kg: 0.117 mg/min (first iRNA dose rate) and 0.35 mg/min (second iRNA dose rate). The following values for the first and second lipid dose rates (lipid:siRNA ratio=11.6:1) are obtained for a subject having a body weight of 70 kg: 1.36 mg/min (first lipid dose rate) and 4.06 mg/min (second lipid dose rate).

Based on the time intervals for administration, the following values for the first and second iRNA doses are obtained for a subject having a body weight of 70 kg: 1.75 mg (first iRNA dose) and 19.25 mg (second iRNA dose). Based on the time intervals for administration, the following values for the first and second lipid doses (lipid:siRNA ratio=11.6:1) are obtained for a subject having a body weight of 70 kg: 20.3 mg (first lipid dose) and 223.3 mg (second lipid dose).

The same approach can be applied to any other total doses (e.g., 0.01, 0.05, or 0.15 mg/kg) of iRNA, lipid:siRNA ratios (e.g., between 11.5 to 14.1), body weight, and/or intervals for administration, e.g., as described herein.

Other features and embodiments of the invention are described as follows:

Doses

In certain embodiments, the amount of said composition administered in said first dose is chosen from between (and including): about 1% to about 25%, about 3% and about 20%, about 5% and about 15%, or about 8% and about 12% (e.g., about 9-10%), of the total amount of said composition, or the amount of the composition administered in said second dose.

In one embodiment, the amount of lipid formulation administered in said first dose is chosen from about 5 µg/kg to about 3000 µg/kg, about 50 µg/kg to about 2000 µg/kg, about 100 µg/kg to about 1500 µg/kg, about 200 µg/kg to about 1000 µg/kg, or about 300 µg/kg to about 500 µg/kg.

Alternatively, or in combination with, the first dose values described herein, the amount of lipid formulation administered in said second dose is chosen about 125 µg/kg to about 15000 µg/kg, about 500 µg/kg to about 10000 µg/kg, about 1000 µg/kg to about 7500 µg/kg, about 2000 µg/kg to about 5000 µg/kg, or about 3000 µg/kg to about 4000 µg/kg.

In yet other embodiments, the amount of the nucleic acid (e.g., RNA) molecule in said first dose is chosen from about 0.1 µg/kg to about 100 µg/kg, about 0.5 µg/kg to about 75 µg/kg, about 1 µg/kg to about 50 µg/kg, about 2 µg/kg to about 30 µg/kg, about 5 µg/kg to about 15 µg/kg.

Alternatively, or in combination with, the first dose values described herein, the amount of the RNA molecule in said second dose is chosen from about 5 µg/kg to about 1000 µg/kg, about 25 µg/kg to about 800 µg/kg, about 50 µg/kg to about 600 µg/kg, about 100 µg/kg to about 400 µg/kg, or about 200 µg/kg to about 300 µg/kg.

In some embodiments, the total amount of the RNA molecule in said first dose and said second dose is chosen from about 100 µg/kg to about 500 µg/kg, or about 200 µg/kg to about 400 µg/kg, e.g., about 300 µg/kg.

In some embodiments, the body weight of the subject is chosen from about 50 kg to about 150 kg, from about 50 kg to about 104 kg, from about 60 kg to about 100 kg, from about 70 kg to about 90 kg, e.g., about 80 kg.

It shall be understood that the values provided herein for the dose ranges for the first and second doses based on the composition, lipid formulation and/or RNA molecules can be combined in any order in the methods, kits and devices described herein. In certain embodiments, any of the aforesaid values for the dose ranges can be combined with the administration rates and time intervals for administration described herein.

Dose Rates

In other embodiments, the rate of administration, e.g., in mg/min or mL/min, of said first dose is no more than 1/X, wherein X is 3, 4, 5, 6, 7, 8, 9, 10, 15, 20, 30, 40 or 50, of the rate of administration of said second dose, or the rate of administration of the total dose. In one embodiment, the rate of administration, e.g., in mg/min or mL/min, of said first dose is chosen from one or more of: about 5% to 50%, about 5% to about 20%, about 5% to 10%, about 8% to 45%, about 10% and 40%, about 10% to about 20%, or about 10% and 35%, or about 20% to about 40% (e.g., about 10-33%) of the rate of administration of the second dose, or the total dose.

In yet other embodiments, the rate of administration of the lipid formulation in said first dose is chosen from about 0.05 µg/min/kg to about 50 µg/min/kg, about 0.1 µg/min/kg to about 25 µg/min/kg, about 1 µg/min/kg to about 15 µg/min/kg, or about 5 µg/min/kg to about 10 µg/min/kg. In yet other embodiments, the rate of administration of the lipid formulation in said first dose is chosen from about 2.5 µg/min to about 5000 µg/min, about 5 µg/min to about 2500 µg/min, about 50 µg/min to about 1500 µg/min, or about 250 µg/min to about 1000 µg/min.

Alternatively, or in combination with, the rate of administration values for the first dose described herein, the rate of administration of the lipid formulation in said second dose is chosen from about 0.5 µg/min/kg to about 500 µg/min/kg, about 1 µg/min/kg to about 250 µg/min/kg, about 10 µg/min/kg to about 150 µg/min/kg, or about 50 µg/min/kg to about 100 µg/min/kg. In yet other embodiments, the rate of administration of the lipid formulation in said second dose is chosen from about 25 µg/min to about 50000 µg/min, about 50 µg/min to about 25000 µg/min, about 500 µg/min to about 15000 µg/min, or about 2500 µg/min to about 10000 µg/min.

In yet other embodiments, the rate of administration of the nucleic acid (e.g., RNA) molecule in said first dose is chosen from about 0.01 µg/min/kg to about 5 µg/min/kg, about 0.02 µg/min/kg to about 2.5 µg/min/kg, about 0.05 µg/min/kg to about 1 µg/min/kg, or about 0.1 µg/min/kg to about 0.5 µg/min/kg. In yet other embodiments, the rate of administration of the nucleic acid (e.g., RNA) molecule in said first dose is chosen from about 0.5 µg/min to about 600 µg/min, about 1 µg/min to about 250 µg/min, about 2.5 µg/min to about 100 µg/min, or about 5 µg/min to about 50 µg/min.

Alternatively, or in combination with, the rate of administration values for the first dose described herein, the rate of administration of the nucleic acid (e.g., RNA) molecule in said second dose is chosen from about 0.1 µg/min/kg to about 50 µg/min/kg, about 0.2 µg/min/kg to about 25 µg/min/kg, about 0.5 µg/min/kg to about 10 µg/min/kg, or about 1 µg/min/kg to about 5 µg/min/kg. In yet other embodiments, the rate of administration of the nucleic acid (e.g., RNA) molecule in said second dose is chosen from about 5 µg/min to about 6000 µg/min, about 10 µg/min to about 2500 µg/min, about 25 µg/min to about 1000 µg/min, or about 50 µg/min to about 500 µg/min.

In yet other embodiments, the rate of administration in said first dose is chosen from about 0.5 mL/min to about 2 mL/min, e.g., about 1 mL/min.

Alternatively, or in combination with, the rate of administration values for the first dose described herein, the rate of administration in said second dose is chosen from about 2 mL/min to about 4 mL/min, e.g., about 3 mL/min.

It shall be understood that the values provided herein for the rates of administration for the first and second doses based on the composition, lipid formulation and/or RNA molecules can be combined in any order in the methods, kits and devices described herein. In certain embodiments, any of the aforesaid values for the rates of administration can be combined with the dose ranges and time intervals for administration described herein.

For example, the first and second rate of administration values can be combined as follows:
i) the rate of administration of the lipid formulation in said first dose is chosen from about 0.05 µg/min/kg to about 50 µg/min/kg, about 0.1 µg/min/kg to about 25 µg/min/kg, about 1 µg/min/kg to about 15 µg/min/kg, or about 5 µg/min/kg to about 10 µg/min/kg; and
ii) the rate of administration of the lipid formulation in said second dose is chosen from about 0.5 µg/min/kg to about 500 µg/min/kg, about 1 µg/min/kg to about 250 µg/min/kg, about 10 µg/min/kg to about 150 µg/min/kg, or about 50 µg/min/kg to about 100 µg/min/kg.

As another example, the first and second rate of administration values can be combined as follows:
i) the rate of administration of the lipid formulation in said first dose is chosen from about 2.5 µg/min to about 5000 µg/min, about 5 µg/min to about 2500 µg/min, about 50 µg/min to about 1500 µg/min, or about 250 µg/min to about 1000 µg/min; and
ii) the rate of administration of the lipid formulation in said second dose is chosen from about 25 µg/min to about 50000 µg/min, about 50 µg/min to about 25000 µg/min, about 500 µg/min to about 15000 µg/min, or about 2500 µg/min to about 10000 µg/min.

As yet another example, the first and second rate of administration values can be combined as follows:
i) the rate of administration in said first dose is chosen from about 0.5 mL/min to about 2 mL/min, e.g., about 1 mL/min; and
ii) the rate of administration in said second dose is chosen from about 2 mL/min to about 4 mL/min, e.g., about 3 mL/min.

In yet other embodiments,
i) the rate of administration of the lipid formulation in said first dose is chosen from about 0.05 µg/min/kg to about 50 µg/min/kg, about 0.1 µg/min/kg to about 25 µg/min/kg, about 1 µg/min/kg to about 15 µg/min/kg, or about 5 µg/min/kg to about 10 µg/min/kg; and
ii) the rate of administration of the lipid formulation in said second dose is chosen from about 0.5 µg/min/kg to about 500 µg/min/kg, about 1 µg/min/kg to about 250 µg/min/kg, about 10 µg/min/kg to about 150 µg/min/kg, or about 50 µg/min/kg to about 100 µg/min/kg; and
wherein the first dose is administered over a time period that is no greater than 1/X, wherein X=2, 3, 4, 5, 6, 7, 8, 9 or 10 (e.g., X is 3, 4, or 5, e.g., 4) the time period over which the total dose is administered.

In yet other embodiments,
i) the rate of administration of the lipid formulation in said first dose is chosen from about 2.5 µg/min to about 5000 µg/min, about 5 µg/min to about 2500 µg/min, about 50 µg/min to about 1500 µg/min, or about 250 µg/min to about 1000 µg/min; and
ii) the rate of administration of the lipid formulation in said second dose is chosen from about 25 µg/min to about 50000 µg/min, about 50 µg/min to about 25000 µg/min, about 500 µg/min to about 15000 µg/min, or about 2500 µg/min to about 10000 µg/min.

wherein the first dose is administered over a time period that is no greater than 1/X, wherein X=2, 3, 4, 5, 6, 7, 8, 9 or 10 (e.g., X is 3, 4, or 5, e.g., 4) the time period over which the total dose is administered.

In other embodiments, the first and second rate of administration values can be combined as follows:
(i) the rate of administration of the nucleic acid (e.g., RNA) molecule in said first dose is chosen from about 0.01 µg/min/kg to about 5 µg/min/kg, about 0.02 µg/min/kg to about 2.5 µg/min/kg, about 0.05 µg/min/kg to about 1 µg/min/kg, or about 0.1 µg/min/kg to about 0.5 µg/min/kg; and
(ii) the rate of administration of the nucleic acid (e.g., RNA) molecule in said second dose is chosen from about 0.1 µg/min/kg to about 50 µg/min/kg, about 0.2 µg/min/kg to about 25 µg/min/kg, about 0.5 µg/min/kg to about 10 µg/min/kg, or about 1 µg/min/kg to about 5 µg/min/kg.

In other embodiments, the first and second rate of administration values can be combined as follows:
(i) the rate of administration of the nucleic acid (e.g., RNA) molecule in said first dose is chosen from about 0.5 µg/min to about 600 µg/min, about 1 µg/min to about 250 µg/min, about 2.5 µg/min to about 100 µg/min, or about 5 µg/min to about 50 µg/min; and
(ii) the rate of administration of the nucleic acid (e.g., RNA) molecule in said second dose is chosen from about 5 µg/min to about 6000 µg/min, about 10 µg/min to about 2500 µg/min, about 25 µg/min to about 1000 µg/min, or about 50 µg/min to about 500 µg/min.

In yet other embodiments, the first and second rate of administration values can be combined as follows:
(i) the rate of administration of the nucleic acid (e.g., RNA) molecule in said first dose is chosen from about 0.01 µg/min/kg to about 5 µg/min/kg, about 0.02 µg/min/kg to about 2.5 µg/min/kg, about 0.05 µg/min/kg to about 1 µg/min/kg, or about 0.1 µg/min/kg to about 0.5 µg/min/kg; and
(ii) the rate of administration of the nucleic acid (e.g., RNA) molecule in said second dose is chosen from about 0.1 µg/min/kg to about 50 µg/min/kg, about 0.2 µg/min/kg to about 25 µg/min/kg, about 0.5 µg/min/kg to about 10 µg/min/kg, or about 1 µg/min/kg to about 5 µg/min/kg; and
wherein the first dose is administered over a time period that is no greater than 1/X, wherein X=2, 3, 4, 5, 6, 7, 8, 9 or 10 (e.g., X is 3, 4, or 5, e.g., 4) the time period over which the total dose is administered.

In yet other embodiments, the first and second rate of administration values can be combined as follows:
(i) the rate of administration of the nucleic acid (e.g., RNA) molecule in said first dose is chosen from about 0.5 μg/min to about 600 μg/min, about 1 μg/min to about 250 μg/min, about 2.5 μg/min to about 100 μg/min, or about 5 μg/min to about 50 μg/min; and
(ii) the rate of administration of the nucleic acid (e.g., RNA) molecule in said second dose is chosen from about 5 μg/min to about 6000 μg/min, about 10 μg/min to about 2500 μg/min, about 25 μg/min to about 1000 μg/min, or about 50 μg/min to about 500 μg/min; and
wherein the first dose is administered over a time period that is no greater than 1/X, wherein X=2, 3, 4, 5, 6, 7, 8, 9 or 10 the time period over which the total dose is administered.

In yet other embodiments, the first and second rate of administration values can be combined as follows:
i) the rate of administration in said first dose is chosen from about 0.5 mL/min to about 2 mL/min, e.g., about 1 mL/min; and
ii) the rate of administration in said second dose is chosen from about 2 mL/min to about 4 mL/min, e.g., about 3 mL/min; and
wherein the first dose is administered over a time period that is no greater than 1/X, wherein X=2, 3, 4, 5, 6, 7, 8, 9 or 10 (e.g., X is 3, 4, or 5, e.g., 4) the time period over which the total dose is administered.

Time Interval for Administration

Alternatively, or in combination with, the dose ranges and rates of administration described herein, the first dose is administered over a time period that is no greater than 1/X, wherein X=2, 3, 4, 5, 6, 7, 8, 9 or 10 times the time period over which the total dose is administered.

Alternatively or in combination with time interval for administration of the first dose described herein, the second dose is administered over a time period that is at least 2, 3, 4, 5, 6, 7, 8, 9 or 10 times greater than the time period over which the first dose is administered.

In certain embodiments, the first dose is administered over a time period that is between 5% and 50%, between 10% and 45%, between 15% and 40%, between 20% and 35%, or between 25% and 30% of the time period of administration of the second dose (e.g., about 27% of the second time period).

In other embodiments, the first dose is administered over a time period that is between 5 minutes and 60 minutes, between 10 minutes and 50 minutes, between 20 minutes and 40 minutes, between 5 minutes and 30 minutes, or between 10 minutes and 20 minutes (e.g., about 15 minutes).

Alternatively or in combination with time interval for administration of the first dose described herein, the second dose is administered over a time period that is between 30 minutes and 180 minutes, between 40 minutes and 120 minutes, between 45 minutes and 90 minutes, or between 50 minutes and 65 minutes (e.g., about 55 minutes).

In yet other embodiments, the first and second administration are effected sequentially or substantially sequentially. In one embodiment, no more than 1, 10, 20, 30, 60, or 180 minutes separates the completion of the administration of the first dose and the initiation of the administration of the second dose. In yet other embodiments, the completion of the administration of the first dose and the initiation of the administration of the second dose is essentially simultaneous.

In certain embodiments, the methods described herein further include administering to the subject one or more doses of the composition, e.g., a third, fourth compositions.

Administration

The doses described herein can be administered by any suitable rout of administration, including but not limited to, intravenous, intraarterial, subcutaneous, intraperitoneal or intramuscular injection or infusion. In one embodiment, administration of the first and second doses is effected intravenously, e.g., by infusion (e.g., via a pump). In embodiments, the first and second doses are administered at a substantially constant rate, e.g., via a pump or a sustained or controlled release formulation. In other embodiments, the first and second doses are administered as a gradient or multiple rates (e.g., two or more rates of infusion).

In one embodiment, the flow rate of administration of the first dose is no more than 1/X, wherein X is 2, 3, 4, 5, 6, 7, 8, 9, 10, 15, 20, 30, 40 or 50, of the flow rate of administration of said second dose. For example, the flow rate of administration of the first dose is chosen from about 0.5 to 1.5 mL/min, about 0.8 to 1.3 mL/min, or about 1 to 1.2 mL/min (e.g., 1 mL/min or 1.1 mL/min); alternatively, or in combination, the flow rate of administration of the second dose is chosen from about 2 to 4 mL/min, about 2.5 to 3.7 mL/min, or about 3 to 3.5 mL/min (e.g., 3 mL/min or 3.3 mL/min).

In certain embodiments, the total volume of infusion is about 100 to 300 mL, about 150 to 250 mL, about 180 mL, or about 200 mL.

Methods of preparing the first and second dose as described herein are also disclosed. For example, the methods can include the step of modifying the rate of administration of the composition, such that the dose is adjusted.

In an aspect provided herein, the compositions described are pharmaceutically acceptable, e.g., a pharmaceutical composition. The pharmaceutical compositions can be administered in an unbuffered solution, e.g., saline or water. In other embodiments, the pharmaceutical composition is administered with a buffer solution. In embodiments, the buffer solution comprises acetate, citrate, prolamine, carbonate, or phosphate or any combination thereof. In embodiments, the buffer solution is phosphate buffered saline (PBS).

In embodiments, the composition, e.g., pharmaceutical composition, is administered intravenously.

In embodiments, the composition, e.g., pharmaceutical composition, is administered subcutaneously.

Other features and embodiments of the invention include one or more of the following.

In certain embodiments of the aforesaid methods, the first dose is administered at a first nucleic acid dose rate between 1.5 and 2 μg/kg/min of, and
  the second dose is administered at a second nucleic acid dose rate between 4 and 6 μg/kg/min; and/or
  the first dose is administered at a first lipid dose rate between 15 and 25 μg/kg/min, and
  the second dose is administered at a second lipid dose rate between 55 and 75 μg/kg/min.

In other embodiments of the aforesaid methods, the first dose is administered at a first nucleic acid dose rate between 1.5 and 2 μg/kg/min, and
  the second dose is administered at a second nucleic acid dose rate between 4 and 6 μg/kg/min;

In other embodiments of the aforesaid methods, the first lipid dose rate is between 15 and 25 μg/kg/min, and the second lipid dose rate is between 55 and 75 μg/kg/min.

In other embodiments of the aforesaid methods, the first dose is administered at between 0.5 and 1.5 mL/min, and the second dose is administered at between 2.5 and 3.5 mL/min.

In other embodiments of the aforesaid methods, the first dose is administered over a period of between 10 and 20 minutes, and the second dose is administered over a period of between 50 and 60 minutes.

In other embodiments of the aforesaid methods, the first nucleic acid dose is between 20 and 30 µg/kg, and the second nucleic acid dose is between 250 and 300 µg/kg.

In other embodiments of the aforesaid methods, the first lipid dose is between 250 and 400 µg/kg, and the second lipid dose is between 2500 and 4000 µg/kg.

In other embodiments of the aforesaid methods, the total nucleic acid dose in the first and the second doses is between 0.2 and 0.4 mg/kg, e.g., 0.3 mg/kg.

In other embodiments of the aforesaid methods, the total lipid dose in the first and the second doses are between 3.0 and 4.5 mg/kg.

In other embodiments of the aforesaid methods, the first nucleic acid dose rate is between 0.1 and 0.15 mg/min, and the second nucleic acid dose rate is between 0.3 and 0.4 mg/min.

In other embodiments of the aforesaid methods, the first lipid dose rate is between 1.0 and 1.5 mg/min, and the second lipid dose rate is between 3.5 and 4.5 mg/min.

In other embodiments of the aforesaid methods, the first nucleic acid dose is between 1.5 and 2.0 mg and the second nucleic acid dose is between 15 and 25 mg.

In other embodiments of the aforesaid methods, the first lipid dose is between 15 and 25 mg and the second lipid dose is between 200 and 300 mg.

In another aspect, a method of reducing an infusion-related reaction, or a hypersensitivity reaction, or both, in a subject, to a composition comprising a lipid formulation, said lipid formulation comprising MC3 and a siRNA molecule is provided. The method includes administering to a subject:
- a first dose of said composition; and
- a second dose of said composition;
- wherein the first dose is administered at a first siRNA dose rate between 1.5 and 2 µg/kg/min of, and
- wherein the second dose is administered at a second siRNA dose rate between 4 and 6 µg/kg/min; and/or
- wherein the first dose is administered at a first lipid dose rate between 15 and 25 µg/kg/min, and
- wherein the second dose is administered at a second lipid dose rate between 55 and 75 µg/kg/min.

In yet another aspect, a method of reducing the expression of a target gene, or treating a disorder related to the target gene, in a subject, is provided. The method includes:
- administering to the subject a first dose and a second dose of a composition, said composition comprising a lipid formulation comprising MC3 and an siRNA molecule, wherein said first and second doses are administered in an amount sufficient to reduce expression of a target gene, or treat the disorder, in the subject; and
- wherein the first dose is administered at a first siRNA dose rate between 1.5 and 2 µg/kg/min of, and
- wherein the second dose is administered at a second siRNA dose rate between 4 and 6 µg/kg/min; and/or
- wherein the first dose is administered at a first lipid dose rate between 15 and 25 µg/kg/min, and
- wherein the second dose is administered at a second lipid dose rate between 55 and 75 µg/kg/min.

In certain embodiments of the aforesaid methods, the first dose is administered at a first siRNA dose rate between 1.5 and 2 µg/kg/min, and
- wherein the second dose is administered at a second siRNA dose rate between 4 and 6 µg/kg/min;

In other embodiments of the aforesaid methods, the first lipid dose rate is between 15 and 25 µg/kg/min, and the second lipid dose rate is between 55 and 75 µg/kg/min.

In other embodiments of the aforesaid methods, the first dose is administered at between 0.5 and 1.5 mL/min, and the second dose is administered at between 2.5 and 3.5 mL/min.

In other embodiments of the aforesaid methods, the first dose is administered over a period of between 10 and 20 minutes, and the second dose is administered over a period of between 50 and 60 minutes.

In other embodiments of the aforesaid methods, the first siRNA dose is between 20 and 30 µg/kg, and the second siRNA dose is between 250 and 300 µg/kg.

In other embodiments of the aforesaid methods, the first lipid dose is between 250 and 400 µg/kg, and the second lipid dose is between 2500 and 4000 µg/kg.

In other embodiments of the aforesaid methods, the total siRNA dose in the first and the second doses are between 0.2 and 0.4 mg/kg, e.g., 0.3 mg/kg.

In other embodiments of the aforesaid methods, the total lipid dose in the first and the second doses are between 3.0 and 4.5 mg/kg In other embodiments of the aforesaid methods, the first siRNA dose rate is between 0.1 and 0.15 mg/min, and the second siRNA dose rate is between 0.3 and 0.4 mg/min.

In other embodiments of the aforesaid methods, the first lipid dose rate is between 1.0 and 1.5 mg/min, and the second lipid dose rate is between 3.5 and 4.5 mg/min.

In other embodiments of the aforesaid methods, the first siRNA dose is between 1.5 and 2.0 mg and the second siRNA dose is between 15 and 25 mg.

In other embodiments of the aforesaid methods, the first lipid dose is between 15 and 25 mg and the second lipid dose is between 200 and 300 mg.

In other embodiments of the aforesaid methods, the lipid formulation is an LNP11 formulation.

IRR, Hypersensitivity Reaction and Biomarker Detection

A hypersensitivity reaction may occur as the doses of the compositions described herein are increased (e.g., at a dose of about 300 µg/kg). In those embodiments of increased doses, the subject can be treated with the methods and dosage regiments described herein. Alternatively, or in combination, the subject may be premedicated with one or more of a steroid, a histamine blocker or acetaminophen.

In some embodiments, the dosages and time periods of administration of the doses described herein are selected such that no substantial IRR and/or hypersensitivity reaction (e.g., a detectable hypersensitivity reaction) occurs in a subject. The IRR or the hypersensitivity reaction can be an acute reaction (e.g., can occur during dose administration or can start after the second dose administration is completed). In some embodiments, the subject is a human. Alternatively, the subject can be an animal (e.g., an animal model for a complement-mediated hypersensitivity reaction (e.g., a porcine model as described herein)). In yet other embodiments, the subject is suffering from a disorder related to expression of one or more of the target genes disclosed herein, or is at risk of developing a disorder related to expression of the target gene.

In certain embodiments, the method described herein further include the step of evaluating the subject after administration of the first dose, the second dose, or both, for the presence of one or more of the following: a skin reaction (e.g., urticaria, erythema, edema, rash, pruritus, eruptions), a hemodynamic change, e.g., a change in blood pressure (e.g., hypotension or hypertension), a respiratory problem (e.g., laryngospasm, laryngeal edema, bronchospasm, dyspnea), pain (e.g., joint pain, back pain, abdominal pain or chest pain), or other manifestations of hypersensitivity (e.g., one or more of fever, chills, nausea, vomiting or neurological changes). In one embodiment, the detection step includes evaluating one or more cardiovascular parameters.

Alternatively, or in combination, the methods described herein further include the step of evaluating the subject after administration of the first dose, the second dose, or both, for a change in a complement marker, e.g., complement activation (e.g., a change in one or more complement factors chosen from Bb or $C3a^b$), wherein an increase the level of a complement biomarker is indicative of a hypersensitivity reaction.

A change in a complement marker can be detected in vivo or using an in vitro assay. For example, a change in complement activation can be detected using an assay that detects a complement cascade component, e.g, an assay (e.g., ELISA) that detects one or more of: total complement proteins (e.g., C3 and C5); complement split products (e.g., Bb, C3a or C5a), or terminal complement complement complex: sC5b-9. Additional examples of in vitro assays for evaluating complement activity include CH50: Residual total hemolytic complement activity, or AH50: Residual alternative pathway of hemolytic complement activity. Alternatively, a change in complement activation can be detected using an animal model. In embodiments, a sample to be evaluated can be obtained from a subject exposed to the compositions described herein. For example, the sample can be a serum/plasma sample obtained for an in vivo assay. In other embodiments, naïve serum/plasma can be used for modeling complement activation in vitro.

Alternatively, or in combination, the methods described herein further include the step of evaluating the subject after administration of the first dose, the second dose, or both, for a change in thromboxane levels, e.g., thromboxane B2 in plasma, e.g., wherein an increase in the level of thromboxane is indicative of an increased hypersensitivity reaction, e.g., an increased acute hypersensitivity reaction.

Alternatively, or in combination, the methods described herein further include the step of evaluating the subject after administration of the first dose, the second dose, or both, or changes in one or more cytokines chosen from interferon-alpha, interferon-gamma, tumor necrosis factor-alpha, interleukin 1beta, interleukin 1 receptor antagonist (IL-1RA), interleukin-6, interleukin-8, interleukin-12, interleukin-18, interferon inducing protein-10, granulocyte colony stimulating factor, or C-reactive protein (CRP). In certain embodiments, an increase in the level of IL-6, IL-8, IL-1RA or CRP is indicative of an increased hypersensitivity reaction, e.g., relative to a reference parameter (e.g., a subject exposed to a bolus dose, or the subject prior to treatment).

In some embodiments, the methods described herein do not cause a detectable hypersensitivity reaction, e.g., as measured by one or more of the assays or symptoms described herein. In embodiments, the method results in a decrease in the hypersensitivity reaction, which is less than 1%, 5%, 10%, 25%, 30%, 35% or 40%, e.g., as measured by one or more of the assays or symptoms described herein. In certain embodiments, the changes described herein are compared to a reference parameter (e.g., a subject exposed to a bolus dose, or the subject prior to treatment).

In one embodiment, in response to the first and second dose regimen disclosed herein, the subject shows a reduced hypersensitivity reaction (e.g., a decreased hemodynamic change, relative to a reference parameter (e.g., a subject exposed to a bolus dose, or the subject prior to treatment).

In certain embodiments, the methods described herein cause a reduced hypersensitivity reaction, e.g., leading to a reduction (e.g., partial or complete reduction) in the administration of one or more of a steroid (e.g., dexamethasone or an equivalent), an analgesic (e.g., paracetamol), or a histamine receptor antagonist (e.g., an H1 or an H2 blocker). In other embodiments, the subject does not receive administration of a steroid (e.g., dexamethasone or an equivalent), within X hours of any of the initiation of administration of said first dose, wherein X is less than 1 hour, 2 hours, 3 hours, 5 hours, 10 hours, 15 hours, 24 hours or 48 hours.

Lipid Formulations

In some embodiments, the lipid formulation of the composition is a lipid-nucleic acid particle, e.g., a nanoparticle. In one embodiment, the nucleic acid molecules described herein are formulated in a stable nucleic acid lipid particle (SNALP). In embodiments, the lipid-nucleic acid particle has a mean diameter of about 50 nm to about 200 nm, e.g., about 50 nm to about 150 nm, about 60 nm to about 130 nm, about 70 nm to about 110 nm, or about 70 nm to about 90 nm. In yet other embodiments, the lipid-nucleic acid particle has a mean diameter of from about 70 to about 200 nm, e.g., from about 70 to about 150 nm, from about 120 to about 200 nm, or from about 90 to about 130 nm.

Typically, the lipid to drug ratio (mass/mass ratio) (e.g., lipid to RNA molecule ratio) in the composition is in the range of from about 1:1 to about 50:1, from about 1:1 to about 25:1, from about 3:1 to about 15:1, from about 4:1 to about 13:1, from about 4:1 to about 10:1, from about 5:1 to about 9:1, from about 6:1 to about 9:1, or about 13:1, about 12:1, about 11:1, about 10:1, about 9:1, about 8:1, about 7:1, about 6:1, about 5:1. In certain embodiments, the lipid to drug ratio (mass/mass ratio) (e.g., lipid to RNA molecule ratio) is in the range of from about 5:1 to 30:1, from about 6:1 to 25:1, or from about 10:1 to 15:1. In yet other embodiments, the weight to weight ratio of the nucleic acid to the lipids in the lipid-nucleic acid particle is no less than about 0.1, e.g., greater than about 0.1, greater than about 0.2, greater than about 0.3, or greater than about 0.4, e.g., between about 0.1 and about 0.4, or between about 0.2 and about 0.3. In another embodiment, the ratio of lipid:nucleic acid is at least about 1:1, at least about 2:1, at least about 3:1, at least about 4:1, at least about 5:1, at least about 6:1, at least about 7:1, at least about 8:1, at least about 10:1, at least about 11:1, at least about 12:1, at least about 15:1, or at least 30:1, e.g., between about 0.5:1 to about 15:1, about 1:1 to about 20:1, about 3:1 to about 15:1, about 4:1 to about 15:1, or about 5:1 to about 13:1.

The lipid can be a cationic or a non-cationic lipid, or a combination thereof. In other embodiments, the lipid formulation comprises a lipid-nucleic acid particle comprising a cationic lipid, a non-cationic lipid, a PEG-lipid conjugate. The lipid formulation can further include a sterol, e.g., a cholesterol.

In embodiments, the cationic lipid comprises from about 20 mol % to about 60 mol %, or about 40 mol % of the total lipid present in the formulation. In other embodiments, the cationic lipid comprises from about 2% to about 55%, e.g., from about 5% to about 45%, from about 10% to about 40%, from about 5% to about 15%, or about 40% to about 50%, by weight of the total lipid present in the lipid formulation. Examples of cationic lipid include, but are not limited to, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethylaminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), bis(3-pentyloctyl) 9-((4-(dimethylamino)butanoyl)oxy)heptadecanedioate, 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl) didodecan-2-ol (Tech G1), or a mixture thereof. Other lipids are described, e.g., in U.S. Pat. Nos. 5,976,567, 6,858,225, and 6,825,432, which are incorporated herein by references. In one embodiment, the cationic lipid is selected from the group consisting of DODAC, DDAB, DOTAP, DOTMA, DOSPA, DMRIE, DOGS, DC-Chol, and combinations thereof.

In embodiments, the lipid of the formulation is a non-cationic lipid, e.g., an anionic lipid or a neutral lipid. In embodiments, the non-cationic lipid comprises from about 5 mol % to about 90 mol %, about 10 mol %, or about 58 mol % if cholesterol is included, of the total lipid present in the formulation. In other embodiments, the non-cationic lipid comprises from about 37% to about 89%, e.g., from about 37% to about 75%, or from 40% to about 70%, by weight of the total lipid present in the lipid formulation. Examples of cationic lipid include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. In yet other embodiments, the non-cationic lipid is selected from the group consisting of DOPE, POPC, EPC, ESM, polyethylene glycol-based polymers, and combinations thereof.

A lipid component of the formulation can be conjugated or modified, e.g., to prevent or reduce aggregation of particles. In certain embodiments, the conjugated lipid is from about 0 mol % to about 20 mol %, e.g., from about 1% to about 15%, or about 2 mol % of the total lipid present in the formulation.

In one embodiment, the conjugated or modified lipid is a polyethylene glycol-modified lipid, e.g., a polyethylene glycol-modified ceramide, or a polyamide oligomer-modified lipid. In one embodiment, the PEG-lipid comprises from about 1% to about 15%, e.g., from about 3% to about 12%, e.g., about 10%, by weight of the total lipid present in the formulation. In embodiments, the PEG or PEG-modified lipid is present in the lipid formulation in a molar amount from about 0.5% to about 20%, e.g., about 0.5% to about 10%, about 0.5% to about 5%, about 1.5%, about 0.5%, about 1.5%, about 3.5%, or about 5%. The PEG or PEG-modified lipid can comprise a PEG molecule of an average molecular weight of no greater than 2,000 Da, e.g., about 2,000 Da, about 1,500 Da, about 1,000 Da, or about 500 Da.

The PEG-conjugated lipid can be chosen from a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($Ci_8$). In one embodiment, the modified lipid is PEG-CerC14 or PEG-CerC20. In yet other embodiments, the lipid formulation further comprises a PEG or PEG-modified lipid (e.g., a PEG-modified lipid chosen from one or more of PEG-$C_{14}$ to PEG-$C_{22}$, PEG-$Cer_{14}$ to PEG-$C_{20}$, or PEG-DSPE).

In embodiments, the lipid-nucleic acid particle further includes a cholesterol at, e.g., about 10 mol % to about 60 mol %, about 15% to about 50%, or about 48 mol % of the total lipid present in the formulation.

In some embodiments, the lipid formulation comprises a lipid-nucleic acid particle comprising a lipid layer surrounding and encapsulating a central region containing a nucleic acid (e.g., a polyanionic nucleic acid), wherein the lipid layer comprises a titratable lipid comprising a protonatable group having a pKa of from about 4 to about 11 (e.g., a pKa is from about 4 to about 7, from about 4 to about 6, or from about 5 to about 7). In one embodiment, the titratable lipid is an amino lipid, e.g., DODAP.

In one embodiment, the nucleic acid in the lipid formulation is not substantially degraded after incubation in serum at 37° C. for 30 minutes.

In certain embodiments, the lipid formulation comprises DLinDMA, MC3 or C12-200. Exemplary lipid formulation can include a cationic lipid of Formula I/MC3 (also called DLin-M-C3-DMA, MC3 or M-C3 described in, e.g., herein and in U.S. Pat. No. 8,158,601 incorporated by reference, and referred to herein as "MC3" or "Formula I/MC3"), or a pharmaceutically acceptable salt thereof. In certain embodiments, the cationic lipid of Formula I/MC3 is present in the lipid formulation in a molar amount from about 25% to about 75%, e.g., from about 35% to about 65%, from about 45% to about 65%, about 60%, about 57.5%, about 50%, or about 40%. In one embodiment, the lipid formulation further comprises a neutral lipid (e.g., a neutral lipid chosen from DSPC, DPPC, DMPC, POPC, DOPE or SM, or a combination thereof. In embodiments, the neutral lipid is present in the lipid formulation in a molar amount from about 0.5% to about 15%, e.g., about 3% to about 12%, from about 5% to about 10%, about 15%, about 10%, or about 7.5%. In embodiments, the lipid formulation further comprises a sterol, e.g., a cholesterol. The sterol can present in the lipid formulation in a molar amount from about 5% to about 50%, e.g., about 15% to about 45%, about 20% to about 40%, about 40%, about 38.5%, about 35%, or about 31%. In yet other embodiments, the lipid formulation further comprises a PEG or PEG-modified lipid (e.g., a PEG-modified lipid chosen from one or more of PEG-$C_{14}$ to PEG-$C_{22}$, PEG-$Cer_{14}$ to PEG-$C_{20}$, or PEG-DSPE).

In one embodiment, the lipid formulation comprises a cationic lipid of Formula I/MC3, a neutral lipid, a sterol, and a PEG or PEG-modified lipid. In embodiments, the lipid formulations can comprise:
  (i) about 25-75% of cationic lipid of Formula I/MC3, about 0.5-15% of the neutral lipid, about 5-50% of the sterol, and about 0.5-20% of the PEG or PEG-modified lipid on a molar basis;
  (ii) about 35-65% of cationic lipid of Formula I/MC3, about 3-12% of the neutral lipid, about 15-45% of the sterol, and about 0.5-10% of the PEG or PEG-modified lipid on a molar basis;
  (iii) about 45-65% of cationic lipid of Formula I/MC3, about 5-10% of the neutral lipid, about 25-40% of the sterol, and about 0.5-10% of the PEG or PEG-modified lipid on a molar basis;
  (iv) about 40-65% of cationic lipid of Formula I/MC3, about 5-10% of a neutral lipid, about 25-40% of a sterol, and about 0.5-10% of a PEG or PEG-modified lipid; (v) about 50% of cationic lipid of Formula I, about 10% of the neutral lipid (e.g., DSPC), about 38.5% of the sterol (e.g., cholesterol), and about 1.5% of the PEG or PEG-modified lipid (e.g., PEG-DMG);
  (v) about 50% of cationic lipid of Formula I/MC3, about 10% of the neutral lipid, about 35% of the sterol, and about 5% of the PEG or PEG-modified lipid; or
  (vi) about 57.2% of cationic lipid of Formula I/MC3, about 7.1% of the neutral lipid, about 34.3% of the sterol, and about 1.4% of the PEG or PEG-modified lipid.

In one embodiment, the lipid formulation comprises about 50% of cationic lipid of Formula I/MC3, about 10% of the neutral lipid (e.g., DSPC), about 38.5% of the sterol (e.g., cholesterol), and about 1.5% of the PEG or PEG-modified lipid (e.g., PEG-DMG). This lipid formulation is also referred to herein as LNP-11 (see e.g., Table 1).

The formulations described herein can be prepared by an in-line mixing method. In other embodiments, the formulation is prepared by an extrusion method.

In yet other embodiments, the lipid formulation can further comprises at least one apolipoprotein (e.g., an ApoE, active polymorphic forms, isoforms, variants and mutants, and fragments or truncated forms thereof).

In other embodiments, the lipid formulation further comprises a targeting lipid, e.g., N-acetyl galactosamine. The N-acetyl galactosamide can comprise at least a mono-, bi- or a triantennary sugar unit. In embodiments, the targeting lipid is present in the formulation in a molar amount of from about 0.001% to about 5%, e.g., from about 0.005% to about 1.5%, e.g., about 0.005%, about 0.15%, about 0.3%, about 0.5%, about 1.5%, about 2%, about 2.5%, about 3%, about 4%, or about 5%.

In other embodiments, the targeting lipid is a compound selected from the group consisting of GalNAc3-DSG (e.g., referred to as Formula II in U.S. Pat. No. 8,158,601), GalNAc3-PEG-DSG (e.g., referred to as Formula III in U.S. Pat. No. 8,158,601)), (GalNAc)$_3$-PEG-LCO (e.g., referred to as Formula IV in U.S. Pat. No. 8,158,601), Folate-PEG2000-DSG (e.g., referred to as Formula VI in U.S. Pat. No. 8,158,601), and Folate-PEG3400-DSG (e.g., referred to as Formula VII in U.S. Pat. No. 8,158,601).

Nucleic Acid/RNA Molecules

In some embodiments, the nucleic acid molecule in the composition is chosen from: double stranded RNA (dsRNA) molecules, single-stranded RNAi molecules, microRNA (miRNA), antisense RNA, short hairpin RNA (shRNA), antagomirs, mRNA, decoy RNA, DNA, plasmids or aptamers. In one embodiment, the nucleic acid molecule is an RNA molecule, e.g., an RNA molecule as described herein (e.g., an RNA molecule capable of mediating RNA interference or an iRNA). In one embodiment, the RNA molecule is double-stranded. In embodiments, the RNA molecule comprises a sense and an antisense strand. For example, the RNA molecule is a dsRNA that forms a duplex structure between 15 and 30 basepairs in length. In one embodiment, the region of complementarity between the strands is at least 17 nucleotides in length (e.g., between 19 and 25, e.g., between 19 and 21, nucleotides in length). In embodiments, each strand of the nucleic acid (e.g., RNA) molecule is no more than 30 nucleotides in length.

In other embodiments, the nucleic acid (e.g., RNA) molecules included in the compositions encompass a dsRNA having an RNA strand (the antisense strand) having a region, e.g., a region that is 30 nucleotides or less, generally 19-24 nucleotides in length, that is substantially complementary to at least part of a target mRNA.

In other embodiments, the nucleic acid (e.g., RNA) molecule is a single-stranded molecule, e.g., comprises an antisense strand.

In some embodiments, the nucleic acid (e.g., RNA) molecule is 19-21 nucleotides in length. In some embodiments, the iRNA is 19-21 nucleotides in length and is in a lipid formulation, e.g. a lipid nanoparticle (LNP) formulation (e.g., an LNP11 formulation).

In other embodiments, the nucleic acid (e.g., RNA) molecule is 21-23 nucleotides in length.

In some embodiments, the nucleic acid (e.g., RNA) molecule is from about 15 to about 25 nucleotides in length, and in other embodiments the nucleic acid (e.g., RNA) molecule is from about 25 to about 30 nucleotides in length. The nucleic acid (e.g., RNA) molecule can inhibit the expression of a target gene by at least 10%, at least 20%, at least 25%, at least 30%, at least 35% or at least 40% or more, such as when assayed by a method as described herein.

In other embodiments, the nucleic acid (e.g., RNA) molecule comprises at least one modified nucleotide. The modified nucleotides can be chosen from one or more of: a 2′-O-methyl modified nucleotide, a nucleotide comprising a 5′-phosphorothioate group, and a terminal nucleotide linked to a cholesteryl derivative or dodecanoic acid bisdecylamide group; or a 2′-deoxy-2′-fluoro modified nucleotide, a 2′-deoxy-modified nucleotide, a locked nucleotide, an abasic nucleotide, 2′-amino-modified nucleotide, 2′-alkyl-modified nucleotide, morpholino nucleotide, a phosphoramidate, and a non-natural base comprising nucleotide.

In other embodiments, least one strand of the nucleic acid (e.g., RNA) molecule comprises a 3′ overhang of at least 2 nucleotides. In other embodiments, one end of the double-stranded molecule is blunt-ended.

In embodiments, the nucleic acid (e.g., RNA) molecule has a sequence having an identity of at least 70 percent (e.g., 80%, 90%, 95% or higher) to a target mRNA. In one embodiment, the nucleic acid (e.g., RNA) molecule has a sequence complementary (e.g., is fully complementary or substantially complementary) to a target mRNA.

In certain embodiments, the target mRNA is chosen from a mammalian, plant, pathogen-associated, viral, or disease-associated mRNA. The target mRNA may be associated with a disease, e.g., a tumor-associated mRNA, or an autoimmune disease-associated mRNA.

Target genes can be chosen from: Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA (p21) gene, MYB gene, JUN gene, FOS gene, BCL-2 gene, HAMP, Activated Protein C gene, Cyclin D gene, VEGF gene, antithrombin 3 gene, aminolevulinate synthase 1 gene, alpha-1-antitrypsin gene, tmprss6 gene, apoa1 gene, apoc3 gene, bc11a gene, klf gene, angptl3 gene, plk gene, PKN3 gene, HBV, HCV, p53 gene, angiopoietin gene, angiopoietin-like 3 gene, complement component 3 (C3) gene, or complement component 5 (C5) gene. In certain embodiments, the target is chosen from: Eg5, PCSK9, TTR, HAMP, VEGF gene, antithrombin 3 gene, aminolevulinate synthase 1 gene, alpha-1-antitrypsin gene, or tmprss6 gene.

In certain embodiments, the nucleic acid molecules as described herein target a wildtype target RNA transcript variant, a mutant transcript, or a combination thereof. For example, the nucleic acid molecule can target a polymorphic variant, such as a single nucleotide polymorphism (SNP), of the target gene. In another embodiment, the nucleic acid molecule targets both a wildtype and a mutant target gene transcript. In other embodiments, the nucleic acid molecule targets a non-coding region of the target RNA transcript, such as the 5' or 3' untranslated region of a transcript.

Kits

In another aspect, the invention features a kit for administration of a first dose and a second dose of a composition (e.g., a first and a second dose as described herein). The kit includes:
providing a composition, said composition comprising a lipid formulation and a nucleic acid (e.g., RNA) molecule, wherein said second amount is greater than said first amount; and
instruction for administration, wherein the first dose is instructed to be administered over a time period that is no more than 1/X, wherein X is 2, 3, 4, 5, 6, 7, 8, 9 or 10, of the time period over which the second dose is administered; and
the rate of administration, e.g., in mg/min or mL/min, of said first dose is no more than 1/X, wherein X is 2, 3, 4, 5, 6, 7, 8, 9, 10, 15, 20, 30, 40 or 50, of the rate of administration of said second dose;

Devices

In another aspect, the invention features a device, e.g., a device for intravenous administration, comprising:
a reservoir, e.g., a bag, containing a composition (e.g., a composition that can be administered at a first and/or a second dose as described herein), said composition comprising a lipid formulation and a nucleic acid (e.g., RNA) molecule as described herein;
a conduit (e.g., tubing);
a means (e.g., a valve) for adjusting a rate of administration of the composition; and
(optionally) a needle;
wherein said conduit communicates said reservoir to the means (e.g., valve) (and optionally, a second conduit that connects to the needle), and wherein:
a) the composition is administered at a first dose (e.g., a first dose as described herein) over a time period that is no more than 1/X, wherein X is 2, 3, 4, 5, 6, 7, 8, 9 or 10, of the time period over which the second dose is administered; or
b) the rate of administration, e.g., in mg/min or mL/min, of said first dose is no more than 1/X, wherein X is 2, 3, 4, 5, 6, 7, 8, 9, 10, 15, 20, 30, 40 or 50, of the rate of administration of said second dose.

All publications, patent applications, patents, and other references mentioned herein are incorporated by reference in their entirety.

The details of various embodiments of the invention are set forth in the description below. Other features, objects, and advantages of the invention will be apparent from the description and the drawings, and from the claims.

DETAILED DESCRIPTION OF THE INVENTION

Figure 1:
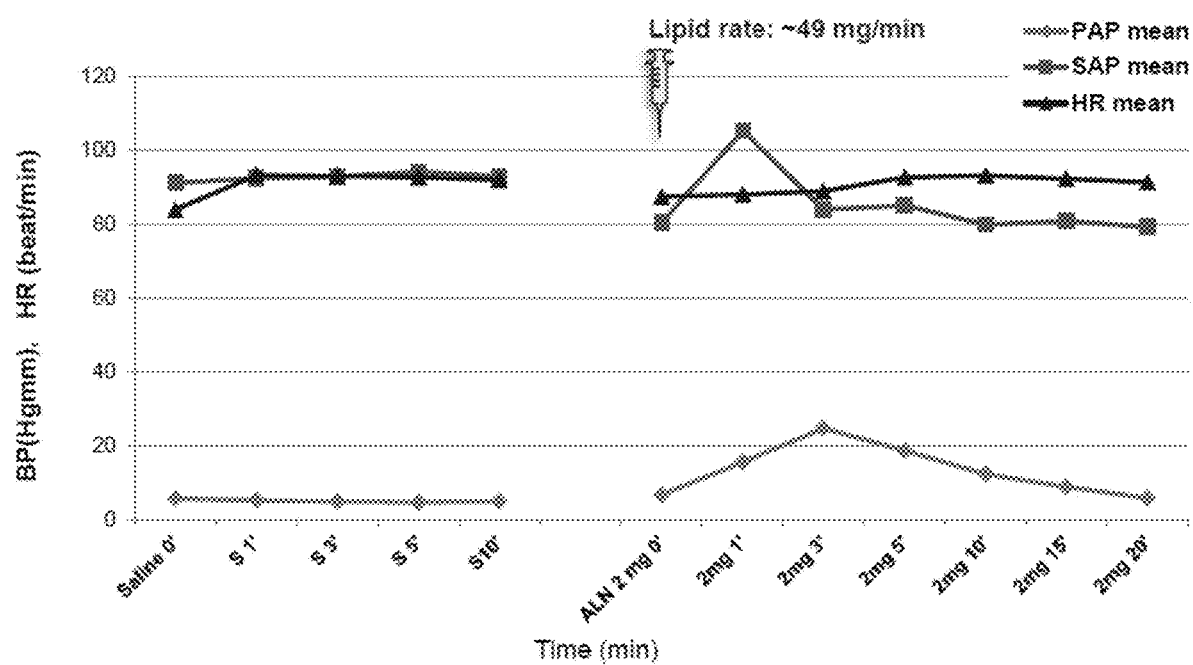
FIG. 1 depicts the hemodynamic changes (PAP, SAP and HR) after first bolus dose of siRNA-LNP formulation in pig 1.

Infusion-related reactions (IRRs) relate to any signs or symptoms experienced by a patient during infusion of a pharmacological or biological agent (e.g., a drug). These reactions can be acute, and typically occur during the first hour(s) or day after drug administration. Acute infusion-related reactions include a variety of signs and symptoms, including, but not limited to, neurologic (e.g., dizziness, headache, weakness, syncope, seizure), psychiatric (e.g., anxiety), cardiovascular (e.g., tachycardia, hypotension, arrhythmia, chest pain, ischemia or infarction, cardiac arrest), cutaneous (e.g., flushing, erythema, pruritus, urticaria, angioedema, maculopapular rash), and gastrointestinal signs and symptoms. Manifestations of IRRs can vary, and can include drug hypersensitivity reactions (reviewed e.g., by Kang, S. P. and Saif, M. S. (2007) The Journal of Supportive Oncology, Vol. 5 (9):451-457).

Hypersensitivity reactions can be classified into immune mediated and non-immune mediated hypersensitivity reactions. Immune mediated hypersensitivity reactions relate to specific, adaptive immune responses generated against an antigen, e.g., a drug. Non-immune mediated hypersensitivity reactions relate to drug responses initiated by some pharmacological action of the drug, which can involve immune system components. Non-immune mediated hypersensitivity reactions, also referred to as pseudoallergic or anaphylactoid reactions, have clinical manifestations that are often indistinguishable from allergic reactions. These reactions are believed to be associated with complement activation, as well as degranulation of mast cells and/or basophils leading to histamine release and an anaphylactic-like reaction. Non-immune mediated hypersensitivity reactions may involve cytokine release syndrome, either directly via pharmacology or indirectly through antibody dependent cellular cytotoxity (ADCC). Id.

Without wishing to be bound by theory, Applicants have discovered that infusion reactions to compositions that include a lipid formulation and an RNA molecule appear to be associated with an IRR or a hypersensitivity reaction. For example, dose ranges of 0.1 to 1.25 mg/kg of siRNAs in human subjects premedicated with steroid, H1/H2 blockers and acetaminophen have been shown to activate a hypersensitivity response in about 15% of patients. These dose ranges are typically administered as a continuous, single dose for a predetermined time interval, e.g., 60 minutes. The incidence of the IRR or hypersensitivity response correlates with lipid dose rate (for example, having a threshold of approx. 13 mg/min). Such IRR or hypersensitivity responses have been reduced by readministration of the dose. Modified lipid-nucleic acid particles (e.g., LNP-11 formulated particles) with improved efficacy have resulted in a reduction of the dose range to 0.01-0.5 mg/kg siRNA, provided during an infusion interval over 60 mins. Subjects receiving the modified lipid-nucleic acid particles had a lipid dose rate associated with the hypersensitivity reaction of approx. 8 mg/min. One subject showed a hypersensitivity response at higher doses (e.g., 0.5 mg/kg) to which the subject was able to complete the dose by slowing the infusion rate.

In one embodiment, it has been discovered that administration of a first dose (or a pre-dose) of a lipid-formulated RNA molecule corresponding to a portion of a second dose or the total dose, or administration of a first dose at a portion of the rate of infusion of a second dose, over a pre-treatment interval was found to reduce or prevent the IRR or hypersensitivity response in a subject. Accordingly, methods, kits and devices for dosing a subject to reduce an IRR and/or a hypersensitivy response to a lipid-formulated RNA molecule are disclosed.

The term, "infusion-related reaction" or "IRR" relates to any sign or symptom experienced by a subject, e.g., a patient, during infusion of a pharmacological or biological agent (e.g., a drug). These reactions can be acute, and typically occur during the first hours or a day after drug administration. IRRs can include, but are not limited to, the hypersensitivity reactions described herein.

As used herein, the term "hypersensitivity reaction" encompass any adverse event (e.g., immune-mediated and non-immune mediated) related to administration of a pharmacological agent (e.g., an RNA molecule or an iRNA as described herein), regardless of etiology. In one embodiment, the hypersensitivity reaction is a non-immune mediated hypersensitivity reaction or a pseudoallergic reaction. Symptoms associated with hypersensitivity reactions (both immune and non-immune reactions) include, but are not limited to, flushing, various types of skin rashes (e.g., urticaria, erythema, edema, rash, pruritus, eruptions); hemodynamic changes, e.g., a change in blood pressure (e.g., hypotension or hypertension) and/or heart rate; respiratory problems (e.g., laryngospasm, laryngeal edema, bronchospasm, dyspnea, or chest discomfort); pain (e.g., joint pain, back pain, abdominal pain or chest pain); or other manifestations of hypersensitivity (e.g., one or more of fever, chills, nausea, gastrointestinal disturbances (e.g., vomiting), hypoxia, neurological changes, or cardiac arrest or shock.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

As used herein, the term "iRNA," "RNAi", "iRNA agent," or "RNAi agent" refers to an agent that contains RNA as that term is defined herein, and which mediates the targeted cleavage of an RNA transcript, e.g., via an RNA-induced silencing complex (RISC) pathway. In one embodiment, an iRNA as described herein effects inhibition of TTR expression. Inhibition of target gene expression may be assessed based on a reduction in the level of target gene mRNA or a reduction in the level of the target gene protein. As used herein, "target sequence" refers to a contiguous portion of the nucleotide sequence of an mRNA molecule formed during the transcription of a target gene, including mRNA that is a product of RNA processing of a primary transcription product. The target portion of the sequence will be at least long enough to serve as a substrate for iRNA-directed cleavage at or near that portion. For example, the target sequence will generally be from 9-36 nucleotides in length, e.g., 15-30 nucleotides in length, including all subranges therebetween. As non-limiting examples, the target sequence can be from 15-30 nucleotides, 15-26 nucleotides, 15-23 nucleotides, 15-22 nucleotides, 15-21 nucleotides, 15-20 nucleotides, 15-19 nucleotides, 15-18 nucleotides, 15-17 nucleotides, 18-30 nucleotides, 18-26 nucleotides, 18-23 nucleotides, 18-22 nucleotides, 18-21 nucleotides, 18-20 nucleotides, 19-30 nucleotides, 19-26 nucleotides, 19-23 nucleotides, 19-22 nucleotides, 19-21 nucleotides, 19-20 nucleotides, 20-30 nucleotides, 20-26 nucleotides, 20-25 nucleotides, 20-24 nucleotides, 20-23 nucleotides, 20-22 nucleotides, 20-21 nucleotides, 21-30 nucleotides, 21-26 nucleotides, 21-25 nucleotides, 21-24 nucleotides, 21-23 nucleotides, or 21-22 nucleotides.

As used herein, the term "strand comprising a sequence" refers to an oligonucleotide comprising a chain of nucleotides that is described by the sequence referred to using the standard nucleotide nomenclature.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they may form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding a target gene protein). For example, a polynucleotide is complementary to at least a part of a target gene mRNA if the sequence is substantially complementary to a non-interrupted portion of an mRNA encoding target gene. As another example, a polynucleotide is complementary to at least a part of a target gene mRNA if the sequence is substantially complementary to a non-interrupted portion of an mRNA encoding target gene.

The term "double-stranded RNA" or "dsRNA," as used herein, refers to an iRNA that includes an RNA molecule or complex of molecules having a hybridized duplex region that comprises two anti-parallel and substantially complementary nucleic acid strands, which will be referred to as having "sense" and "antisense" orientations with respect to a target RNA. The duplex region can be of any length that permits specific degradation of a desired target RNA, e.g., through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. dsRNAs generated in the cell by processing with Dicer and similar enzymes are generally in the range of 19-22 base pairs in length. One strand of the duplex region of a dsDNA comprises a sequence that is substantially complementary to a region of a target RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker." The term "siRNA" is also used herein to refer to a dsRNA as described above.

In another embodiment, the iRNA agent may be a "single-stranded siRNA" that is introduced into a cell or organism to inhibit a target mRNA. Single-stranded RNAi agents bind to the RISC endonuclease Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) Cell 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150; 883-894.

In another aspect, the RNA agent is a "single-stranded antisense RNA molecule". An single-stranded antisense RNA molecule is complementary to a sequence within the target mRNA. Single-stranded antisense RNA molecules can inhibit translation in a stoichiometric manner by base pairing to the mRNA and physically obstructing the translation machinery, see Dias, N. et al., (2002) *Mol Cancer Ther* 1:347-355. Alternatively, the single-stranded antisense molecules inhibit a target mRNA by hydridizing to the target and cleaving the target through an RNaseH cleavage event. The single-stranded antisense RNA molecule may be about 10 to about 30 nucleotides in length and have a sequence that is complementary to a target sequence. For example, the single-stranded antisense RNA molecule may comprise a sequence that is at least about 10, 11, 12, 13, 14, 15, 16, 17, 18, 19, 20, or more contiguous nucleotides from any one of the antisense nucleotide sequences described herein.

The term "nucleic acid molecule" encompasses an RNA molecule (e.g., an RNA molecule as described herein), a DNA molecule (e.g., a 100% deoxynucleoside-containing molecule), and a combination of an RNA and a DNA molecule. It includes a naturally-occurring and non-naturally-occurring nucleic acid molecule. In one embodiment, the nucleic acid molecule is isolated or purified. In one embodiment, the nucleic acid molecule is synthetic (e.g., chemically synthesized) or recombinant. In other embodiments, the nucleic acid molecule is a non-naturally-occurring nucleic acid molecule, e.g., an analog or a derivative of a nucleic acid molecule, e.g., analogs and derivatives of DNA, RNA or both. For example, the nucleic acid molecule can include one or more nucleotide/nucleoside analogs or derivatives as described herein or as known in the art. In certain embodiments, "nucleic acid molecule" includes an oligonucleotide molecule (e.g., a single-stranded or a double-stranded oligonucleotide (e.g., an oligodeoxyribo- or an oligoribonucleotide, or a combination thereof)). In other embodiments, "nucleic acid molecule" includes an RNA molecule, e.g., a single-stranded or a double-stranded RNA (dsRNA), e.g., as described herein. In certain embodiments, the nucleic acid molecule comprises at least 5, 10, 15, 20, 25, 30, 35, 40, 45, 50, 55, 60, 65, 70, 75, 80, 85, 90, 95% or 100% deoxyribonucleosides, e.g., in one or both strands.

The term "RNA molecule" or "ribonucleic acid molecule" encompasses a naturally-occurring and non-naturally-occurring RNA molecule. In one embodiment, the RNA molecule is isolated or purified. In one embodiment, the RNA molecule is synthetic (e.g., chemically synthesized) or recombinant. In other embodiments, the RNA molecule is a non-naturally-occurring RNA molecule, e.g., an analog or a derivative of an RNA molecule. In certain embodiments, the RNA molecule comprises one or more ribonucleotide/ribonucleoside analogs or derivatives as described herein or as known in the art. A "ribonucleoside" includes a nucleoside base and a ribose sugar, and a "ribonucleotide" is a ribonucleoside with one, two or three phosphate moieties. However, the terms "ribonucleoside" and "ribonucleotide" can be considered to be equivalent as used herein. The ribonucleoside or ribonucleotide can be modified in the nucleobase structure or in the ribose-phosphate backbone structure, e.g., as described herein below. In certain embodiments, the RNA molecule that comprises a ribonucleoside analog or derivative retains the ability to form a duplex. As non-limiting examples, an RNA molecule can also include at least one modified ribonucleoside, including but not limited to, a 2□O-methyl modified nucleoside, a nucleoside comprising a 5□phosphorothioate group, a terminal nucleoside linked to a cholesteryl derivative or dodecanoic acid bisdecylamide group, a locked nucleoside, an abasic nucleoside, a 2□deoxy-2□fluoro modified nucleoside, a 2 amino-modified nucleoside, 2□alkyl-modified nucleoside, morpholino nucleoside, a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the RNA molecule. The modifications need not be the same for each of such a plurality of modified ribonucleosides in an RNA molecule. In one embodiment, modified RNA molecules contemplated for use in methods and compositions described herein include peptide nucleic acids (PNAs) that have the ability to form the required duplex structure and that permit or mediate the specific degradation of a target RNA, e.g., via a RISC pathway.

Exemplary RNA molecules, include but are not limited to, iRNA agents or molecules, double stranded RNA (dsRNA) molecules, siRNA molecules, single-stranded RNAi molecules, single-stranded siRNA molecules, microRNA (miRNA), antisense RNA, short hairpin RNA (shRNA), antagomirs, mRNA, decoy RNA, vectors and aptamers.

In certain embodiments, an RNA molecule comprises a deoxyribonucleoside. For example, the RNA molecule, e.g., an iRNA agent, can comprise one or more deoxynucleosides, including, for example, a deoxynucleoside overhang(s), or one or more deoxynucleosides within the double stranded portion of a dsRNA. In certain embodiments, the RNA molecule comprises a percentage of deoxyribonucleoses of at least 5, 10, 15, 20, 25, 30, 35, 40, 45, 50, 55, 60, 65, 70, 75, 80, 85, 90, 95% or higher (but not 100%) deoxyribonucleosides, e.g., in one or both strands. In certain embodiments, the term "iRNA" does not encompass a double stranded DNA molecule (e.g., a naturally-occurring double stranded DNA molecule or a 100% deoxynucleoside-containing DNA molecule).

In one aspect, an RNA interference agent includes a single stranded RNA that interacts with a target RNA sequence to direct the cleavage of the target RNA. Without wishing to be bound by theory, long double stranded RNA introduced into cells is broken down into siRNA by a Type III endonuclease known as Dicer (Sharp et al., *Genes Dev.* 2001, 15:485). Dicer, a ribonuclease-III-like enzyme, processes the dsRNA into 19-23 base pair short interfering RNAs with characteristic two base 3□ overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleaves the target to induce silencing (Elbashir, et al., (2001) *Genes Dev.* 15:188). Thus, in one aspect the invention relates to a single stranded RNA that promotes the formation of a RISC complex to effect silencing of the target gene.

As used herein, the term "nucleotide overhang" refers to at least one unpaired nucleotide that protrudes from the duplex structure of an iRNA, e.g., a dsRNA. For example, when a 3 Lend of one strand of a dsRNA extends beyond the 5□end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5′ end, 3′ end or both ends of either an antisense or sense strand of a dsRNA.

In one embodiment, the antisense strand of a dsRNA has a 1-10 nucleotide overhang at the 3' end and/or the 5' end. In one embodiment, the sense strand of a dsRNA has a 1-10 nucleotide overhang at the 3' end and/or the 5' end. In another embodiment, one or more of the nucleotides in the overhang is replaced with a nucleoside thiophosphate.

The terms "blunt" or "blunt ended" as used herein in reference to a dsRNA mean that there are no unpaired nucleotides or nucleotide analogs at a given terminal end of a dsRNA, i.e., no nucleotide overhang. One or both ends of a dsRNA can be blunt. Where both ends of a dsRNA are blunt, the dsRNA is said to be blunt ended. To be clear, a "blunt ended" dsRNA is a dsRNA that is blunt at both ends, i.e., no nucleotide overhang at either end of the molecule. Most often such a molecule will be double-stranded over its entire length.

The term "anti sense strand" or "guide strand" refers to the strand of an iRNA, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," or "passenger strand" as used herein, refers to the strand of an iRNA that includes a region that is substantially complementary to a region of the antisense strand as that term is defined herein.

As used herein, the term "SNALP" refers to a stable nucleic acid-lipid particle. A SNALP represents a vesicle of lipids coating a reduced aqueous interior comprising a nucleic acid such as an iRNA or a plasmid from which an iRNA is transcribed. SNALPs are described, e.g., in U.S. Patent Application Publication Nos. 20060240093, 20070135372, and in International Application No. WO 2009082817. These applications are incorporated herein by reference in their entirety.

"Introducing into a cell," when referring to an iRNA, means facilitating or effecting uptake or absorption into the cell, as is understood by those skilled in the art. Absorption or uptake of an iRNA can occur through unaided diffusive or active cellular processes, or by auxiliary agents or devices. The meaning of this term is not limited to cells in vitro; an iRNA may also be "introduced into a cell," wherein the cell is part of a living organism. In such an instance, introduction into the cell will include the delivery to the organism. For example, for in vivo delivery, iRNA can be injected into a tissue site or administered systemically. In vivo delivery can also be by a β-glucan delivery system, such as those described in U.S. Pat. Nos. 5,032,401 and 5,607,677, and U.S. Publication No. 2005/0281781, which are hereby incorporated by reference in their entirety. In vitro introduction into a cell includes methods known in the art such as electroporation and lipofection. Further approaches are described herein below or known in the art.

As used herein, the term "modulate the expression of," refers to at an least partial "inhibition" or partial "activation" of a target gene expression in a cell treated with an iRNA composition as described herein compared to the expression of target gene in a control cell. A control cell includes an untreated cell, or a cell treated with a non-targeting control iRNA.

The terms "activate," "enhance," "up-regulate the expression of," "increase the expression of," and the like, in so far as they refer to a target gene, herein refer to the at least partial activation of the expression of a target gene, as manifested by an increase in the amount of target gene mRNA, which may be isolated from or detected in a first cell or group of cells in which a target gene is transcribed and which has or have been treated such that the expression of a target gene is increased, as compared to a second cell or group of cells substantially identical to the first cell or group of cells but which has or have not been so treated (control cells).

In one embodiment, expression of a target gene is activated by at least about 10%, 15%, 20%, 25%, 30%, 35%, 40%, 45%, or 50% by administration of an iRNA as described herein. In some embodiments, a target gene is activated by at least about 60%, 70%, or 80% by administration of an iRNA featured in the invention. In some embodiments, expression of a target gene is activated by at least about 85%, 90%, or 95% or more by administration of an iRNA as described herein. In some embodiments, the target gene expression is increased by at least 1-fold, at least 2-fold, at least 5-fold, at least 10-fold, at least 50-fold, at least 100-fold, at least 500-fold, at least 1000 fold or more in cells treated with an iRNA as described herein compared to the expression in an untreated cell. Activation of expression by small dsRNAs is described, for example, in Li et al., 2006 *Proc. Natl. Acad. Sci. U.S.A.* 103:17337-42, and in US20070111963 and US2005226848, each of which is incorporated herein by reference.

The terms "silence," "inhibit expression of," "down-regulate expression of," "suppress expression of," and the like, in so far as they refer to a target gene, herein refer to the at least partial suppression of the expression of a target gene, as assessed, e.g., based on target gene mRNA expression, target gene protein expression, or another parameter functionally linked to target gene expression. For example, inhibition of target gene expression may be manifested by a reduction of the amount of target gene mRNA which may be isolated from or detected in a first cell or group of cells in which a target gene is transcribed and which has or have been treated such that the expression of a target gene is inhibited, as compared to a control. The control may be a second cell or group of cells substantially identical to the first cell or group of cells, except that the second cell or group of cells have not been so treated (control cells). The degree of inhibition is usually expressed as a percentage of a control level, e.g., $$\frac{(\text{mRNA in control cells}) - (\text{mRNA in treated cells})}{(\text{mRNA in control cells})} \cdot 100\%$$

Alternatively, the degree of inhibition may be given in terms of a reduction of a parameter that is functionally linked to target gene expression, e.g., the amount of protein encoded by a target gene. The reduction of a parameter functionally linked to target gene expression may similarly be expressed as a percentage of a control level. In principle, target gene silencing may be determined in any cell expressing target gene, either constitutively or by genomic engineering, and by any appropriate assay. However, when a reference is needed in order to determine whether a given iRNA inhibits the expression of the target gene by a certain degree and therefore is encompassed by the instant invention, the assays provided in the Examples below shall serve as such reference.

For example, in certain instances, expression of a target gene is suppressed by at least about 10%, 15%, 20%, 25%, 30%, 35%, 40%, 45%, or 50% by administration of an iRNA featured in the invention. In some embodiments, a target gene is suppressed by at least about 60%, 65%, 70%, 75%, or 80% by administration of an iRNA featured in the invention. In some embodiments, a target gene is suppressed by at least about 85%, 90%, 95%, 98%, 99%, or more by administration of an iRNA as described herein.

As used herein in the context of target gene expression, the terms "treat," "treating," "treatment," and the like, refer to relief from or alleviation of pathological processes related to target gene expression. In the context of the present invention insofar as it relates to any of the other conditions recited herein below (other than pathological processes related to target gene expression), the terms "treat," "treatment," and the like mean to prevent, relieve or alleviate at least one symptom associated with such condition, or to slow or reverse the progression or anticipated progression of such condition. Thus, unless the context clearly indicates otherwise, the terms "treat," "treatment," and the like are intended to encompass prophylaxis, e.g., prevention of disorders and/or symptoms of disorders related to target gene expression.

By "lower" in the context of a disease marker or symptom is meant a statistically or clinically significant decrease in such level. The decrease can be, for example, at least 10%, at least 20%, at least 30%, at least 40% or more, and is typically down to a level accepted as within the range of normal for an individual without such disorder.

As used herein, the phrases "therapeutically effective amount" and "prophylactically effective amount" refer to an amount that provides a therapeutic benefit in the treatment, prevention, or management of pathological processes related to target gene expression. The specific amount that is therapeutically effective can be readily determined by an ordinary medical practitioner, and may vary depending on factors known in the art, such as, for example, the type of pathological process, the patient's history and age, the stage of pathological process, and the administration of other agents.

As used herein, a "pharmaceutical composition" comprises a pharmacologically effective amount of an iRNA and a pharmaceutically acceptable carrier. As used herein, "pharmacologically effective amount," "therapeutically effective amount" or simply "effective amount" refers to that amount of an iRNA effective to produce the intended pharmacological, therapeutic or preventive result. For example, in a method of treating a disorder related to target gene expression, an effective amount includes an amount effective to reduce one or more symptoms associated with the disease, or an amount effective to reduce the risk of developing conditions associated with the disease. For example, if a given clinical treatment is considered effective when there is at least a 10% reduction in a measurable parameter associated with a disease or disorder, a therapeutically effective amount of a drug for the treatment of that disease or disorder is the amount necessary to effect at least a 10% reduction in that parameter. For example, a therapeutically effective amount of an iRNA targeting target gene can reduce target gene protein levels by any measurable amount, e.g., by at least 10%, 20%, 30%, 40% or 50%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

The term "about" when referring to a number or a numerical range means that the number or numerical range referred to is an approximation within experimental variability (or within statistical experimental error), and thus the number or numerical range may vary from, for example, between 1% and 15% of the stated number or numerical range.

Double-Stranded Ribonucleic Acid (dsRNA)

Described herein are iRNA agents that inhibit the expression of a target genegene. In one embodiment, the iRNA agent includes double-stranded ribonucleic acid (dsRNA) molecules for inhibiting the expression of a target gene in a cell or in a subject (e.g., in a mammal, e.g., in a human), where the dsRNA includes an antisense strand having a region of complementarity which is complementary to at least a part of an mRNA formed in the expression of a target genegene, and where the region of complementarity is 30 nucleotides or less in length, generally 19-24 nucleotides in length, and where the dsRNA, upon contact with a cell expressing the target gene, inhibits the expression of the target gene by at least 10% as assayed by, for example, a PCR or branched DNA (bDNA)-based method, or by a protein-based method, such as by Western blot. In one embodiment, the iRNA agent activates the expression of a target gene in a cell or mammal. Expression of a target gene in cell culture, such as in COS cells, HeLa cells, primary hepatocytes, HepG2 cells, primary cultured cells or in a biological sample from a subject can be assayed by measuring target gene mRNA levels, such as by bDNA or TaqMan assay, or by measuring protein levels, such as by immunofluorescence analysis, using, for example, Western Blotting or flow cytometric techniques.

A dsRNA includes two RNA strands that are sufficiently complementary to hybridize to form a duplex structure under conditions in which the dsRNA will be used. One strand of a dsRNA (the anti sense strand) includes a region of complementarity that is substantially complementary, and generally fully complementary, to a target sequence, derived from the sequence of an mRNA formed during the expression of a target gene. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, e.g., 15-30 nucleotides in length.

One of skill in the art will also recognize that the duplex region is a primary functional portion of a dsRNA, e.g., a duplex region of 9 to 36, e.g., 15-30 base pairs. Thus, in one embodiment, to the extent that it becomes processed to a functional duplex of e.g., 15-30 base pairs that targets a desired RNA for cleavage, an RNA molecule or complex of RNA molecules having a duplex region greater than 30 base pairs is a dsRNA. Thus, an ordinarily skilled artisan will recognize that in one embodiment, then, a miRNA is a dsRNA. In another embodiment, a dsRNA is not a naturally occurring miRNA. In another embodiment, an iRNA agent useful to target target gene expression is not generated in the target cell by cleavage of a larger dsRNA.

A dsRNA as described herein may further include one or more single-stranded nucleotide overhangs. The dsRNA can be synthesized by standard methods known in the art as further discussed below, e.g., by use of an automated DNA synthesizer, such as are commercially available from, for example, Biosearch, Applied Biosystems, Inc. In one embodiment, a target gene is a human target gene. In another embodiment the target gene is a mouse or a rat target gene. In specific embodiments, the first sequence is a sense strand of a dsRNA that includes a sense sequence, and the second sequence is an antisense strand of a dsRNA that includes an antisense sequence. Alternative dsRNA agents that target sequences other than those of the dsRNAs disclosed herein can readily be determined using the target sequence and the flanking target gene sequence.

The skilled person is well aware that dsRNAs having a duplex structure of between 20 and 23, but specifically 21, base pairs have been hailed as particularly effective in inducing RNA interference (Elbashir et al., EMBO 2001, 20:6877-6888). However, others have found that shorter or longer RNA duplex structures can be effective as well. In the embodiments described above, dsRNAs described herein can include at least one strand of a length of minimally 21 nucleotides. It can be reasonably expected that shorter duplexes minus only a few nucleotides on one or both ends may be similarly effective as compared to the dsRNAs described above.

Hence, dsRNAs having a partial sequence of at least 15, 16, 17, 18, 19, 20, or more contiguous nucleotides, and differing in their ability to inhibit the expression of a target genegene by not more than 5, 10, 15, 20, 25, or 30% inhibition from a dsRNA comprising the full sequence, are contemplated according to the invention.

In addition, the RNAs identify a site in a target gene transcript that is susceptible to RISC-mediated cleavage. As such, the present invention further features iRNAs that target within one of such sequences. As used herein, an iRNA is said to target within a particular site of an RNA transcript if the iRNA promotes cleavage of the transcript anywhere within that particular site. Such an iRNA will generally include at least 15 contiguous nucleotides coupled to additional nucleotide sequences taken from the region contiguous to the selected sequence in a target gene.

While a target sequence is generally 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that may serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified further optimization can be achieved by systematically either adding or removing nucleotides to generate longer or shorter sequences and testing those and sequences generated by walking a window of the longer or shorter size up or down the target RNA from that point. Again, coupling this approach to generating new candidate targets with testing for effectiveness of iRNAs based on those target sequences in an inhibition assay as known in the art or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes, etc.) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch not be located in the center of the region of complementarity. If the antisense strand of the iRNA contains mismatches to the target sequence, it is preferable that the mismatch be restricted to be within the last 5 nucleotides from either the 5' or 3' end of the region of complementarity. For example, for a 23 nucleotide iRNA agent RNA strand which is complementary to a region of a target gene, the RNA strand generally does not contain any mismatch within the central 13 nucleotides. The methods described herein or methods known in the art can be used to determine whether an iRNA containing a mismatch to a target sequence is effective in inhibiting the expression of a target gene. Consideration of the efficacy of iRNAs with mismatches in inhibiting expression of a target gene is important, especially if the particular region of complementarity in a target gene is known to have polymorphic sequence variation within the population.

In one embodiment, at least one end of a dsRNA has a single-stranded nucleotide overhang of 1 to 4, generally 1 or 2 nucleotides. dsRNAs having at least one nucleotide overhang have unexpectedly superior inhibitory properties relative to their blunt-ended counterparts. In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in this invention include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —CH$_2$—NH—CH$_2$—, —CH$_2$—N(CH$_3$)—O—CH$_2$— [known as a methylene (methylimino) or MMI backbone], —CH$_2$—O—N(CH$_3$)—CH$_2$—, —CH$_2$—N(CH$_3$)—N(CH$_3$)—CH$_2$— and —N(CH$_3$)—CH$_2$—CH$_2$—[wherein the native phosphodiester backbone is represented as —O—P—O—CH$_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs may also contain one or more substituted sugar moieties. The iRNAs, e.g., dsRNAs, featured herein can include one of the following at the 2' position: OH; F; O-, S-, or N-alkyl; O-, S-, or N-alkenyl; O-, S- or N-alkynyl;

or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2′ position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2′-methoxyethoxy (2′-O—$CH_2CH_2OCH_3$, also known as 2′-O-(2-methoxyethyl) or 2′-MOE) (Martin et al., *Helv. Chim. Acta*, 1995, 78:486-504) i.e., an alkoxy-alkoxy group. Another exemplary modification is 2′-dimethylaminooxyethoxy, i.e., a $O(CH_2)_2ON(CH_3)_2$ group, also known as 2′-DMAOE, as described in examples herein below, and 2′-dimethylaminoethoxyethoxy (also known in the art as 2′-O-dimethylaminoethoxyethyl or 2′-DMAEOE), i.e., 2′-O—$CH_2$—O—$CH_2$—$N(CH_3)_2$, also described in examples herein below.

Other modifications include 2′-methoxy (2′-$OCH_3$), 2′-aminopropoxy (2′-$OCH_2CH_2CH_2NH_2$) and 2′-fluoro (2′-F). Similar modifications may also be made at other positions on the RNA of an iRNA, particularly the 3′ position of the sugar on the 3′ terminal nucleotide or in 2′-5′ linked dsRNAs and the 5′ position of 5′ terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2′-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2′ and 4′ carbons. This structure effectively "locks" the ribose in the 3′-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193).

Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2′0-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

iRNA Motifs

In one embodiment, the sense strand sequence may be represented by formula (I):

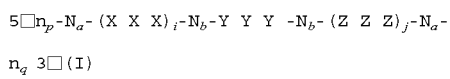

wherein:

i and j are each independently 0 or 1;

p and q are each independently 0-6;

each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8; 7, 8, 9; 8, 9, 10; 9, 10, 11; 10, 11, 12 or 11, 12, 13) of - the sense strand, the count starting from the 1$^{st}$ nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas:

5□$n_p$-$N_a$-YYY-$N_b$-ZZZ-$N_a$-$n_q$ 3□(Ib);

5□$n_p$-$N_a$-XXX-$N_b$-YYY-$N_a$-$n_q$ 3□(Ic);
or

5□$n_p$-$N_a$-XXX-$N_b$-YYY-$N_b$-ZZZ-$N_a$-$n_q$ 3□(Id).

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6. Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

5□$n_p$-$N_a$-YYY-$N_a$-$n_q$ 3□(Ia).

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

5□$n_q$'-$N_a$'-(Z'Z'Z')$_k$-$N_b$'-Y'Y'Y'-$N_b$'-(X'X'X')$_l$-

$N_a$'-$n_p$' 3'  (II)

wherein:

k and l are each independently 0 or 1;

p' and q' are each independently 0-6;

each $N_a$' independently represents an oligonucleotide sequence comprising 0-25 modified nucleotides, each sequence comprising at least two differently modified nucleotides;

each $N_b$' independently represents an oligonucleotide sequence comprising 0-10 modified nucleotides;

each $n_p$' and $n_q$' independently represent an overhang nucleotide;

wherein $N_b$' and Y' do not have the same modification; and

X'X'X', Y'Y'Y' and Z'Z'Z' each independently represent one motif of three identical modifications on three consecutive nucleotides.

In one embodiment, the $N_a$' and/or $N_b$' comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1$^{st}$ nucleotide, from the 5'-end; or optionally, the count starting at the 1$^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

5□$n_q$'-$N_a$'-Z'Z'Z'-$N_b$'-Y'Y'Y'-$N_a$'-$n_p$'. 3□ (IIb);

5□$n_q$'-$N_a$'-Y'Y'Y'-$N_b$'-X'X'X'-$n_p$'. 3□(IIc);
or

5□$n_q$'-$N_a$'-Z'Z'Z'-$N_b$'-Y'Y'Y'-$N_b$'-X'X'X'-$N_a$'-

$n_p$'. 3□(IId).

When the antisense strand is represented by formula (IIb), $N_b$' represents an oligonucleotide sequence comprising 0-10, 0-7, 0-5, 0-4, 0-2 or 0 modified nucleotides. Each $N_a$' independently represents an oligonucleotide sequence comprising 2-20, 2-15, or 2-10 modified nucleotides.

When the antisense strand is represented as formula (IIc), $N_b$' represents an oligonucleotide sequence comprising 0-10, 0-7, 0-5, 0-4, 0-2 or 0 modified nucleotides. Each $N_a$' independently represents an oligonucleotide sequence comprising 2-20, 2-15, or 2-10 modified nucleotides.

When the antisense strand is represented as formula (IId), each $N_b$' independently represents an oligonucleotide sequence comprising 0-10, 0-7, 0-5, 0-4, 0-2 or 0 modified nucleotides. Each $N_a$' independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

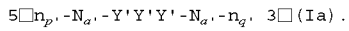

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an anti sense strand, each strand having 14 to 30 nucleotides, the RNAi duplex represented by formula (III):

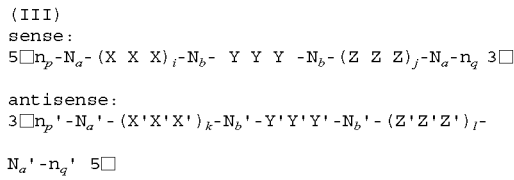

wherein:
j, k, and l are each independently 0 or 1;
p, p', q, and q' are each independently 0-6;
each $N_a$ and $N_a'$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;

wherein
each $n_p'$, $n_p$, $n_q'$, and $n_q$, each of which may or may not be present, independently represents an overhang nucleotide; and
XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

(IIIa)

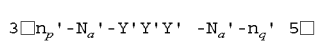

(IIIb)
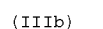
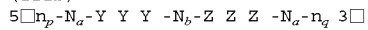

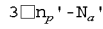

(IIIc)
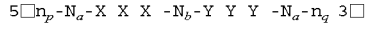

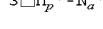

(IIId)
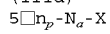

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (Mc), each $N_b$, $N_b'$ independently represents an oligonucleotide sequence comprising 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-5, 0-4, 0-2 or 0 modified nucleotides. Each $N_a$, $N_a'$ independently represents an oligonucleotide sequence comprising 2-20, 2-15, or 2-10 modified nucleotides. Each of $N_a$, $N_a'$, $N_b$ and $N_b'$, independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker. In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes ca target the same gene or two different genes; or each of the duplexes ca target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes ca target the same gene or two different genes; or each of the duplexes ca target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents ca target the same gene or two different genes; or each of the agents ca target same gene at two different target sites.

iRNA Conjugates

The iRNA agents disclosed herein can be in the form of conjugates. The conjugate may be attached at any suitable location in the iRNA molecule, e.g., at the 3' end or the 5' end of the sense or the antisense strand. The conjugates are optionally attached via a linker.

In some embodiments, an iRNA agent described herein is chemically linked to one or more ligands, moieties or conjugates, which may confer functionality, e.g., by affecting (e.g., enhancing) the activity, cellular distribution or cellular uptake of the iRNA. Such moieties include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In one embodiment, a ligand alters the distribution, targeting or lifetime of an iRNA agent into which it is incorporated. In some embodiments, a ligand provides an enhanced affinity for a selected target, e.g, molecule, cell or cell type, compartment, e.g., a cellular or organ compartment, tissue, organ or region of the body, as, e.g., compared to a species absent such a ligand. Typical ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an α helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, or an RGD peptide or RGD peptide mimetic.

In some embodiments, the ligand is a GalNAc ligand that comprises one or more N-acetylgalactosamine (GalNAc) derivatives. Additional description of GalNAc ligands is provided in the section titled Carbohydrate Conjugates.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g, cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

Lipid Conjugates

In one embodiment, the ligand is a lipid or lipid-based molecule. Such a lipid or lipid-based molecule can typically bind a serum protein, such as human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, neproxin or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control (e.g., inhibit) the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In one embodiment, the lipid based ligand binds HSA. For example, the ligand can bind HSA with a sufficient affinity such that distribution of the conjugate to a non-kidney tissue is enhanced. However, the affinity is typically not so strong that the HSA-ligand binding cannot be reversed.

In another embodiment, the lipid based ligand binds HSA weakly or not at all, such that distribution of the conjugate to the kidney is enhanced. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by cancer cells. Also included are HSA and low density lipoprotein (LDL).

Cell Permeation Agents

In another aspect, the ligand is a cell-permeation agent, such as a helical cell-permeation agent. In one embodiment, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is typically an α-helical agent, and can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 1). An RFGF analogue (e.g., amino acid sequence AALLPVLLAAP (SEQ ID NO: 2)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 3)) and the *Drosophila* Antennapedia protein (RQIKIWFQNRRMKWKK (SEQ ID NO: 4)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Typically, the peptide or peptidomimetic tethered to a dsRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

An RGD peptide moiety can be used to target a particular cell type, e.g., a tumor cell, such as an endothelial tumor cell or a breast cancer tumor cell (Zitzmann et al., Cancer Res., 62:5139-43, 2002). An RGD peptide can facilitate targeting of an dsRNA agent to tumors of a variety of other tissues, including the lung, kidney, spleen, or liver (Aoki et al., Cancer Gene Therapy 8:783-787, 2001). Typically, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001).

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars; di- and trisaccharides include sugars having two or three monosaccharide units (e.g., C5, C6, C7, or C8).

In one embodiment, a carbohydrate conjugate comprises a monosaccharide. In one embodiment, the monosaccharide is an N-acetylgalactosamine (GalNAc). GalNAc conjugates are described, for example, in U.S. Pat. No. 8,106,022, the entire content of which is hereby incorporated herein by reference. In some embodiments, the GalNAc conjugate serves as a ligand that targets the iRNA to particular cells. In some embodiments, the GalNAc conjugate targets the iRNA to liver cells, e.g., by serving as a ligand for the asialoglycoprotein receptor of liver cells (e.g., hepatocytes).

In some embodiments, the carbohydrate conjugate comprises one or more GalNAc derivatives. The GalNAc derivatives may be attached via a linker, e.g., a bivalent or trivalent branched linker. In some embodiments the GalNAc conjugate is conjugated to the 3' end of the sense strand. In some embodiments, the GalNAc conjugate is conjugated to the iRNA agent (e.g., to the 3' end of the sense strand) via a linker, e.g., a linker as described herein.

In some embodiments, the GalNAc conjugate is

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylal-

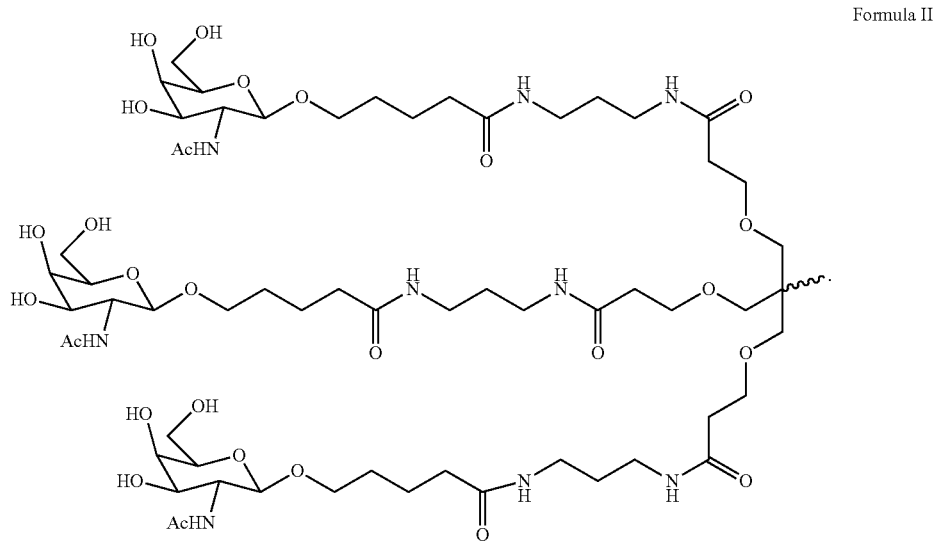 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

Formula II

In some embodiments, the RNAi agent is conjugated to L96 as defined in Table 2 and shown below kynyl, alkynylarylalkyl, alkynylarylalkenyl, alkynylarylalkynyl, alkylheteroarylalkyl, alkylheteroarylalkenyl,

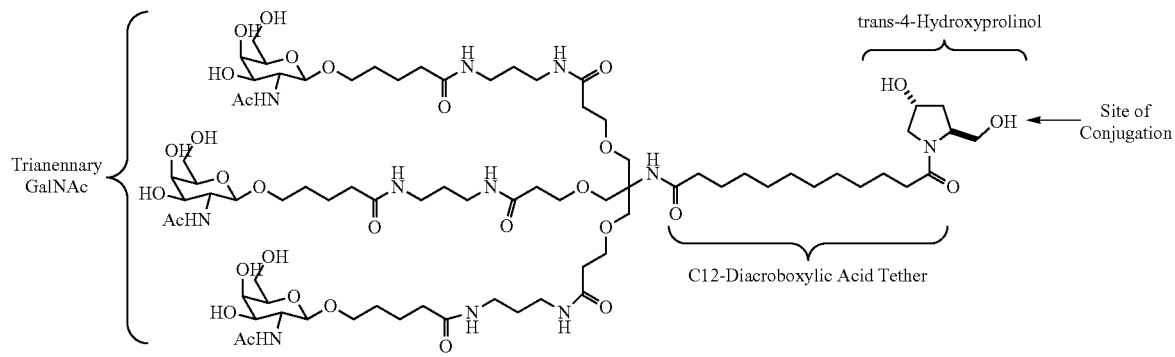

In some embodiments, the carbohydrate conjugate further comprises one or more additional ligands as described above, such as, but not limited to, a PK modulator and/or a cell permeation peptide.

In one embodiment, an iRNA of the invention is conjugated to a carbohydrate through a linker.

Linkers

In some embodiments, the conjugate or ligand described herein can be attached to an iRNA oligonucleotide with various linkers that can be cleavable or non-cleavable.

alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

In one embodiment, a dsRNA of the invention is conjugated to a bivalent or trivalent branched linker selected from the group of structures shown in any of formula (XXXI)-(XXXIV):

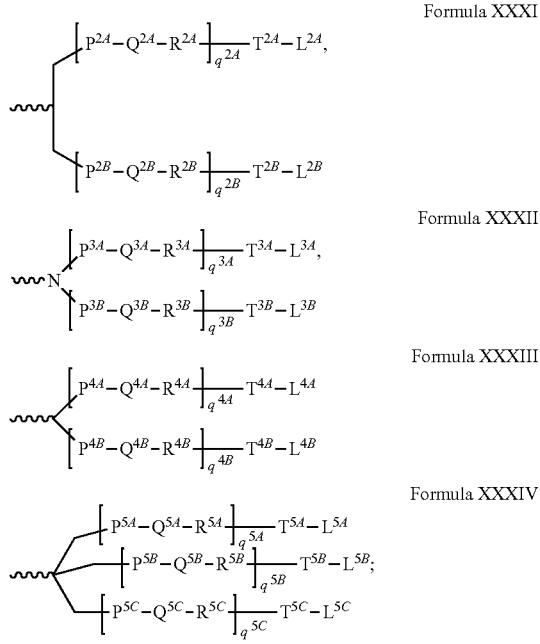

Formula XXXI

Formula XXXII

Formula XXXIII

Formula XXXIV wherein:
q2A, q2B, q3A, q3B, q4A, q4B, q5A, q5B and q5C represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, $C(R')=C(R'')$, $C\equiv C$ or C(O);
$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—O,

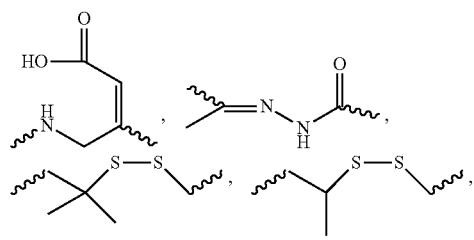

or heterocyclyl;
$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain. Trivalent conjugating GalNAc derivatives are particularly useful for use with RNAi agents for inhibiting the expression of a target gene, such as those of formula (XXXV):

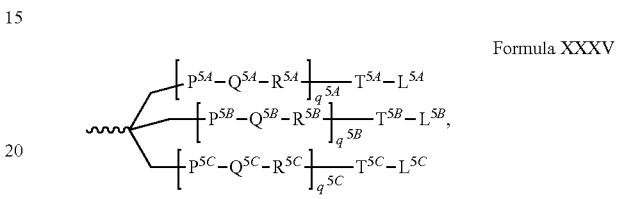

Formula XXXV wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Cleavable Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleavable Linking Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above.

Representative U.S. patents that teach the preparation of RNA conjugates include, but are not limited to, U.S. Pat. Nos. 4,828,979; 4,948,882; 5,218,105; 5,525,465; 5,541, 313; 5,545,730; 5,552,538; 5,578,717; 5,580,731; 5,591, 584; 5,109,124; 5,118,802; 5,138,045; 5,414,077; 5,486, 603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which is herein incorporated by reference.

It is not necessary for all positions in a given compound to be uniformly modified, and in fact more than one of the aforementioned modifications may be incorporated in a single compound or even at a single nucleoside within an iRNA. The present invention also includes iRNA compounds that are chimeric compounds.

"Chimeric" iRNA compounds, or "chimeras," in the context of the present invention, are iRNA compounds, e.g., dsRNAs, that contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., Biochem. Biophys. Res. Comm., 2007, 365(1):54-61; Letsinger et al., Proc. Natl. Acad. Sci. USA, 1989, 86:6553), cholic acid (Manoharan et al., Bioorg. Med. Chem. Lett., 1994, 4:1053), a thioether, e.g., hexyl-S-tritylthiol (Manoharan et al., Ann. N.Y. Acad. Sci., 1992, 660:306; Manoharan et al., Bioorg. Med. Chem. Let., 1993, 3:2765), a thiocholesterol (Oberhauser et al., Nucl. Acids Res., 1992, 20:533), an aliphatic chain, e.g., dodecandiol or undecyl residues (Saison-Behmoaras et al., EMBO J., 1991, 10:111; Kabanov et al., FEBS Lett., 1990, 259:327; Svinarchuk et al., Biochimie, 1993, 75:49), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nucleotides, 1995, 14:969), or adamantane acetic acid (Manoharan et al., Tetrahedron Lett., 1995, 36:3651), a palmityl moiety (Mishra et al., Biochim. Biophys. Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction may be performed either with the RNA still bound to the solid support or following cleavage of the RNA, in solution phase. Purification of the RNA conjugate by HPLC typically affords the pure conjugate.

Delivery of Nucleic Acid Molecules (iRNA)

The delivery of an iRNA to a subject in need thereof can be achieved in a number of different ways. In vivo delivery can be performed directly by administering a composition comprising an iRNA, e.g. a dsRNA, to a subject. Alternatively, delivery can be performed indirectly by administering one or more vectors that encode and direct the expression of the iRNA. These alternatives are discussed further below.

Direct Delivery

In general, any method of delivering a nucleic acid molecule can be adapted for use with an iRNA (see e.g., Akhtar S. and Julian R L. (1992) Trends Cell. Biol. 2(5): 139-144 and WO94/02595, which are incorporated herein by reference in their entireties). However, there are three factors that are important to consider in order to successfully deliver an iRNA molecule in vivo: (a) biological stability of the delivered molecule, (2) preventing non-specific effects, and (3) accumulation of the delivered molecule in the target tissue. The non-specific effects of an iRNA can be minimized by local administration, for example by direct injection or implantation into a tissue (as a non-limiting example, a tumor) or topically administering the preparation. Local administration to a treatment site maximizes local concentration of the agent, limits the exposure of the agent to systemic tissues that may otherwise be harmed by the agent or that may degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) Retina 24:132-138) and subretinal injections in mice (Reich, S J., et al (2003) Mol. Vis. 9:210-216) were both shown to prevent neovascularization in an experimental model of age-related macular degeneration. In addition, direct intratumoral injection of a dsRNA in mice reduces tumor volume (Pille, J., et al (2005) Mol. Ther. 11:267-274) and can prolong survival of tumor-bearing mice (Kim, W J., et al (2006) Mol. Ther. 14:343-350; Li, S., et al (2007) Mol. Ther. 15:515-523). RNA interference has also shown success with local delivery to the CNS by direct injection (Dorn, G., et al. (2004) Nucleic Acids 32:e49; Tan, P H., et al (2005) Gene Ther. 12:59-66; Makimura, H., et al (2002) BMC Neurosci. 3:18; Shishkina, G T., et al (2004) Neuroscience 129:521-528; Thakker, E R., et al (2004) *Proc. Natl. Acad. Sci. U.S.A.* 101:17270-17275; Akaneya, Y., et al (2005) J. Neurophysiol. 93:594-602) and to the lungs by intranasal administration (Howard, K A., et al (2006) Mol. Ther. 14:476-484; Zhang, X., et al (2004) J. Biol. Chem. 279:10677-10684; Bitko, V., et al (2005) Nat. Med. 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo.

Modification of the RNA or the pharmaceutical carrier can also permit targeting of the iRNA composition to the target tissue and avoid undesirable off-target effects. iRNA molecules can be modified by chemical conjugation to other groups, e.g., a lipid or carbohydrate group as described herein. Such conjugates can be used to target iRNA to particular cells, e.g., liver cells, e.g., hepatocytes. For example, GalNAc conjugates or lipid (e.g., LNP) formulations can be used to target iRNA to particular cells, e.g., liver cells, e.g., hepatocytes.

Lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) Nature 432:173-178). Conjugation of an iRNA to an aptamer has been shown to inhibit tumor growth and mediate tumor regression in a mouse model of prostate cancer (McNamara, J O., et al (2006) Nat. Biotechnol. 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) Journal of Controlled Release 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) J. Mol. Biol 327:761-766; Verma, U N., et al (2003) Clin. Cancer Res. 9:1291-1300; Arnold, A S et al (2007) J. Hypertens. 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) Nature 441:111-114), cardiolipin (Chien, P Y., et al (2005) Cancer Gene Ther. 12:321-328; Pal, A., et al (2005) Int J. Oncol. 26:1087-1091), polyethyleneimine (Bonnet M E., et al (2008) Pharm. Res. August 16 Epub ahead of print; Aigner, A. (2006) J. Biomed. Biotechnol. 71659), Arg-Gly-Asp (RGD) peptides (Liu, S. (2006) Mol. Pharm. 3:472-487), and polyamidoamines (Tomalia, D A., et al (2007) Biochem. Soc. Trans. 35:61-67; Yoo, H., et al (1999) Pharm. Res. 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

Vector Encoded iRNAs

In another aspect, iRNA targeting the target gene can be expressed from transcription units inserted into DNA or RNA vectors (see, e.g., Couture, A, et al., TIG. (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as an inverted repeat joined by a linker polynucleotide sequence such that the dsRNA has a stem and loop structure.

An iRNA expression vector is typically a DNA plasmid or viral vector. An expression vector compatible with eukaryotic cells, e.g., with vertebrate cells, can be used to produce recombinant constructs for the expression of an iRNA as described herein. Eukaryotic cell expression vectors are well known in the art and are available from a number of commercial sources. Typically, such vectors contain convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

An iRNA expression plasmid can be transfected into a target cell as a complex with a cationic lipid carrier (e.g., Oligofectamine) or a non-cationic lipid-based carrier (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct may be incorporated into vectors capable of episomal replication, e.g EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, FASEB J. 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-β-D1-thiogalactopyranoside (IPTG). A person skilled in the art would be able to choose the appropriate regulatory/promoter sequence based on the intended use of the iRNA transgene.

In a specific embodiment, viral vectors that contain nucleic acid sequences encoding an iRNA can be used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding an iRNA are cloned into one or more vectors, which facilitates delivery of the nucleic acid into a patient. More detail about retroviral vectors can be found, for example, in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Use of Adeno-associated virus (AAV) vectors is also contemplated (Walsh et al., Proc. Soc. Exp. Biol. Med. 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), J. Virol. 61: 3096-3101; Fisher K J et al. (1996), J. Virol, 70: 520-532; Samulski R et al. (1989), J. Virol. 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another typical viral vector is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), J Virol 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.
Pharmaceutical Compositions Containing Nucleic Acid Molecules (iRNA)

In one embodiment, the invention provides pharmaceutical compositions containing an iRNA, as described herein, and a pharmaceutically acceptable carrier. The pharmaceutical composition containing the iRNA is useful for treating a disease or disorder related to the expression or activity of a target gene. Such pharmaceutical compositions are formulated based on the mode of delivery. For example, compositions can be formulated for systemic administration via parenteral delivery, e.g., by intravenous (IV) delivery. In some embodiments, a composition provided herein (e.g., an LNP formulation) is formulated for intravenous delivery. In some embodiments, a composition provided herein (e.g., a composition comprising a GalNAc conjugate) is formulated for subcutaneous delivery.

The pharmaceutical compositions featured herein are administered in a dosage sufficient to inhibit expression of a target gene. In general, a suitable dose of iRNA will be in the range of 0.01 to 200.0 milligrams per kilogram body weight of the recipient per day, generally in the range of 1 to 50 mg per kilogram body weight per day. For example, the dsRNA can be administered at 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily, or the iRNA may be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period.

Sustained release formulations are well known in the art and are particularly useful for delivery of agents at a particular site, such as can be used with the agents of the present invention. In this embodiment, the dosage unit contains a corresponding multiple of the daily dose.

The effect of a single dose on target gene levels can be long lasting, such that subsequent doses are administered at not more than 3, 4, or 5 day intervals, or at not more than 1, 2, 3, or 4 week intervals.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as pathological processes related to target gene expression. Such models can be used for in vivo testing of iRNA, as well as for determining a therapeutically effective dose and/or an effective dosing regimen.

A suitable mouse model is, for example, a mouse containing a transgene expressing human target gene. Mice that have knock-in mutations can be used to determine the therapeutically effective dosage and/or duration of administration of target gene siRNA. The present invention also includes pharmaceutical compositions and formulations that include the iRNA compounds featured in the invention. The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as a tissue that produces erythrocytes. For example, the iRNA can be delivered to bone marrow, liver (e.g., hepatocytes of liver), lymph glands, spleen, lungs (e.g., pleura of lungs) or spine. In one embodiment, the iRNA is delivered to bone marrow.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention may be encapsulated within liposomes or may form complexes thereto, in particular to cationic liposomes. Alternatively, iRNAs may be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof. Topical formulations are described in detail in U.S. Pat. No. 6,747,014, which is incorporated herein by reference.

Liposomal Formulations

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to traverse intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in Pharmaceutical Dosage Forms, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., Biochem. Biophys. Res. Commun., 1987, 147, 980-985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., Journal of Controlled Release, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g., as a solution or as an emulsion) were ineffective (Weiner et al., Journal of Drug Targeting, 1992, 2, 405-410). Further, an additional study tested the efficacy of interferon administered as part of a liposomal formulation to the administration of interferon using an aqueous system, and concluded that the liposomal formulation was superior to aqueous administration (du Plessis et al., Antiviral Research, 1992, 18, 259-265).

Non-ionic liposomal systems have also been examined to determine their utility in the delivery of drugs to the skin, in particular systems comprising non-ionic surfactant and cholesterol. Non-ionic liposomal formulations comprising Novasome® I (glyceryl dilaurate/cholesterol/polyoxyethylene-10-stearyl ether) and Novasome® II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. S.T.P. Pharma. Sci., 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside Gm', or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., FEBS Letters, 1987, 223, 42; Wu et al., Cancer Research, 1993, 53, 3765).

Various liposomes comprising one or more glycolipids are known in the art. Papahadjopoulos et al. (Ann. N.Y. Acad. Sci., 1987, 507, 64) reported the ability of monosialoganglioside Gm', galactocerebroside sulfate and phosphatidylinositol to improve blood half-lives of liposomes. These findings were expounded upon by Gabizon et al. (Proc. Natl. Acad. Sci. U.S.A., 1988, 85, 6949). U.S. Pat. No. 4,837,028 and WO 88/04924, both to Allen et al., disclose liposomes comprising (1) sphingomyelin and (2) the ganglioside Gm' or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

Many liposomes comprising lipids derivatized with one or more hydrophilic polymers, and methods of preparation thereof, are known in the art. Sunamoto et al. (Bull. Chem. Soc. Jpn., 1980, 53, 2778) described liposomes comprising a nonionic detergent, $2C_{1215G}$, that contains a PEG moiety. Illum et al. (FEBS Lett., 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (FEBS Lett., 1990, 268, 235) described experiments demonstrating that liposomes comprising phosphatidylethanolamine (PE) derivatized with PEG or PEG stearate have significant increases in blood circulation half-lives. Blume et al. (Biochimica et Biophysica Acta, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1-20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include a dsRNA. U.S. Pat.

No. 5,665,710 to Rahman et al. describes certain methods of encapsulating oligodeoxynucleotides in liposomes. WO 97/04787 to Love et al. discloses liposomes comprising dsRNAs targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

Nucleic Acid Lipid Particles

In one embodiment, a target gene dsRNA is fully encapsulated in the lipid formulation, e.g., to form a SPLP, pSPLP, SNALP, or other nucleic acid-lipid particle. As used herein, the term "SNALP" refers to a stable nucleic acid-lipid particle, including SPLP. As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethylaminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1=(2-(4-(2-((2-(bis (2-hydroxydodecyl)amino)ethyl)(2-hydroxydodecyl)amino) ethyl)piperazin-1-yl)ethylazanediyl)didodecan-2-ol (Tech G1), or a mixture thereof. The cationic lipid may comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid may be from about 5 mol % to about 90 mol %, about 10 mol %, or about 58 mol % if cholesterol is included, of the total lipid present in the particle.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In some embodiments, the iRNA is formulated in a lipid nanoparticle (LNP).

LNP01

In one embodiment, the lipidoid ND98·4HCl (MW 1487) (see U.S. patent application Ser. No. 12/056,230, filed Mar. 26, 2008, which is herein incorporated by reference), Cholesterol (Sigma-Aldrich), and PEG-Ceramide C16 (Avanti Polar Lipids) can be used to prepare lipid-dsRNA nanoparticles (e.g., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

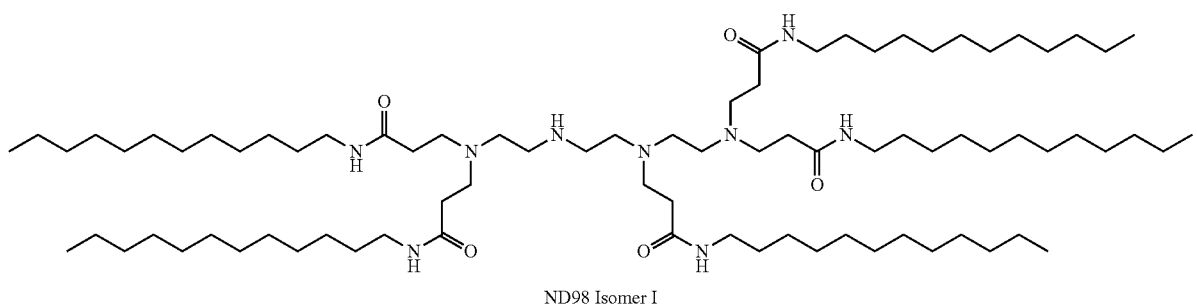

ND98 Isomer I

LNP01 formulations are described, e.g., in International Application Publication No. WO 2008/042973, which is hereby incorporated by reference.

Additional exemplary lipid-dsRNA formulations are provided in the following table.

TABLE 1

Examplary lipid formulations

| | Cationic Lipid | cationic lipid/non-cationic lipid/cholesterol/PEG-lipid conjugate Lipid:siRNA ratio |
|---|---|---|
| SNALP | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |
| S-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200) | C12-200/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |

TABLE 1-continued

Examplary lipid formulations

| Cationic Lipid | | cationic lipid/non-cationic lipid/cholesterol/PEG-lipid conjugate Lipid:siRNA ratio |
|---|---|---|
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. W02009/127060, filed Apr. 15, 2009, which is hereby incorporated by reference.
XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.
MC3 comprising formulations are described, e.g., in U.S. Provisional Ser. No. 61/244,834, filed Sep. 22, 2009, U.S. Provisional Ser. No. 61/185,800, filed Jun. 10, 2009, and International Application No. PCT/US10/28224, filed Jun. 10, 2010, which are hereby incorporated by reference.
ALNY-100 comprising formulations are described, e.g., International patent application number PCT/US09/63933, filed on Nov. 10, 2009, which is hereby incorporated by reference.
C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Cationic Lipids

Any of the compounds, e.g., cationic lipids and the like, used in the nucleic acid-lipid particles featured in the invention may be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —OR$^x$, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$, wherein n is 0, 1 or 2, R$^x$ and R$^y$ are the same or different and independently hydrogen, alkyl or heterocycle, and each of said alkyl and heterocycle substituents may be further substituted with one or more of oxo, halogen, —OH, —CN, alkyl, —OR', heterocycle, —NR$^x$R$^y$, —NR$^x$C(=O)R$^y$, —NR$^x$SO$_2$R$^y$, —C(=O)R$^x$, —C(=O)OR$^x$, —C(=O)NR$^x$R$^y$, —SO$_n$R$^x$ and —SO$_n$NR$^x$R$^y$.

"Halogen" means fluoro, chloro, bromo and iodo.

In some embodiments, the methods featured in the invention may require the use of protecting groups. Protecting group methodology is well known to those skilled in the art (see, for example, PROTECTIVE GROUPS IN ORGANIC SYNTHESIS, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In one embodiments, nucleic acid-lipid particles featured in the invention are formulated using a cationic lipid of formula A:

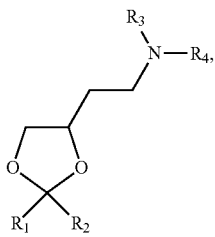

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above may be made by the following Reaction Schemes 1 or 2, wherein all substituents are as defined above unless indicated otherwise.

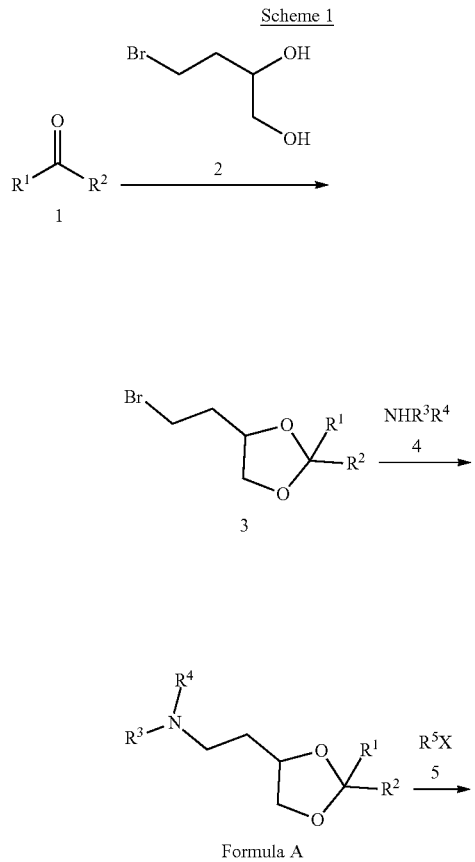

Lipid A, where $R_1$ and $R_2$ are independently alkyl, alkenyl or alkynyl, each can be optionally substituted, and $R_3$ and $R_4$ are independently lower alkyl or $R_3$ and $R_4$ can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

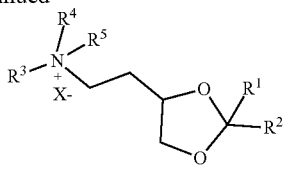

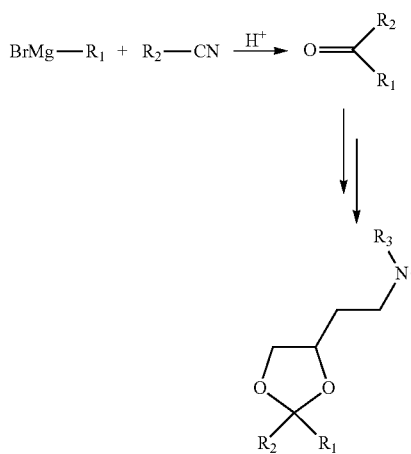

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e (6Z,9Z,28Z,31Z)-heptatriaconta-6,9,28,31-tetraen-19-yl 4-(dimethylamino)butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100
Synthesis of ketal 519 [ALNY-100] was performed using the following scheme 3:

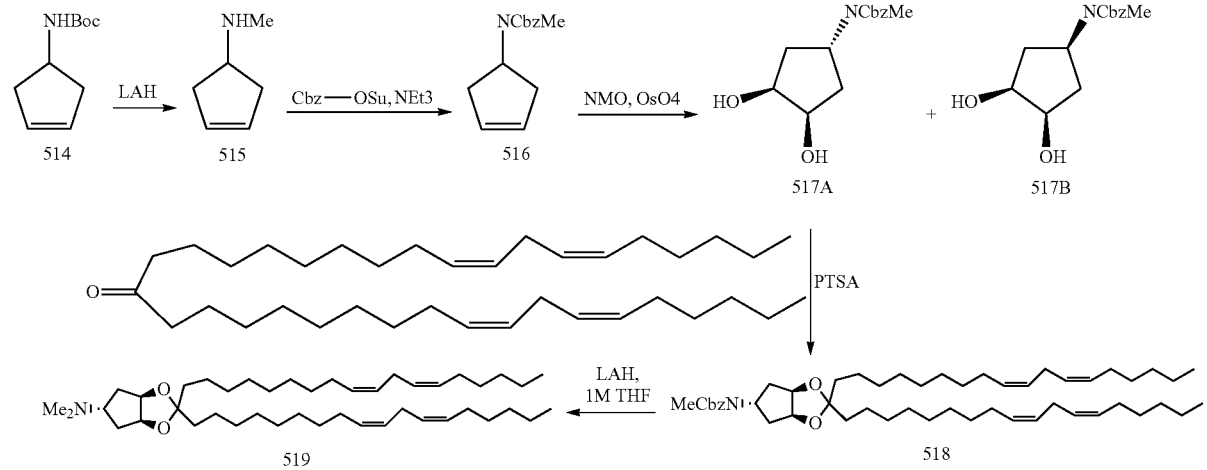

Synthesis of 515:
To a stirred suspension of LiAlH4 (3.74 g, 0.09852 mol) in 200 ml anhydrous THF in a two neck RBF (1 L), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): δ=9.34 (broad, 2H), 5.68 (s, 2H), 3.74 (m, 1H), 2.66-2.60 (m, 2H), 2.50-2.45 (m, 5H).

Synthesis of 516:
To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): δ=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H] −232.3 (96.94%).

Synthesis of 517A and 517B:
The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (1x 50 mL). Organic phase was dried over an·Na2SO4 and solvent was removed in vacuum. Silica gel column chromatographic purification of the crude material was afforded a mixture of diastereomers, which were separated by prep HPLC. Yield:—6 g crude 517A—Peak-1 (white solid), 5.13 g (96%). 1H-NMR (DMSO, 400 MHz): δ=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS—[M+H] −266.3, [M+NH4+] −283.5 present, HPLC—97.86%. Stereochemistry confirmed by X-ray.

Synthesis of 518:
Using a procedure analogous to that described for the synthesis of compound 505, compound 518 (1.2 g, 41%) was obtained as a colorless oil. 1H-NMR (CDCl3, 400 MHz): δ=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519:
A solution of compound 518 (1 eq) in hexane (15 mL) was added in a drop-wise fashion to an ice-cold solution of LAH in THF (1 M, 2 eq). After complete addition, the mixture was heated at 40° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. In some embodiments, oral formulations are those in which dsRNAs featured in the invention are administered in conjunction with one or more penetration enhancers surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention may be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly (ethylcyanoacrylate), poly(butylcyanoacrylate), poly (isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations featured in the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions featured in the present invention may be formulated into any of many possible dosage forms such as, but not limited to, tablets, capsules, gel capsules, liquid syrups, soft gels, suppositories, and enemas. The compositions may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Additional Formulations

Emulsions

The compositions of the present invention may be prepared and formulated as emulsions. Emulsions are typically heterogeneous systems of one liquid dispersed in another in the form of droplets usually exceeding 0.1 μm in diameter (see e.g., Ansel Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington Pharmaceutical Sciences, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (see e.g., Ansel Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel Pharmaceutical Dosage Forms and Drug Delivery Systems, Allen, L V., Popovich N G., and Ansel H C., 2004, Lippincott Williams & Wilkins (8th ed.), New York, NY; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (see e.g., Ansel Pharmaceutical Dosage Forms and Drug Delivery Systems, Allen, L V., Popovich N G., and Ansel H C., 2004, Lippincott Williams & Wilkins (8th ed.), New York, NY Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials is also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel Pharmaceutical Dosage Forms and Drug Delivery Systems, Allen, L V., Popovich N G., and Ansel H C., 2004, Lippincott Williams & Wilkins (8th ed.), New York, NY; Idson, in Pharmaceutical Dosage Forms, Lieberman, Rieger and Banker (Eds.), 1988, Marcel Dekker, Inc., New York, NY, volume 1, p. 199). Emulsion formulations for oral delivery have been very widely used because of ease of formulation, as well as efficacy from an absorption and bioavailability standpoint (see e.g., Ansel Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of iRNAs and nucleic acids are formulated as microemulsions. A microemulsion may be defined as a system of water, oil and amphiphile which is a single optically isotropic and thermodynamically stable liquid solution (see e.g., Ansel Pharmaceutical Dosage Forms and Drug Delivery Systems, Allen, L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel Pharmaceutical Dosage Forms and Drug Delivery Systems, Allen, L V., Popovich N G., and Ansel H C., 2004, Lippincott Williams & Wilkins (8th ed.), New York, NY; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (M0310), hexaglycerol monooleate (P0310), hexaglycerol pentaoleate (P0500), decaglycerol monocaprate (MCA750), decaglycerol monooleate (M0750), decaglycerol sequioleate (S0750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions may form spontaneously when their components are brought together at ambient temperature. This may be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention may also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, NY, 2002; Lee et al., Critical Reviews in Therapeutic Drug Carrier Systems, 1991, p. 92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, NY, 2002; Lee et al., Critical Reviews in Therapeutic Drug Carrier Systems, 1991, p. 92); and perfluorochemical emulsions, such as FC-43. Takahashi et al., J. Pharm. Pharmacol., 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, MA, 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., J. Pharm. Pharmacol., 1992, 44, 651-654).

Bile salts: The physiological role of bile includes the facilitation of dispersion and absorption of lipids and fat-soluble vitamins (see e.g., Malmsten, M. Surfactants and polymers in drug delivery, Informa Health Care, New York, NY, 2002; Brunton, Chapter 38 in: Goodman & Gilman § The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, NY, 2002; Lee et al., Critical Reviews in Therapeutic Drug Carrier Systems, 1991, page 92; Swinyard, Chapter 39 In: Remington Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating Agents: Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of β-diketones (enamines)(see e.g., Katdare, A. et al., Excipient development for pharmaceutical, biotechnology, and drug delivery, CRC Press, Danvers, MA, 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

Non-chelating non-surfactants: As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers include, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, CA), Lipofectamine 2000™ (Invitrogen; Carlsbad, CA), 293Fectin™ (Invitrogen; Carlsbad, CA), Cellfectin™ (Invitrogen; Carlsbad, CA), DMRIE-C™ (Invitrogen; Carlsbad, CA), FreeStyle™ MAX (Invitrogen; Carlsbad, CA), Lipofectamine™ 2000 CD (Invitrogen; Carlsbad, CA), Lipofectamine™ (Invitrogen; Carlsbad, CA), RNAiMAX (Invitrogen; Carlsbad, CA), Oligofectamine™ (Invitrogen; Carlsbad, CA), Optifect™ (Invitrogen; Carlsbad, CA), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, WI), TransFast™ Transfection Reagent (Promega; Madison, WI), Tfx™-20 Reagent (Promega; Madison, WI), Tfx™-50 Reagent (Promega; Madison, WI), DreamFect™ (OZ Biosciences; Marseille, France), EcoTransfect (OZ Biosciences; Marseille, France), TransPass' D1 Transfection Reagent (New England Biolabs; Ipswich, MA, USA), LyoVec™/LipoGen™ (Invivogen; San Diego, CA, USA), PerFectin Transfection Reagent (Genlantis; San Diego, CA, USA), NeuroPORTER Transfection Reagent (Genlantis; San Diego, CA, USA), GenePORTER Transfection reagent (Genlantis; San Diego, CA, USA), GenePORTER 2 Transfection reagent (Genlantis; San Diego, CA, USA), Cytofectin Transfection Reagent (Genlantis; San Diego, CA, USA), BaculoPORTER Transfection Reagent (Genlantis; San Diego, CA, USA), TroganPORTER™ transfection Reagent (Genlantis; San Diego, CA, USA), RiboFect (Bioline; Taunton, MA, USA), PlasFect (Bioline; Taunton, MA, USA), UniFECTOR (B-Bridge International; Mountain View, CA, USA), SureFECTOR (B-Bridge International; Mountain View, CA, USA), or HiFect™ (B-Bridge International, Mountain View, CA, USA), among others.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4$'$ othiocyano-stilbene-2,2$'$ disulfonic acid (Miyao et al., DsRNA Res. Dev., 1995, 5, 115-121; Takakura et al., DsRNA & Nucl. Acid Drug Dev., 1996, 6, 177-183.

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances that increase the viscosity of the suspension including, for example, sodium carboxymethylcellulose, sorbitol and/or dextran. The suspension may also contain stabilizers.

In some embodiments, pharmaceutical compositions featured in the invention include (a) one or more iRNA compounds and (b) one or more biologic agents which function by a non-RNAi mechanism. Examples of such biologic agents include agents that interfere with an interaction of target gene and at least one target gene binding partner.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are typical.

The data obtained from cell culture assays and animal studies can be used in formulating a range of dosage for use in humans. The dosage of compositions featured in the invention lies generally within a range of circulating concentrations that include the ED50 with little or no toxicity. The dosage may vary within this range depending upon the dosage form employed and the route of administration utilized. For any compound used in the methods featured in the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans.

Levels in plasma may be measured, for example, by high performance liquid chromatography.

In addition to their administration, as discussed above, the iRNAs featured in the invention can be administered in combination with other known agents effective in treatment of diseases or disorders related to target gene expression. In any event, the administering physician can adjust the amount and timing of iRNA administration on the basis of results observed using standard measures of efficacy known in the art or described herein.

Methods for Modulating Expression of a Target Gene

In yet another aspect, the invention provides a method for modulating (e.g., inhibiting or activating) the expression of a target gene, e.g., in a cell or in a subject. In some embodiments, the cell is ex vivo, in vitro, or in vivo. In some embodiments, the cell is an erythroid cell or a hepatocyte. In some embodiments, the cell is in a subject (e.g., a mammal, such as, for example, a human). In some embodiments, the subject (e.g., the human) is at risk, or is diagnosed with a disease related to target gene expression, as described above.

In one embodiment, the method includes contacting the cell with an iRNA as described herein, in an amount effective to decrease the expression of a target gene in the cell. "Contacting," as used herein, includes directly contacting a cell, as well as indirectly contacting a cell. For example, a cell within a subject (e.g., an erythroid cell or a liver cell, such as a hepatocyte) may be contacted when a composition comprising an iRNA is administered (e.g., intravenously or subcutaneously) to the subject.

The expression of a target gene may be assessed based on the level of expression of a target gene mRNA, a target gene protein, or the level of a parameter functionally linked to the level of expression of a target gene. In some embodiments, the expression of target gene is inhibited by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the iRNA has an $IC_{50}$ in the range of 0.001-0.01 nM, 0.001-0.10 nM, 0.001-1.0 nM, 0.001-10 nM, 0.01-0.05 nM, 0.01-0.50 nM, 0.02-0.60 nM, 0.01-1.0 nM, 0.01-1.5 nM, 0.01-10 nM. The $IC_{50}$ value may be normalized relative to an appropriate control value, e.g., the $IC_{50}$ of a non-targeting iRNA.

In some embodiments, the method includes introducing into the cell an iRNA as described herein and maintaining the cell for a time sufficient to obtain degradation of the mRNA transcript of a target gene, thereby inhibiting the expression of the target gene in the cell.

In one embodiment, the method includes administering a composition described herein, e.g., a composition comprising an iRNA that targets target gene, to the mammal such that expression of the target target gene is decreased, such as for an extended duration, e.g., at least two, three, four days or more, e.g., one week, two weeks, three weeks, or four weeks or longer. In some embodiments, the decrease in expression of target gene is detectable within 1 hour, 2 hours, 4 hours, 8 hours, 12 hours, or 24 hours of the first administration.

In another embodiment, the method includes administering a composition as described herein to a mammal such that expression of the target target gene is increased by e.g., at least 10% compared to an untreated animal. In some embodiments, the activation of target gene occurs over an extended duration, e.g., at least two, three, four days or more, e.g., one week, two weeks, three weeks, four weeks, or more. Without wishing to be bound by theory, an iRNA can activate target gene expression by stabilizing the target gene mRNA transcript, interacting with a promoter in the genome, and/or inhibiting an inhibitor of target gene expression.

The iRNAs useful for the methods and compositions featured in the invention specifically target RNAs (primary or processed) of a target gene. Compositions and methods for inhibiting the expression of a target gene using iRNAs can be prepared and performed as described elsewhere herein.

In one embodiment, the method includes administering a composition containing an iRNA, where the iRNA includes a nucleotide sequence that is complementary to at least a part of an RNA transcript of the target gene of the mammal to be treated. When the organism to be treated is a mammal such as a human, the composition may be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration.

In certain embodiments, the compositions are administered by intravenous infusion or injection. In some such embodiments, the compositions comprise a lipid formulated siRNA (e.g., an LNP formulation, such as an LNP11 formulation as described herein) for intravenous infusion.

In other embodiments, the compositions are administered subcutaneously. In some such embodiments, the compositions comprise an iRNA conjugated to a GalNAc ligand.

Target Genes and Methods for Treating Diseases Related to Expression of a Target Gene The dosing regimen and methods described herein can be used to inhibit target gene expression and/or to treat a disease, a disorder, or a pathological process that is related to target gene expression. In certain embodiments, the target genes is chosen from: Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, HAMP, Activated Protein C gene, Cyclin D gene, VEGF gene, antithrombin 3 gene, aminolevulinate synthase 1 gene, alpha-1-antitrypsin gene, tmprss6 gene, apoa1 gene, apoc3 gene, bc11a gene, klf gene, angptl3 gene, plk gene, PKN3 gene, HBV, HCV, p53 gene, angiopoietin gene, or angiopoietin-like 3 gene. In certain embodiments, the target is chosen from: Eg5, PCSK9, TTR, HAMP, VEGF gene, antithrombin 3 gene, aminolevulinate synthase 1 gene, alpha-1-antitrypsin gene, or tmprss6 gene.

TTR Target Gene

In one embodiment, the target gene is a TTR gene. Nucleic acid (e.g., RNA) molecules capable of reducing expression of a TTR gene (e.g., to reduce TTR amyloid deposition, or treating a TTR-mediated amyloidosis (ATTR)) are described in, e.g., WO 2011/056883, the contents of which are specifically incorporated by reference herein. In certain embodiments, the RNA molecule comprises an antisense strand comprising, or consisting of, 10, 15, 20, 25 or more contiguous nucleotides complementary to the transthyretin mRNA (e.g., wild type or mutant TTR mRNA e.g., V30M mutant TTR). In certain embodiments, the RNA molecule comprises an antisense strand comprising, or consisting of, 10, 15, 20, 25 or more contiguous nucleotides of an antisense oligonucleotide sequence disclosed in, e.g., WO 2011/056883, e.g., SEQ ID NOs: 170, 730, or 1010. In certain embodiments, the RNA molecule comprises an antisense strand comprising, or consisting of, 10, 15, 20, 25 or more contiguous nucleotides of an antisense oligonucleotide sequence disclosed in, e.g., WO 2011/056883, e.g., SEQ ID NOs: 170, 730, or 1010; and a sense strand disclosed in, e.g., WO 2011/056883, e.g., SEQ ID NOs: 169, 729, or 1009.

PCSK9 Target Gene

In one embodiment, the target gene is a PCSK9 gene. Nucleic acid (e.g., RNA) molecules capable of reducing expression of a PCSK9 gene (e.g., to treat a PCSK9-related disorder, e.g., lowering serum cholesterol) are described, e.g., in WO 2012/05869, WO 2011/005861, WO 2011/028938, WO 2010/148013, WO 2009/134487 and WO 2007/134161, the contents of which are specifically incorporated by reference herein. In certain embodiments, the RNA molecule comprises an antisense strand comprising 10, 15, 20, 25 or more contiguous nucleotides complementary to the PCSK9 mRNA (e.g., wild type or mutant PCSK9 mRNA). In certain embodiments, the RNA molecule comprises an antisense strand comprising, or consisting of, 10, 15, 20, 25 or more contiguous nucleotides of an antisense oligonucleotide sequence disclosed, e.g., in WO 2012/05869, WO 2011/005861, WO 2011/028938, WO 2010/148013, WO 2009/134487 and WO 2007/134161. In certain embodiments, the RNA molecule comprises an antisense strand comprising, or consisting of, 10, 15, 20, 25 or more contiguous nucleotides of an antisense oligonucleotide sequence disclosed, e.g., in WO 2012/05869, WO 2011/005861, WO 2011/028938, WO 2010/148013, WO 2009/134487 and WO 2007/134161; and a sense strand disclosed, e.g., in WO 2012/05869, WO 2011/005861, WO 2011/028938, WO 2010/148013, WO 2009/134487 and WO 2007/134161.

Eg5 Target Gene

In one embodiment, the target gene is an Eg5 gene. Nucleic acid (e.g., RNA) molecules capable of reducing expression of an Eg5 gene (e.g., to treat an Eg5-related disorder) are described, e.g., in WO 2011/034798, WO 2010/105209, WO 2009/111658, and WO 2007/115168, the contents of which are specifically incorporated by reference herein. In certain embodiments, the RNA molecule comprises an antisense strand comprising 10, 15, 20, 25 or more contiguous nucleotides complementary to the Eg5 mRNA (e.g., wild type or mutant Eg5 mRNA). In certain embodiments, the RNA molecule comprises an antisense strand comprising, or consisting of, 10, 15, 20, 25 or more contiguous nucleotides of an antisense oligonucleotide sequence disclosed, e.g., in WO 2011/034798, WO 2010/105209, WO 2009/111658, and WO 2007/115168. In certain embodiments, the RNA molecule comprises an antisense strand comprising, or consisting of, 10, 15, 20, 25 or more contiguous nucleotides of an antisense oligonucleotide sequence disclosed, e.g., in WO 2011/034798, WO 2010/105209, WO 2009/111658, and WO 2007/115168; and a sense strand disclosed, e.g., in WO 2011/034798, WO 2010/105209, WO 2009/111658, and WO 2007/115168.

VEGF Target Gene

In one embodiment, the target gene is a VEGF gene. Nucleic acid (e.g., RNA) molecules capable of reducing expression of a VEGF gene (e.g., to treat a VEGF-related disorder) are described, e.g., in WO 2011/034798, WO 2010/105209, WO 2009/111658, and WO 2005/089224, the contents of which are specifically incorporated by reference herein. In certain embodiments, the RNA molecule comprises an antisense strand comprising 10, 15, 20, 25 or more contiguous nucleotides complementary to the VEGF mRNA (e.g., wild type or mutant VEGF mRNA). In certain embodiments, the RNA molecule comprises an antisense strand comprising, or consisting of, 10, 15, 20, 25 or more contiguous nucleotides of an antisense oligonucleotide sequence disclosed, e.g., in WO 2011/034798, WO 2010/105209, WO 2009/111658, and WO 2005/089224. In certain embodiments, the RNA molecule comprises an antisense strand comprising, or consisting of, 10, 15, 20, 25 or more contiguous nucleotides of an antisense oligonucleotide sequence disclosed, e.g., in WO 2011/034798, WO 2010/105209, WO 2009/111658, and WO 2005/089224; and a sense strand disclosed, e.g., in WO 2011/034798, WO 2010/105209, WO 2009/111658, and WO 2005/089224.

HAMP Target Gene

In one embodiment, the target gene is a Hepcidin Antimicrobial Peptide (HAMP) gene. Nucleic acid (e.g., RNA) molecules capable of reducing expression of a HAMP gene (e.g., to treat a HAMP-related disorder, e.g., a microbial infection) are described, e.g., in WO 2008/036933 and WO 2012/177921, the contents of which are specifically incorporated by reference herein. In certain embodiments, the RNA molecule comprises an antisense strand comprising 10, 15, 20, 25 or more contiguous nucleotides complementary to the HAMP mRNA (e.g., wild type or mutant HAMP mRNA). In certain embodiments, the RNA molecule comprises an antisense strand comprising, or consisting of, 10, 15, 20, 25 or more contiguous nucleotides of an antisense oligonucleotide sequence disclosed, e.g., in WO 2008/036933 and WO 2012/177921. In certain embodiments, the RNA molecule comprises an antisense strand comprising, or consisting of, 10, 15, 20, 25 or more contiguous nucleotides of an antisense oligonucleotide sequence disclosed, e.g., in WO 2008/036933 and WO 2012/177921; and a sense strand disclosed, e.g., in WO 2008/036933 and WO 2012/177921.

TMPRSS6 Target Gene

In one embodiment, the target gene is a TMPRSS6 gene. Nucleic acid (e.g., RNA) molecules capable of reducing expression of a TMPRSS6 gene (e.g., to treat a TMPRSS6-related disorder) are described, e.g., in WO 2012/135246, the contents of which are specifically incorporated by reference herein. In certain embodiments, the RNA molecule comprises an antisense strand comprising 10, 15, 20, 25 or more contiguous nucleotides complementary to the TMPRSS6 mRNA (e.g., wild type or mutant TMPRSS6 mRNA). In certain embodiments, the RNA molecule comprises an antisense strand comprising, or consisting of, 10, 15, 20, 25 or more contiguous nucleotides of an antisense oligonucleotide sequence disclosed, e.g., in WO 2012/135246. In certain embodiments, the RNA molecule comprises an antisense strand comprising, or consisting of, 10, 15, 20, 25 or more contiguous nucleotides of an antisense oligonucleotide sequence disclosed, e.g., in WO 2012/135246; and a sense strand disclosed, e.g., in WO 2012/135246.

5'-Aminolevulinic Acid Synthase 1 (ALAS1) Gene

In one embodiment, the target gene is an ALAS1 gene. Nucleic acid (e.g., RNA) molecules capable of reducing expression of an ALAS1 gene (e.g., to treat an ALAS1-related disorder, e.g. a pathological processes involving porphyrins or defects in the porphyrin pathway, such as, for example, porphyrias) are described, e.g., in U.S. Ser. No. 13/835,613, filed on Mar. 15, 2013, the contents of which are specifically incorporated by reference herein. In certain embodiments, the RNA molecule comprises an antisense strand comprising 10, 15, 20, 25 or more contiguous nucleotides complementary to the ALAS1 mRNA (e.g., wild type or mutant ALAS1 mRNA). In certain embodiments, the RNA molecule comprises an antisense strand comprising, or consisting of, 10, 15, 20, 25 or more contiguous nucleotides of an antisense oligonucleotide sequence disclosed, e.g., in U.S. Ser. No. 13/835,613. In certain embodiments, the RNA molecule comprises an antisense strand comprising, or consisting of, 10, 15, 20, 25 or more contiguous nucleotides of an antisense oligonucleotide sequence disclosed, e.g., in U.S. Ser. No. 13/835,613; and a sense strand disclosed, e.g., in U.S. Ser. No. 13/835,613.

Complement Component 3 (C3) Gene

In one embodiment, the target gene is a Complement component 3 (C3) gene. Nucleic acid (e.g., RNA) molecules capable of reducing expression of a C3 gene (e.g., to treat a C3-related disorder. C3 plays a central role in the complement system and contributes to innate immunity. In humans it is encoded on chromosome 19 by a gene called C3. In certain embodiments, the RNA molecule comprises an antisense strand comprising 10, 15, 20, 25 or more contiguous nucleotides complementary to the C5 mRNA (e.g., wild type or mutant C3 mRNA).

Complement Component 5 (C5) Gene

In one embodiment, the target gene is a Complement component 5 (C5) gene. Nucleic acid (e.g., RNA) molecules capable of reducing expression of a C5 gene (e.g., to treat a C5-related disorder, e.g. a pathological processes involving inflammatory and cell killing processes. This protein is composed of alpha and beta polypeptide chains that are linked by a disulfide bridge. An activation peptide, C5a, which is an anaphylatoxin that possesses potent spasmogenic and chemotactic activity, is derived from the alpha polypeptide via cleavage with a convertase. In certain embodiments, the RNA molecule comprises an antisense strand comprising 10, 15, 20, 25 or more contiguous nucleotides complementary to the C5 mRNA (e.g., wild type or mutant C5 mRNA).

As used herein, "a disorder related to target gene expression," a "disease related to target gene expression, a "pathological process related to target gene expression," or the like includes any condition, disorder, or disease in which target gene expression is altered (e.g., elevated). For example, an iRNA targeting an ALAS1 target gene, or a combination thereof, may be used for treatment of conditions in which levels of a porphyrin or a porphyrin precursor (e.g., ALA or PBG) are elevated (e.g., certain porphyrias), or conditions in which there are defects in the enzymes of the heme biosynthetic pathway (e.g., certain porphyrias). Disorders related to target gene expression include, for example, X-linked sideroblastic anemia (XLSA), ALA deyhdratase deficiency porphyria (Doss porphyria), acute intermittent porphyria (AIP), congenital erythropoietic porphyria, prophyria cutanea tarda, hereditary coproporphyria (coproporphyria), variegate porphyria, erythropoietic protoporphyria (EPP), and transient erythroporphyria of infancy.

As used herein, a "subject" to be treated according to the methods described herein, includes a human or non-human animal, e.g., a mammal. The mammal may be, for example, a rodent (e.g., a rat or mouse), a porcine, or a primate (e.g., a monkey). In some embodiments, the subject is a human.

In some embodiments, the subject is suffering from a disorder related to target gene expression or is at risk of developing a disorder related to target gene expression.

In some embodiments, an iRNA targeting target gene is administered together with (e.g., before, after, or concurrent with) another treatment that may serve to alleviate one or more symptoms.

The term "decrease" (or "increase") is intended to refer to a measurable change, e.g., a statistically significant change. The change may be, for example, at least 5%, 10%, 20%, 30%, 40%, 50% or more change (e.g., decrease (or increase) relative to a reference value, e.g., a reference where no iRNA is provided).

The invention further relates to the use of an iRNA or a pharmaceutical composition thereof, e.g., for treating a disorder related to target gene expression, in combination with other pharmaceuticals and/or other therapeutic methods, e.g., with known pharmaceuticals and/or known therapeutic methods, such as, for example, those which are currently employed for treating the disorder.

The effective amount for the treatment of a disorder related to target gene expression depends on the type of disorder to be treated, the severity of the symptoms, the subject being treated, the sex, age and general condition of the subject, the mode of administration and so forth. For any given case, an appropriate "effective amount" can be determined by one of ordinary skill in the art using routine experimentation. It is within the ability of one skilled in the art to monitor efficacy of treatment or prevention by measuring any one of such parameters, or any combination of parameters. In connection with the administration of an iRNA targeting target gene or pharmaceutical composition thereof, "effective against" a disorder related to target gene expression indicates that administration in a clinically appropriate manner results in a beneficial effect, e.g., for an individual patient or for at least a fraction of patients, e.g., a statistically significant fraction of patients. Beneficial effects include, e.g., prevention of or reduction of symptoms or other effects. For example, beneficial effects include, e.g., an improvement (e.g., decrease in the severity or frequency) of symptoms, a reduction in the severity or frequency of attacks, a reduced risk of developing associated disease (e.g., neuropathy (e.g., progressive neuropathy), hepatocellular cancer), an improved ability to tolerate a precipitating factor, an improvement in quality of life, a reduction in the expression of target gene, a reduction in a level (e.g., a plasma or urine level) of a marker of a disease or other effect generally recognized as positive by medical doctors familiar with treating the particular type of disorder.

A treatment or preventive effect is evident when there is an improvement, e.g., a statistically significant improvement in one or more parameters of disease status, or by a failure to worsen or to develop symptoms where they would otherwise be anticipated. As an example, a favorable change of at least 10% in a measurable parameter of disease, e.g., at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed.

Patients can be administered a therapeutic amount of iRNA. The therapeutic amount can be, e.g., 0.01-50 mg/kg, 0.01-10 mg/kg, 0.01-5 mg/kg, 0.01-2 mg/kg, 0.01-1 mg/kg, and more typically, 0.01-0.5 mg, 0.1 to 0.3 mg/kg. For example, the therapeutic amount can be 0.05, 0.1, 0.2, 0.3, 0.4, 0.5, 0.6, 0.7, 0.8, 0.9, 1.0, 1.5, 2.0, or 2.5, 3.0, 3.5, 4.0, 4.5, 5, 10, 15, 20, 25, 30, 35, 40, 45, or 50 mg/kg dsRNA. Any of these dosages can be used in the dosage regimens and methods described herein.

In some embodiments, the iRNA is formulated as a lipid formulation, e.g., an LNP formulation as described herein. In some such embodiments, the therapeutic amount is 0.01-5 mg/kg, e.g., 0.01, 0.02, 0.03, 0.04, 0.05, 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 mg/kg dsRNA. Any of these dosages can be used in the dosage regimens and methods described herein.

In some embodiments, the lipid formulation, e.g., LNP formulation, is administered intravenously.

In some embodiments, the iRNA is administered by intravenous infusion over a period of time, such as over a 5-minute, 10-minute, 15-minute, 20-minute, 25-minute, 30-minute, 40-minute, 50-minute, 55-minute, 60-minute, 65-minute, or 70-minute period.

In some embodiments, the iRNA is in the form of a GalNAc conjugate as described herein. In some such embodiments, the therapeutic amount is 0.5-50 mg/kg, e.g., 0.5, 0.6, 0.7, 0.8, 0.9, 1.0, 1.5, 2.0, 2.5, 3.0, 3.5, 4.0, 4.5, 5.0, 6, 7, 8, 9, 10, 15, 20, 25, 30, 35, 40, 45, or 50 mg/kg dsRNA. In some embodiments, the GalNAc conjugate is administered subcutaneously. Any of these dosages can be used in the dosage regimens and methods described herein.

In some embodiments, the administration is repeated, for example, on a regular basis, such as, daily, biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer.

In some embodiments, the iRNA agent is administered in two or more doses (e.g., two or more doses as described herein). In some embodiments, the first and second doses are adjusted such as to decrease a hypersensitivity response. In other embodiments, the number or amount of subsequent doses is dependent on the achievement of a desired effect, e.g., suppression of a target gene, or the achievement of a therapeutic or prophylactic effect, e.g., reduction or prevention of one or more symptoms associated with a target gene disorder.

In some embodiments, the iRNA agent is administered according to a schedule. For example, the iRNA agent may be administered once per week, twice per week, three times per week, four times per week, or five times per week. In some embodiments, the schedule involves regularly spaced administrations, e.g., hourly, every four hours, every six hours, every eight hours, every twelve hours, daily, every 2 days, every 3 days, every 4 days, every 5 days, weekly, biweekly, or monthly.

In some embodiments, the predetermined reduction is a decrease of at least 10%, 20%, 30%, 40%, or 50% in target gene expression or symptoms (e.g., marker level).

In some embodiments, the predetermined reduction is a reduction of at least 1, 2, 3, or more standard deviations, wherein the standard deviation is determined based on the values from a reference sample, e.g., a reference sample as described herein.

Administration of the iRNA may reduce target gene mRNA or protein levels, e.g., in a cell, tissue, blood, urine or other compartment of the patient by at least 10%, at least 15%, at least 20%, at least 25%, at least 30%, at least 40%, at least 50%, at least 60%, at least 70%, at least 80% or at least 90% or more. Administration of the iRNA may reduce levels of products associated with target gene expression.

Before administration of a full dose of the iRNA, patients can be administered a smaller dose, such as a 5%, 8% or 10% infusion dose, and monitored for adverse effects, such as a hypersensivity or an allergic reaction, or for elevated lipid levels or blood pressure. In another example, the patient can be monitored for unwanted effects.

Hypersensitivity Reactions and Biomarker Detection

A hypersensitivity reaction may occur as the doses of the compositions described herein are increased (e.g., at a dose of about 300 µg/kg). In those embodiments of increased doses, the subject can be treated with the methods and dosage regiments described herein.

In some embodiments, the dosages and time periods of administration of the doses described herein are selected such that no substantial IRR and/or hypersensitivity reaction (e.g., a detectable IRR or hypersensitivity reaction) occurs in a subject. The hypersensitivity reaction can be an acute reaction. In some embodiments, the subject is a human. Alternatively, the subject can be an animal (e.g., an animal model for a complement or a hypersensitivity reaction (e.g., a porcine model as described herein and also in Szebeni et al. *Nanomedicine.* 2012 February; 8(2):176-84; Szebeni et al. *Adv Drug Deliv Rev.* 2011 Sep. 16; 63(12):1020-30 (2012); Szebeni et al. *Adv Drug Delivery Rev*)).

In some embodiments, the methods described herein do not cause a detectable hypersensitivity reaction, e.g., as measured by one or more of the assays or symptoms described herein. In embodiments, the method results in a decrease in the hypersensitivity reaction, which is less than 1%, 5%, 10%, 25%, 30%, 35% or 40%, e.g., as measured by one or more of of the assays or symptoms described herein. In certain embodiments, the changes described herein are compared to a reference parameter (e.g., a subject exposed to a bolus dose, or the subject prior to treatment).

In one embodiment, in response to the first and second dose regimen disclosed herein, the subject shows a reduced hypersensitivity reaction (e.g., a decreased hemodynamic change, relative to a reference parameter (e.g., a subject exposed to a bolus dose, or the subject prior to treatment).

In certain embodiments, the methods described herein cause a reduced hypersensitivity reaction, e.g., leading to a reduction (e.g., partial or complete reduction) in the administration of one or more of a steroid (e.g., dexamethasone or an equivalent), an analgesic (e.g., paracetamol), or a histamine receptor antagonist (e.g., an H1 or an H2 blocker). In other embodiments, the subject does not receive administration of a steroid (e.g., dexamethasone or an equivalent), within X hours of any of the initiation of administration of said first dose, wherein X is less than 1 hour, 2 hours, 3 hours, 5 hours, 10 hours, 15 hours, 24 hours or 48 hours.

Alternatively, or in combination, the subject may be medicated or premedicated with one or more of a steroid, a histamine blocker or acetaminophen. For example, prior to (30 to 60 minutes), during, or after administration of a dose as described herein (e.g., a first or second dose) of the compositions described herein, the subject can receive one or more ofL a steroid (e.g., oral dexamethasone (8 mg) or intravenous dexamethasone (10 mg), or an equivalent), paracetamol or acetaminophen (e.g., 500 mg of oral paracetamol or an equivalent), a histamine blocker (e.g., oral H2 blocker (e.g., ranitidine 150 mg or famotidine 20 mg, or an equivalent) and/or an oral H1 blocker (e.g., cetirizine (10 mg) or equivalent).

In certain embodiments, the method described herein further include the step of evaluating the subject after administration of the first dose, the second dose, or both, for the presence of one or more of the following: a skin reaction (e.g., urticaria, erythema, edema, rash, pruritus, eruptions), a hemodynamic change, e.g., a change in blood pressure (e.g., hypotension or hypertension), a respiratory problem (e.g., laryngospasm, laryngeal edema, bronchospasm, dyspnea), pain (e.g., joint pain, back pain, abdominal pain or chest pain), or other manifestations of hypersensitivity (e.g., one or more of fever, chills, nausea, vomiting or neurological changes).

Alternatively, or in combination, the methods described herein further include the step of evaluating the subject after administration of the first dose, the second dose, or both, for a change in a complement marker, e.g., complement activation (e.g., a change in one or more complement factors chosen from Bb or C3a$^b$), wherein an increase the level of a complement biomarker is indicative of a hypersensitivity reaction.

A change in a complement marker can be detected in vivo or using an in vitro assay. For example, a change in complement activation can be detected using an assay that detects a complement cascade component, e.g, an assay (e.g., ELISA) that detects one or more of: total complement proteins (e.g., C3 and C5); complement split products (e.g., Bb, C3a or C5a), or terminal complement complement complex: sCSb-9. Additional examples of in vitro assays for evaluating complement activity include CH50: Residual total hemolytic complement activity, or AH50: Residual alternative pathway of hemolytic complement activity. Alternatively, a change in complement activation can be detected using a complement depletion model (e.g., Cobra Venom Factor) for loss-of-function studies or a porcine model for complement-mediated hypersensitivity (e.g., a porcine model as described herein). In embodiments, a sample to be evaluated can be obtained from a subject exposed to the compositions described herein. For example, the sample can be a serum/plasma sample obtained for an in vivo assay. In other embodiments, naïve serum/plasma can be used for modeling complement activation in vitro.

Alternatively, or in combination, the methods described herein further include the step of evaluating the subject after administration of the first dose, the second dose, or both, for a change in thromboxane levels, e.g., thromboxane B2 in plasma, e.g., wherein an increase in the level of thromboxane is indicative of an increased hypersensitivity reaction, e.g., an increased acute hypersensitivity reaction.

Alternatively, or in combination, the methods described herein further include the step of evaluating the subject after administration of the first dose, the second dose, or both, or changes in one or more cytokines chosen from interferon-alpha, interferon-gamma, tumor necrosis factor-alpha, interleukin 1beta, interleukin 1 receptor antagonist (IL-1RA), interleukin-6, interleukin-8, interleukin-12, interleukin-18, interferon inducing protein-10, granulocyte colony stimulating factor, or C-reactive protein (CRP). In certain embodiments, an increase in the level of IL-6, IL-8, IL-1RA or CRP is indicative of an increased hypersensitivity reaction, e.g., relative to a reference parameter (e.g., a subject exposed to a bolus dose, or the subject prior to treatment).

Methods to measure polypeptide biomarkers (e.g., complement markers, thromboxane, cytokines), include, but are not limited to: Western blot, immunoblot, enzyme-linked immunosorbent assay (ELISA), radioimmunoassay (MA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF) mass spectrometry, microcytometry, microarray, microscopy, fluorescence activated cell sorting (FACS), flow cytometry, laser scanning cytometry, hematology analyzer and assays based on a property of the protein including but not limited to DNA binding, ligand binding, or interaction with other protein partners.

The activity or level of a marker protein can also be detected and/or quantified by detecting or quantifying the expressed polypeptide. The polypeptide can be detected and quantified by any of a number of means well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (MA), enzyme-linked immunosorbent assays (ELISAs), immunofluorescent assays, Western blotting, immunohistochemistry and the like. A skilled artisan can readily adapt known protein/antibody detection methods for use in determining the expression level of one or more biomarkers in a serum sample.

Another agent for detecting a polypeptide of the invention is an antibody capable of binding to a polypeptide corresponding to a marker of the invention, e.g., an antibody with a detectable label. Antibodies can be polyclonal or monoclonal. An intact antibody, or a fragment thereof (e.g., Fab or F(ab$'_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The polypeptide is detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition.

Marker expression level can also be assayed. Expression of a marker of the invention can be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the gene transcript (mRNA or cDNA made therefrom) using nucleic acid hybridization techniques are known to those of skill in the art (see e.g., Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the target cDNA.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1. siRNA Synthesis

Source of Reagents

Where the source of a reagent is not specifically given herein, such reagent may be obtained from any supplier of reagents for molecular biology at a quality/purity standard for application in molecular biology.

Oligonucleotide Synthesis.

All oligonucleotides are synthesized on an AKTAoligopilot synthesizer. Commercially available controlled pore glass solid support (dT-CPG, 500 Å, Prime Synthesis) and RNA phosphoramidites with standard protecting groups, 5'-O-dimethoxytrityl N$_6$-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N'-diisopropyl-2-cyanoethylphosphoramidite (Pierce Nucleic Acids Technologies) were used for the oligonucleotide synthesis. The 2'-F phosphoramidites, 5'-O-dimethoxytrityl-N4-acetyl-2'-fluoro-cytidine-3'-O—N,N'-diisopropyl-2-cyanoethyl-phosphoramidite and 5'-O-dimethoxytrityl-2'-fluoro-uridine-3'-O—N,N'-diisopropyl-2-cyanoethyl-phosphoramidite are purchased from (Promega). All phosphoramidites are used at a concentration of 0.2M in acetonitrile ($CH_3CN$) except for guanosine which is used at 0.2M concentration in 10% THF/ANC (v/v). Coupling/recycling time of 16 minutes is used. The activator is 5-ethyl thiotetrazole (0.75M, American International Chemicals); for the PO-oxidation iodine/water/pyridine is used and for the PS-oxidation PADS (2%) in 2,6-lutidine/ACN (1:1 v/v) is used.

3'-ligand conjugated strands are synthesized using solid support containing the corresponding ligand. For example, the introduction of cholesterol unit in the sequence is performed from a hydroxyprolinol-cholesterol phosphoramidite. Cholesterol is tethered to trans-4-hydroxyprolinol via a 6-aminohexanoate linkage to obtain a hydroxyprolinol-cholesterol moiety. 5'-end Cy-3 and Cy-5.5 (fluorophore) labeled iRNAs are synthesized from the corresponding Quasar-570 (Cy-3) phosphoramidite are purchased from Biosearch Technologies. Conjugation of ligands to 5'-end and or internal position is achieved by using appropriately protected ligand-phosphoramidite building block. An extended 15 min coupling of 0.1 M solution of phosphoramidite in anhydrous $CH_3CN$ in the presence of 5-(ethylthio)-1H-tetrazole activator to a solid-support-bound oligonucleotide. Oxidation of the internucleotide phosphite to the phosphate is carried out using standard iodine-water as reported (1) or by treatment with tert-butyl hydroperoxide/acetonitrile/water (10:87:3) with 10 min oxidation wait time conjugated oligonucleotide. Phosphorothioate is introduced by the oxidation of phosphite to phosphorothioate by using a sulfur transfer reagent such as DDTT (purchased from AM Chemicals), PADS and or Beaucage reagent. The cholesterol phosphoramidite is synthesized in house and used at a concentration of 0.1 M in dichloromethane. Coupling time for the cholesterol phosphoramidite is 16 minutes.

Deprotection I (Nucleobase Deprotection)

After completion of synthesis, the support is transferred to a 100 mL glass bottle (VWR). The oligonucleotide is cleaved from the support with simultaneous deprotection of base and phosphate groups with 80 mL of a mixture of ethanolic ammonia [ammonia:ethanol (3:1)] for 6.5 h at 55° C. The bottle is cooled briefly on ice and then the ethanolic ammonia mixture is filtered into a new 250-mL bottle. The CPG is washed with 2×40 mL portions of ethanol/water (1:1 v/v). The volume of the mixture is then reduced to ~30 mL by roto-vap. The mixture is then frozen on dry ice and dried under vacuum on a speed vac.

Deprotection II (Removal of 2'-TBDMS Group)

The dried residue is resuspended in 26 mL of triethylamine, triethylamine trihydrofluoride (TEA·3HF) or pyridine-HF and DMSO (3:4:6) and heated at 60° C. for 90 minutes to remove the tert-butyldimethylsilyl (TBDMS) groups at the 2' position. The reaction is then quenched with 50 mL of 20 mM sodium acetate and the pH is adjusted to 6.5. Oligonucleotide is stored in a freezer until purification.

Analysis

The oligonucleotides are analyzed by high-performance liquid chromatography (HPLC) prior to purification and selection of buffer and column depends on nature of the sequence and or conjugated ligand.

HPLC Purification

The ligand-conjugated oligonucleotides are purified by reverse-phase preparative HPLC. The unconjugated oligonucleotides are purified by anion-exchange HPLC on a TSK gel column packed in house. The buffers are 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides are pooled, desalted, and lyophilized. Approximately 0.15 OD of desalted oligonucleotidess are diluted in water to 150 μL and then pipetted into special vials for CGE and LC/MS analysis. Compounds are then analyzed by LC-ESMS and CGE.

siRNA Preparation

For the general preparation of siRNA, equimolar amounts of sense and antisense strand are heated in 1×PBS at 95° C. for 5 min and slowly cooled to room temperature. Integrity of the duplex is confirmed by HPLC analysis.

Nucleic acid sequences are represented below using standard nomenclature, and specifically the abbreviations of Table 2.

TABLE 2

Abbreviations of nucleotide monomers used in nucleic acid sequence representation. It will be understood that these monomers, when present in an oligonucleotide, are mutually linked by 5′-3′-phosphodiester bonds.

| Abbreviation | Nucleotide(s) |
| --- | --- |
| A | Adenosine-3'-phosphate |
| Ab | beta-L-adenosine-3'-phosphate |
| Abs | beta-L-adenosine 3'-phosphorothioate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cb | beta-L-cytidine-3'-phosphate |
| Cbs | beta-L-cytidine-3'-phosphorothioate |
| Cf | 2'-fluorocytidine-3'-phosphate |
| Cfs | 2'-fluorocytidine-3'-phosphorothioate |
| (Chd) | 2'-O-hexadecyl-cytidine-3'-phosphate |
| (Chds) | 2'-O-hexadecyl-cytidine-3'-phosphorothioate |
| Cs | cytidine-3'-phosphorothioate |
| G | guanosine-3'-phosphate |
| Gb | beta-L-guanosine-3'-phosphate |
| Gbs | beta-L-guanosine-3'-phosphorothioate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tb | beta-L-thymidine-3'-phosphate |
| Tbs | beta-L-thymidine-3'-phosphorothioate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Ub | beta-L-uridine-3'-phosphate |
| Ubs | beta-L-uridine-3'-phosphorothioate |
| Uf | 2'-fluorouridine-3'-phosphate |
| Ufs | 2'-fluorouridine-3'-phosphorothioate |
| (Uhd) | 2'-O-hexadecyl-uridine-3'-phosphate |
| (Uhds) | 2'-O-hexadecyl-uridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dA | 2'-deoxyadenosine-3'-phosphate |
| dAs | 2'-deoxyadenosine-3'-phosphorothioate |
| dC | 2'-deoxycytidine-3'-phosphate |
| dCs | 2'-deoxycytidine-3'-phosphorothioate |
| dG | 2'-deoxyguanosine-3'-phosphate |
| dGs | 2'-deoxyguanosine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96[1] | N-[tris(GalNAc-alkyl)-aminodecanoyl)]-4-hydroxyprolinol Hyp-(GalNAc-alkyl)3 |
| (Aeo) | 2'-O-methoxyethyladenosine-3'-phosphate |
| (Aeos) | 2'-O-methoxyethyladenosine-3'-phosphorothioate |
| (Geo) | 2'-O-methoxyethylguanosine-3'-phosphate |
| (Geos) | 2'-O-methoxyethylguanosine-3'-phosphorothioate |
| (Teo) | 2'-O-methoxyethyl-5-methyluridine-3'-phosphate |

TABLE 2-continued

Abbreviations of nucleotide monomers used in nucleic acid sequence representation. It
will be understood that these monomers, when present in an oligonucleotide, are mutually linked
by 5'- 3'-phosphodiester bonds.

| Abbreviation | Nucleotide(s) |
|---|---|
| (Teos) | 2'-O-methoxyethyl-5-methyluridine-3'-phosphorothioate |
| (m5CeO) | 2'-O-methoxyethyl-5-methylcytidine-3'-phosphate |
| (m5Ceos) | 2'-O-methoxyethyl-5-methylcytidine-3'-phosphorothioate |

[1] The chemical structure of L96 is as follows:

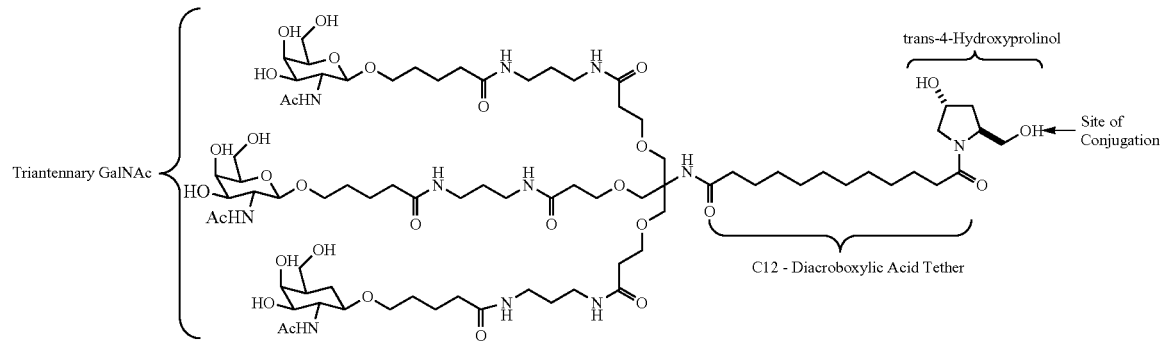

Example 2. Bolus Dosing Study of siRNA-LNP Formulation in a Porcine Model for Lipid Nanoparticle IRR/Hypersensitivity Reactions This study evaluated the acute infusion-related reaction (IRR) following intravenous (IV) bolus administration of siRNA-LNP to domestic Yorkshire pigs. Complement-mediated acute hypersensitivity reactions caused by a single bolus dose of siRNA-LNP were investigated in this porcine model. Induction of tachyphylaxis by sequential repeat/increased bolus dosing of siRNA-LNP was also determined.

Methods and Experimental Design

Animals

The effect of siRNA-LNP on IRR was investigated in anesthetized, spontaneously breathing domestic pigs by administration of test formulation by IV bolus.

The porcine liposomal infusion reactions closely mimic human response. Administration of low (milligram) doses of nanoparticulate materials in pigs can lead to acute cardiopulmonary, hemodynamic, hematological, biochemical and dermatological changes within minutes, mimicking the human IRR to nanomedicines and biologics.

Exemplary features of porcine hypersensitivity reactions include, but not limited to, cardiopulmonary distress (hyper/hypotension (pulmonary hypertension with/without systemic hyper/hypotension), cardiac arrhythmias, tachycardia, bradycardia, cardiac arrest, decreased cardiac output, decreased pulse pressure, decreased left ventricular end-diastolic pressure), cutaneous changes (flushing, rash), bronchospasm, dyspnea/apnea, leucopenia/leukocytosis, thrombocytopenia, increased adenosine, and increased thromboxane $A_2$.

Pigs are sensitive to liposomes and are therefore a good model for hypersensitive human individuals. Exemplary porcine models of complement-mediated infusion reactions are described, e.g., in Szebeni J. et al., *Adv. Drug Deliv. Rev.* 2012; 64(15): 1706-1716, the content of which is incorporated herein by reference.

Three male, domestic Yorkshire pigs (12-14 weeks/34-37 kg) were used in this study. Animals were preanesthetized intramuscularly with Calypsol/Xilazine injections and the anesthesia was maintained using isoflurane gas. Animals were breathing spontaneously. Respiration was monitored by using a pulse oximeter (fixed on the tongue), monitoring oxygen saturation and respiratory rate. Temperature was measured in the rectum. A capnograph was connected to the tracheal tube to monitor $etCO_2$ and the respiratory rate.

All incision areas were washed by a liberal application of povidone iodine 10%.

The pigs were instrumented with Swan-Ganz catheter, introduced into the pulmonary artery through the right external jugular vein→right atrium→right ventricle measuring the pulmonary arterial pressure (PAP); a pressure transducer was connected into the femoral artery to record the systemic arterial pressure (SAP). The left femoral vein was cannulated for blood sampling. The left external jugular vein was also cannulated for the administration of test formulation and to maintain a slow drop infusion of saline (~3 mL/kg/h).

ECG signals, according Einthoven's leads were also continuously recorded.

SiRNA-LNP Formulation

Each of the three male pigs received multiple IV bolus injections of the following siRNA-LNP formulation: MC3/DSPC/Chol/PEG2000-C-DMG (50/10/38.5/1.5 mol %). The ratio of total lipid/siRNA: 12.23. The siRNA duplex has the following sequences: GccuGGAGuuuAuucG-GAAdTsdT (SEQ ID NO: 5) (sense strand) and UUCCGAAuAAACUCcAGGCdTsdT (SEQ ID NO: 6) (antisense strand). This siRNA duplex targets rat proprotein convertase subtilisin/kexin type 9 (PCSK9) gene and has no detectable cross-reactivity with pig sequence.

Administration

Each animal received fixed unit sequential doses of 0 mg (saline control), 2 mg, 2 mg, 10 mg, and 20 mg (all doses based on siRNA content) by IV bolus injection via cannulated left jugular vein (washed in by 5 mL saline), with at least 0.5 hr between doses to allow for recovery to baseline. Dosing solutions were prepared from a 2 mg/mL stock solution diluted in 0.9% sterile saline to appropriate concentrations for a constant total injection volume of 10 mL/injection. Saline served also as negative control, each experiment started with 10 mL bolus injection of saline to test the reactivity. Following the last injection of the tested siRNA-LNP the animals received an IV bolus injection of Zymosan (0.5 mg/kg), which is known to induce acute cardiovascular changes associated with complement activation. Table 3 shows the lipid dose rates and total doses used in this study.

TABLE 3

Lipid Dose Rates and Total Doses

| Sequential Bolus Doses | Bolus 1 | Bolus 2 | Bolus 3 | Bolus 4 |
|---|---|---|---|---|
| Total Lipid Dose/Bolus (mg) | 24.5 | 24.5 | 122.3 | 244.6 |
| Cumulative Lipid Dose (mg) | 24.5 | 49.0 | 171.3 | 416.0 |
| Lipid Concentration (mg/ml) | 2.5 | 2.5 | 12.2 | 24.5 |
| Lipid Dose Rate (mg/min) | 49 | 49 | 244 | 489 |
| Dosing Time 0.5 min (estimate) | | | | |

Data Collection

The following parameters were evaluated: cardiovascular (pulmonary and systemic pressure, heart rate), ECG (Einthoven's MI-III leads), respiratory parameters (respiratory rate, end-tidal $CO_2$, blood $O_2$ saturation), clinical signs, hematology (platelets (PLT), white blood cells (WBC), red blood cells (RBC), hemoglobin content or RBCs (Hb), lymphocytes (LYM), and granulocytes (GR)), and body temperature.

Plasma samples were collected pre- and post-each dose at specific time-points for evaluation of Thromboxane B2 for pig 3 only. Serum and plasma samples were collected pre- and post-each dose at specific time-points for evaluation of biomarkers.

Results

IV bolus administration of the test siRNA-LNP resulted in an acute infusion-related reaction (IRR) in all three animals following the first dose of the formulation (2 mg).

In the first animal (pig 1), the pulmonary arterial pressure (PAP) increased to 370% of the pre-test value combined with an increase in systemic arterial pressure (SAP) to 130% and a minor change in heart rate (HR) to 107% of the pre-test value, respectively. FIG. 1 shows changes in absolute values, i.e., PAP, SAP are expressed in mmHg, HR in beat/min, in pig 1.

Figure 2:
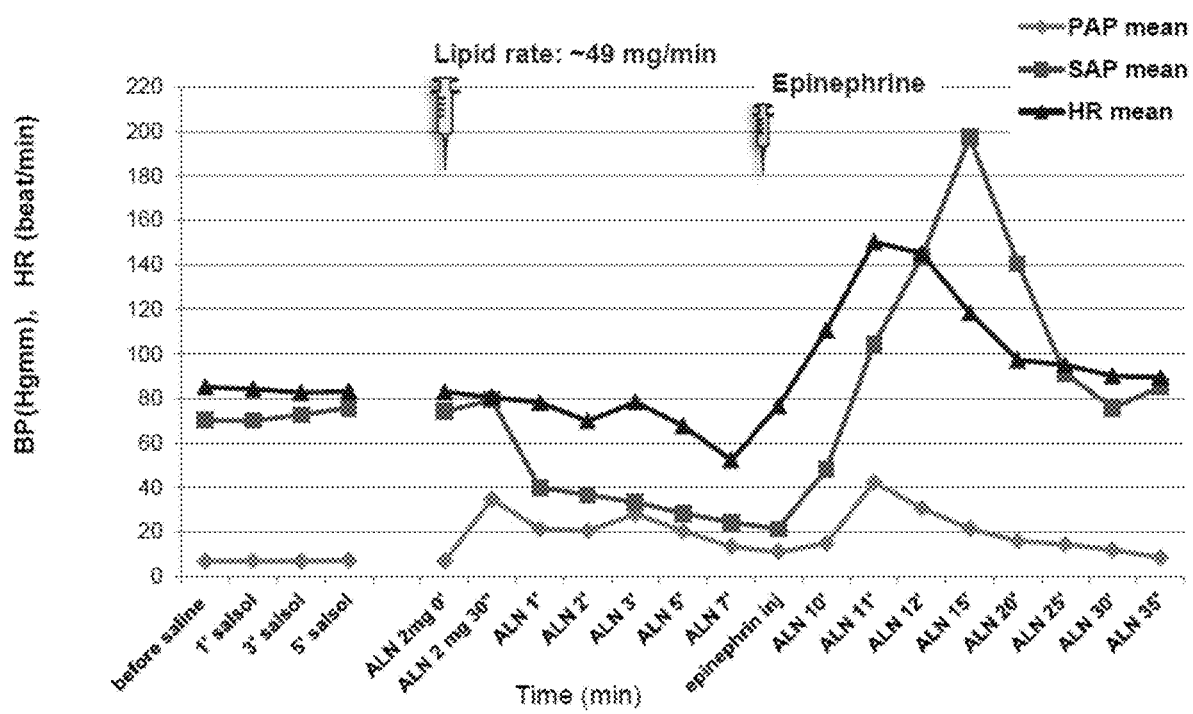
FIG. 2 depicts the hemodynamic changes (PAP, SAP and HR) after first bolus dose of siRNA-LNP formulation in pig 3.

In the second animal (pig 2), a sharp PAP increase to 500% of the pre-test value was observed, while the SAP showed an initial moderate increase to 107% that was immediately followed by a sharp decrease to 28% of the SAP pre-test value, combined with a decrease in HR to 63%. FIG. 2 shows changes in absolute values, i.e., PAP, SAP are expressed in mmHg, HR in beat/min, in pig 2.

In the third animal (pig 3), a sharp increase in PAP to 404% of the pre-test value was observed, while the SAP showed an initial increase to 110% followed by a sharp decrease to 43% and the HR showed an initial increase to 120% followed by a sharp decrease to 68% of the pre-test values, respectively.

In animals two and three, skin changes (whole body flush and abdominal rash) were also observed. Respiratory arrest occurred in animals two and three and both animals were manually resuscitated and received an injection of epinephrine.

The second 2 mg siRNA-LNP dose evoked negligible changes in all 3 animals, suggesting that the animals had become tachyphylactic to administration of an equivalent dose.

Administration of a subsequent 10 mg dose caused mild PAP increase without SAP or HR changes in pigs 1 and 2, and only a negligible PAP increase and SAP decrease in pig 3. The subsequent 20 mg dose evoked cardiovascular reactions in all three animals that displayed slower kinetics and milder responses than what was observed after the first dose: pig 1, long lasting, biphasic increases in PAP; pig 2, shorter changes in PAP, SAP and HR were observed; pig3, mild increases in PAP and steady decrease in SAP decrease.

For pig 3, the plasma samples were analyzed for Thromboxane B2 (TXB2) levels by ELISA. After the first test article dose a sharp increase in TXB2 of ~58-fold over baseline was observed 2 min. post dose that decreased to ~10-fold over baseline at 30 min post dose. The subsequent doses did not result in TXB2 release.

The vehicle injection (saline solution, 10 mL IV bolus), that preceded in every experiment the test material injections did not evoke any cardiovascular alterations.

Conclusion

A 2 mg (based on siRNA) unit IV bolus dose (10 mL) of siRNA-LNP formulation resulted in a significant IRR in all animals based on cardiovascular changes (PAP, SAP, HR) and clinical signs of toxicity in 2 out of 3 animals. Repeated administration of the same dose after a 1-1.25 hr recovery period did not result in a similar reaction, suggesting that the animals were refractory to further stimulation. Subsequent administration of a 5-fold higher dose (10 mg) resulted in a mild cardiovascular reaction in 2 out of 3 animals and the kinetics of these responses were slower than what was observed following the first dose of 2 mg. A stronger response was observed in all animals after an additional 20 mg dose of the formulation. These data suggest that the tachyphylaxis observed after the first and second doses of 2 mg could be overcome by administration of a higher dose. However, none of the responses to the higher doses displayed the same rapid kinetics and severity that was seen for the first dose.

Example 3: Microdosing Study of siRNA-LNP Formulation in a Porcine Model for Lipid Nanoparticle Hypersensitivity Reactions (Protocol I)

This study evaluated the acute and delayed infusion-related reaction (IRR) following intravenous (IV) infusion at different dose rates/regimens of siRNA-LNP to domestic Yorkshire pigs.

Methods and Experimental Design

Animals

The same animal model described in Example 2 was used in this study. The animals were prepared as described in Example 2. In addition, for urine samples a short midline incision was made in the abdomen, and a plastic tube was inserted and fixed into the urinary bladder.

SiRNA-LNP Formulation

The siRNA-LNP formulation used in this study is described in Example 2.

Administration

Six (6) pigs were administered a total dose of 0.5 mg/kg siRNA-LNP formulation by IV infusion at different dose rates/regimens (2 animals/group). The dosing regimen was as follows:

pigs 01 and 02: 0.5 mg/kg infused over 60 minutes
pigs 03 and 04: 0.5 mg/kg infused over 120 minutes
pigs 05 and 06: 0.5 mg/kg total dose, $1/10^{th}$ of the dose infused over 15 minutes followed immediately by the remaining $9/10^{th}$ of the dose over 60 min.

Dosing solutions were prepared from a 1.98 mg/mL stock solution diluted in 0.9% sterile saline to appropriate concentrations for a constant total infusion volume of 50 mL. At the end of the cardiovascular monitoring period, the animals received an IV bolus injection of Zymosan (0.5 mg/kg), which is known to induce acute cardiovascular changes associated with complement activation.

Data Collection

The following parameters were evaluated: cardiovascular (pulmonary and systemic pressure, heart rate), ECG (Einthoven's MI-III leads), respiratory parameters (respiratory rate, end-tidal $CO_2$, blood $O_2$ saturation), clinical signs, blood cell and platelet counts, plasma histamine, plasma tryptase, and body temperature. Plasma and urine samples were collected before infusion and during and after the infusion at specific timepoints for evaluation of Thromboxane B2. Serum and plasma samples were collected at specific timepoints for evaluation of biomarkers. Biomarkers included plasma Thromboxane B2 and serum cytokines/chemokines (GM-CSF, IFNγ, IL-10, IL-12, IL-18, IL-1RA, IL-1α, IL-1β, IL-2, IL-4, IL-6, IL-8, and TNFα).

Results

IV infusion of 0.5 mg/kg siRNA-LNP formulation over 60 minutes in pig01 and pig02 resulted in mild cardiovascular changes during the infusion and severe changes 15-30 min after the infusion in both animals.

Figure 3:
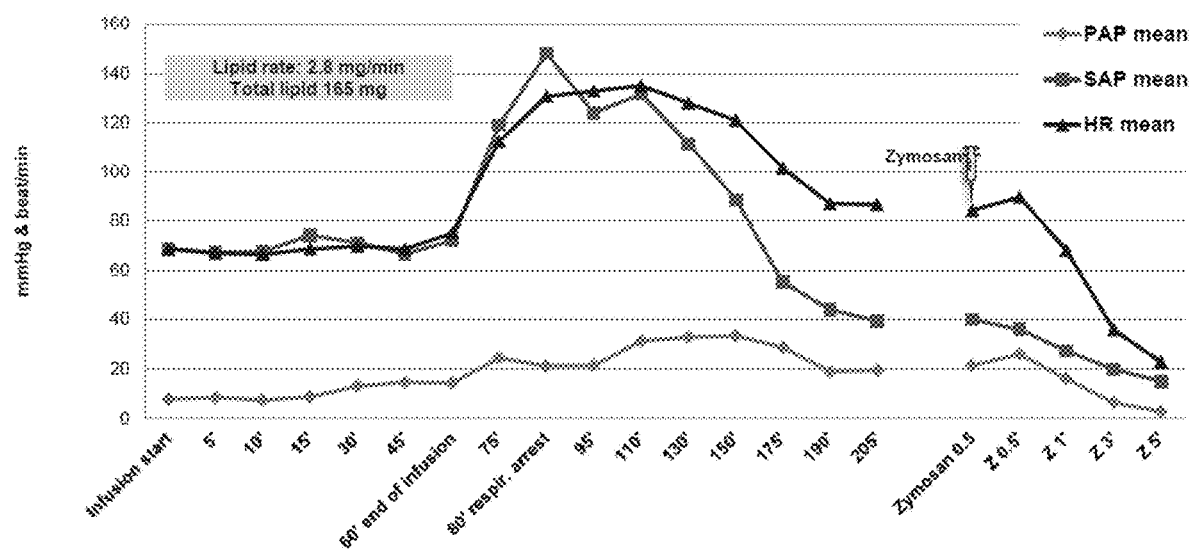
FIG. 3 depicts the hemodynamic changes (PAP, SAP and HR) in pig01 infused at a dose of 0.5 mg/kg in a 50 mL volume over 60 minutes.

During infusion, in pig01 only a slow, moderate increase in pulmonary arterial pressure (PAP; 190% of the pre-test value) was observed, while in pig02 only a mild increase in systemic arterial pressure (SAP) was observed in the first 5 min that was followed by a gradual decrease in SAP (78% of the pre-test value). After the infusion, dramatic elevations in PAP, SAP and heart rate (HR) were observed in both animals combined with skin changes (pig01: whole body flush and rash; pig02: whole body flush) and ECG changes. For pig01, the PAP had increased to 430% of the pre-test value at 150 min post start of infusion and started to decline at 175 min, but never returned to the pre-test value. HR and SAP followed similar kinetics. For pig02, a similar reaction was observed but the changes started around 15 min later than in pig01 and the PAP reached a maximum of 382% of the pre-test value at 140 min post start of infusion. FIG. 3 shows changes in absolute values, i.e., PAP, SAP are expressed in mmHg, HR in beat/min, in pig01.

IV infusion of 0.5 mg/kg the tested siRNA-LNP formulation over 120 minutes in pig03 and pig04 resulted in mild cardiovascular changes during the infusion and severe changes after the infusion in both animals. Within 30 min after the infusion ended the PAP started to rise sharply. The PAP reached a maximum of 625% of the pre-test value at 285 min post start of infusion in pig03 and 278% at 240 min post start of infusion in pig04, respectively. In both animals mild skin flushing and ECG changes were observed.

Figure 4:
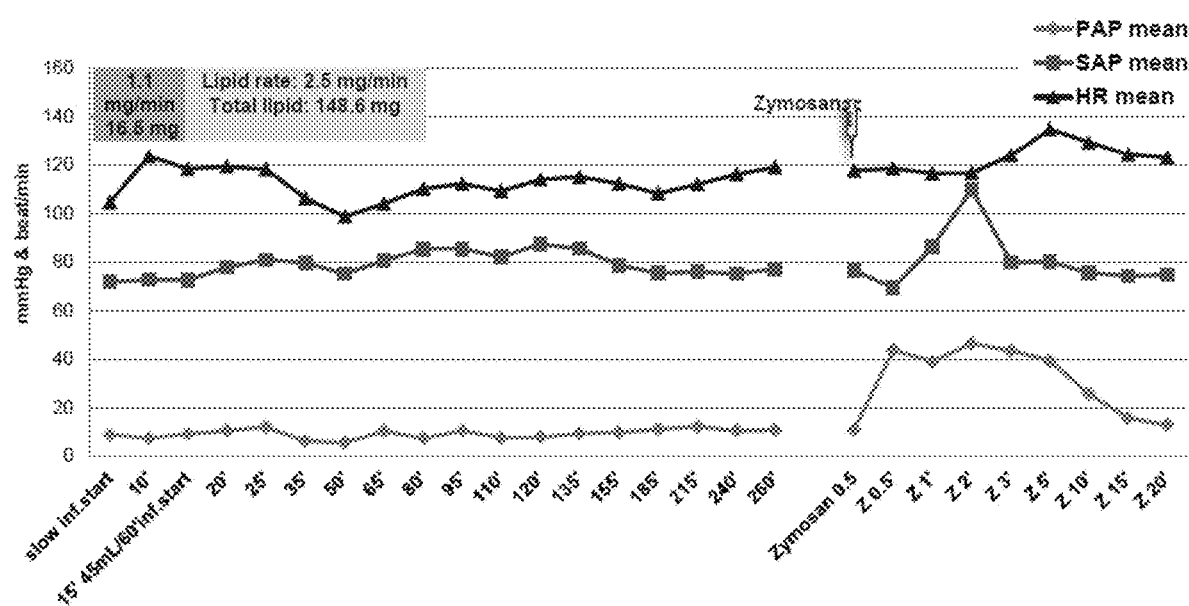
FIG. 4 depicts the hemodynamic changes (PAP, SAP and HR) in pig06 infused at a dose of 0.5 mg/kg in a 50 mL volume in two steps: $1/10^{th}$ of total dose over 15 minutes followed by the remaining $9/10^{th}$ of the dose over additional 60 minutes.

IV infusion of 0.5 mg/kg the tested siRNA-LNP formulation in two steps by first infusing $1/10^{th}$ of the dose over 15 min immediately followed by $9/10^{th}$ of the dose over 60 minutes in pig05 and pig06 resulted in only very mild changes overall. During the entire infusion period PAP, SAP and HR were stable for pig05 and there were only minimal PAP fluctuations between 66-136% of the pre-test value for pig06. FIG. 4 shows changes in absolute values, i.e., PAP, SAP are expressed in mmHg, HR in beat/min, in pig06. After the infusion, only a mild, gradual increase in PAP to a maximum of 160% at 160 min post start of infusion was observed in pig05. In pig05 no skin or ECG changes were observed and in pig06 no skin changes and only minimal ECG changes were seen.

For pig01 and pig02, Thromboxane B2 (TxB2) plasma levels remained stable during IV infusion. After end of infusion, an increase in TxB2 over time was observed for both animals, with pig01 reaching a maximum of 5-fold over TxB2 baseline level at 240 min and pig02 reaching a maximum of 16-fold over baseline at 150 min. TxB2 release coincided with PAP increase. Urine TxB2 levels were analyzed only for pig01, but all values were above ULOQ of the assay.

In pig03 and pig04 TxB2 plasma also increased over time and maximum levels of 6.5-fold over baseline at 240 min and 4.7-fold over baseline was reached at 225 min. TxB2 release coincided with PAP increase.

In pig05 TxB2 plasma levels were high at baseline and decreased 0.3-fold over time. In pig06, TxB2 increased over time and reached a maximum of 4.6-fold over baseline at 150 min, which is similar in magnitude to pigs 01, 03, and 04, but there was no corresponding increase in PAP.

For serum cytokines, an increase in the levels of IL-6, IL-8, IL-18 and IL-1RA were observed. No significant changes were observed for GM-CSF, IFNγ, IL-10, IL-12, IL-1a, IL-10, IL-2, IL-4, and TNFα.

Conclusion

None of the infusion regimens used in this study resulted in an acute IRR similar to the reaction that was observed within minutes of a bolus administration of 2 mg of the tested siRNA-LNP formulation as described in Example 1.

Administration of 0.5 mg/kg the tested siRNA-LNP formulation by IV infusion over 60 min or 120 min resulted in a severe response that started within 30 min after end of infusion and was characterized by pulmonary hypertension, systemic hypo- or hypertension, skin flushing and ECG alterations. Microdosing $1/10^{th}$ of the dose followed by $9/10^{th}$ of the dose did not result in a significant response at any of the times observed.

Overall, the two animals within each of the three dose groups showed responses with similar kinetics but different intensities. This is in agreement with the response heterogeneity seen in Example 1. There was a clear difference between the single step infusions when compared to the microdosed group, since there were no severe changes at any time in the latter group. These data suggest microdosing as a valuable strategy for preventing lipid-nanoparticle induced IRR.

In pigs, 01, 02, 03, 04, and 06 rises of plasma TxB over time were observed. The TxB2 in pig06 from the microdosed group was in a similar range of fold-induction over baseline as the 60/120 min infusion group and the TxB2 levels in pig05 from the microdosed group had high baseline levels.

Example 4: Microdosing Study of siRNA-LNP Formulation in a Porcine Model for Lipid Nanoparticle Hypersensitivity Reactions (Protocol II)

This study uses an alternative microdosing protocol to evaluate the acute and/delayed infusion-related reaction (IRR) following intravenous (IV) infusion at different dose rates/regimens of siRNA-LNP to domestic Yorkshire pigs.

Methods and Experimental Design

Animals

The effect of microdosing of siRNA-LNP formulation on preventing or reducing IRR was investigated using the animal model as described in Example 2.

SiRNA-LNP Formulation

The siRNA-LNP formulation used in this study is described in Example 2.

Administration

Six (6) pigs are administered a total dose of 5.85 mg/kg tested siRNA-LNP formulation by IV infusion at different dose rates/regimens (3 animals/group). The dosing regimen is shown in Table 4.

TABLE 4

Study Design

| Group | No. of Pigs | Test Article/ Positive Control | Total Dose (mg/kg) | Total Dose Volume (mL) | Dose Rate (mg/min) | Route |
|---|---|---|---|---|---|---|
| 1 | 3 | siRNA-LNP | 5.85 | 50 | 10 | IV Infusion |
|   |   | Zymosan | 5 | 5 | N/A | IV Bolus |
| 2 | 3 | siRNA-LNP | 5.85 | 50 | 1 (for first 15 min) 10 (for remainder of dose) | IV Infusion |
|   |   | Zymosan | 5 | 5 | N/A | IV Bolus |

The total dose (5.85 mg/kg) and the total infusion volume (50 mL) are held constant for each animal. Based on individual animal body weight, an appropriate volume of stock siRNA-LNP formulation is diluted with 0.9% saline to a total volume of 60 mL in a sterile glass vial. At the end of the cardiovascular monitoring period, the animals received an IV bolus injection of Zymosan (0.5 mg/kg), which is known to induce acute cardiovascular changes associated with complement activation.

Data Evaluation

Data are collected and analyzed as described in Examples 2 and 3.

Experiments conducted as described in Example 4 demonstrated a clear difference between the microdosed group (1 mg/min, followed by 10 mg/min) and the straight 10 mg/min group. The TxB2 elevations were significantly higher in the 10 mg/min group.

Example 5: Microdosing Study of siRNA-LNP Formulation in Humans

This study evaluated the infusion-related reaction (IRR) following intravenous (IV) infusion at different dose rates/regimens of siRNA-LNP in human patients.

Patients were administered a total dose of 0.30 mg/kg siRNA-LNP formulation by IV infusion at different dose rates/regimens. The total dose was based on the amount of siRNA in the formulation. The lipid:siRNA ratio ranged from 11.5-14:1. For certain batch, it was around 11.6:1.

The dosing regimen was as follows:

Ten (10) patients: 0.30 mg/kg infused over a period of 60 minutes. The 60-minute infusion occurred at a rate of 3 mL/min for the full 60 minutes.

Thirty-two (32) patients: 0.30 mg/kg infused over a period of 70 minutes (microdosing regimen). The 70-minute infusion occurred at a rate of 1 mL/min for the first 15 minutes and 3 mL/min for the remainder of the time.

Figure 5:
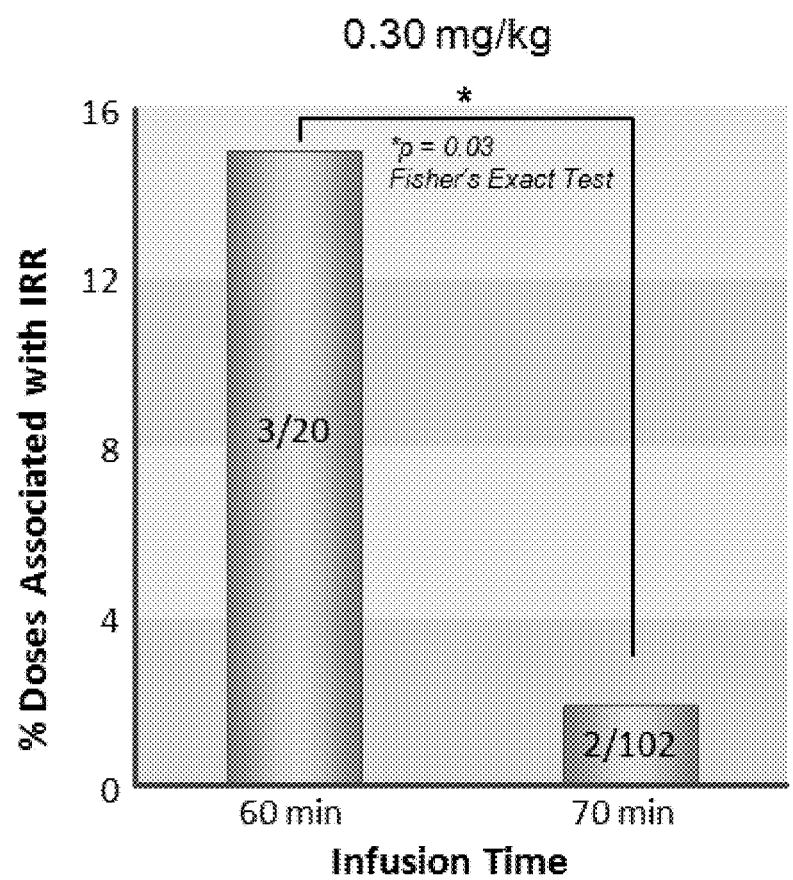
FIG. 5 is a bar graph showing the percentages of doses associated with infusion-related reactions (IRRs) in patients administered a total dose of 0.30 mg/kg siRNA-LNP formulation by IV infusion at different dose rates/regimens. The total dose was based on the amount of siRNA in the formulation. For the 60-minute regimen, the infusion occurred at a rate of 3 ml/min for the full 60 minutes. For the 70-minute regimen, the infusion occurred at a rate of 1 ml/min for the first 15 minutes and 3 ml/min for the remainder of the time.

Patients were assessed for symptoms, including blood pressure, heart rate and body temperature. FIG. 5 shows the percentages of doses associated with infusion-related reactions (IRRs) in those. As shown in FIG. 5, the incidence of IRRs was decreased from 15% (3/20) in patients who received the 60-minute regimen to 2% (2/102) in patients who received the 70-minute microdosing regimen.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of reducing an infusion-related response (IRR), or a hypersensitivity reaction, or both, in a subject, to a composition comprising a lipid formulation and a nucleic acid molecule, said method comprising administering to a subject:
   a first dose of said composition;
   a second dose of said composition; and
   wherein the amount of said composition administered in said first dose is no more than 1/10 of the amount of said composition administered in said second dose;
   wherein one or both of a)-b) of the following conditions is met:
   a) the first dose is administered over a time period that is no more than ½ of the time period over which the second dose is administered; or
   b) the rate of administration of said first dose is no more than ½ of the rate of administration of said second dose;
   and wherein the lipid formulation comprises a lipid-nucleic acid particle comprising a cationic lipid, a non-cationic lipid, and a PEG-lipid conjugate.

2. A method of reducing the expression of a target gene, or treating a disorder related to the target gene, in a subject, the method comprising:
   administering to the subject a first dose and a second dose of a composition, said composition comprising a lipid formulation and a nucleic acid molecule, wherein said first and second doses are administered in an amount sufficient to reduce expression of a target gene, or treat the disorder, in the subject; and
   wherein the amount of said composition administered in said first dose is no more than 1/10 of the amount of said composition administered in said second dose;
   wherein one or both of a)-b) of the following conditions is met:
   a) the first dose is administered over a time period that is no more than ½ of the time period over which the second dose is administered; or
   b) the rate of administration of said first dose is no more than ½ of the rate of administration of said second dose;

and wherein the lipid formulation comprises a lipid-nucleic acid particle comprising a cationic lipid, a non-cationic lipid, and a PEG-lipid conjugate.

3. The method of claim 1, wherein:
(i) the rate of administration of said first dose is about 5% to about 50%, about 10% to about 40%, or about 20% to about 40% of the rate of administration of the second dose;
(ii) the total amount of said composition administered in said first dose is about 0.5% to 20%, about 1% to about 15%, about 1% to about 10%, about 1% to about 5%, about 2% to about 10%, or about 5% to about 10% of the total amount of said composition, or the amount of the composition administered in said second dose; or
(iii) both (i) and (ii).

4. The method of claim 1, wherein:
(i) the rate of administration of the lipid formulation in said first dose is about 0.05 µg/min/kg to about 50 µg/min/kg, about 0.1 µg/min/kg to about 25 µg/min/kg;
(ii) the rate of administration of the lipid formulation in said second dose is about 0.5 µg/min/kg to about 500 µg/min/kg, about 1 µg/min/kg to about 250 µg/min/kg, about 10 µg/min/kg to about 150 µg/min/kg, or about 50 µg/min/kg to about 100 µg/min/kg; or
(iii) both (i) and (ii).

5. The method of claim 1, wherein:
(i) the rate of administration of the nucleic acid molecule in said first dose is about 0.01 µg/min/kg to about 5 µg/min/kg or about 0.02 µg/min/kg to about 2.5 µg/min/kg;
(ii) the rate of administration of the nucleic acid molecule in said second dose is chosen from about 0.1 µg/min/kg to about 50 µg/min/kg, about 0.2 µg/min/kg to about 25 µg/min/kg, about 0.5 µg/min/kg to about 10 µg/min/kg, or about 1 µg/min/kg to about 5 µg/min/kg; or
(iii) both (i) and (ii).

6. The method of claim 1, wherein:
(i) the amount of lipid formulation administered in said first dose is about 0.5 µg/kg to about 1000 µg/min/kg or about 1 µg/min/kg to about 500 µg/kg;
(ii) the amount of lipid formulation administered in said second dose is about 20 µg/kg to about 50000 µg/kg, about 100 µg/kg to about 25000 µg/kg, about 500 µg/kg to about 10000 µg/kg, or about 1000 µg/kg to about 5000 µg/kg; or
(iii) both (i) and (ii).

7. The method of claim 1, wherein:
(i) the amount of the nucleic acid molecule in said first dose is about 0.1 µg/kg to about 20 µg/kg;
(ii) the amount of the nucleic acid molecule in said second dose is about 2 µg/kg to about 1000 µg/kg, about 5 µg/kg to about 750 µg/kg, about 10 µg/kg to about 500 µg/kg, or about 50 µg/kg to about 300 µg/kg; or
(iii) both (i) and (ii).

8. The method of claim 1, wherein
(i) the second dose is administered over a time period that is at least 3 or 4 times greater than the time period over which the first dose is administered;
(ii) the first dose is administered over a time period that is no greater than ¼ or ⅕ the time period over which the total dose is administered;
(iii) the first dose is administered over a time period that is between 5% and 50%, between 10% and 45%, between 15% and 40%, between 20% and 35%, or between 25% and 30% of the time period of administration of the second dose;
(iv) the first dose is administered over a time period that is between 5 minutes and 60 minutes, between 10 minutes and 50 minutes, between 20 minutes and 40 minutes, between 5 minutes and 30 minutes, or between 10 minutes and 20 minutes;
(v) the second dose is administered over a time period that is between 30 minutes and 180 minutes, between 40 minutes and 120 minutes, between 45 minutes and 90 minutes, or between 50 minutes and 65 minutes; or
(vi) no more than 1, 10, 20, 30, 60, or 180 minutes separates the completion of the administration of the first dose and the initiation of the administration of the second dose.

9. The method of claim 1, further comprising administering to the subject one or more additional doses of the composition.

10. The method of claim 1, wherein said first and second doses are administered by intravenous, intraarterial, subcutaneous, intraperitoneal or intramuscular injection or infusion, intravenously by infusion, at a substantially constant rate via a pump or a sustained or controlled release formulation, or as a gradient for multiple rates.

11. The method of claim 10, wherein:
(i) the flow rate of administration of the first dose is no more than ½ or ⅓ of the flow rate of administration of said second dose;
(ii) the flow rate of administration of the first dose is chosen from about 0.5 to 1.5 mL/min, about 0.8 to 1.3 mL/min, about 1 to 1.2 mL/min, about 1 mL/min or 1.1 mL/min;
(iii) the flow rate of administration of the second dose is chosen from about 2 to 4 mL/min, about 2.5 to 3.7 mL/min, about 3 to 3.5 mL/min, about 3 mL/min or 3.3 mL/min;
(iv) both (ii) and (iii); or
(v) the total volume of infusion is about 100 to 300 mL, about 150 to 250 mL, about 180 mL or 200 mL.

12. The method of claim 1, wherein the IRR and/or hypersensitivity reaction is an acute hypersensitivity reaction during dose administration or occurs after administration of the second dose is completed.

13. The method of claim 1, further comprising evaluating the subject after administration of the first dose, the second dose, or both, for one or more of the following:
(i) the presence of one or more of the following: a skin reaction, a hemodynamic change, a change in blood pressure, a respiratory problem, pain, or one or more of fever, chills, nausea, vomiting or neurological changes;
(ii) a change in a complement biomarker chosen from one or more of complement activation, or a change in one or more complement factors chosen from Bb or $C3a^b$, wherein an increase the level of a complement biomarker is indicative of an IRR and/or hypersensitivity reaction;
(iii) a change in thromboxane levels or thromboxane B2 in plasma, wherein an increase in the level of thromboxane or thromboxane B2 is indicative of an increased hypersensitivity reaction; or
(iv) a change in one or more cytokines chosen from interferon-alpha, interferon-gamma, or tumor necrosis factor-alpha, interleukin 1beta, interleukin 1 receptor antagonist (IL-1RA), interleukin-6, interleukin-8, interleukin-12, interleukin-18, interferon inducing protein-10, granulocyte colony stimulating factor, or C-reactive protein (CRP), wherein an increase in the level of IL-6, IL-8, IL-1RA or CRP is indicative of an increased hypersensitivity reaction.

14. The method of claim 1, wherein:
(i) said method does not cause a detectable IRR and/or hypersensitivity reaction
(ii) said method results in a decrease in the IRR and/or hypersensitivity reaction, which is less than 1%, 5%, 10%, 25%, 30%, 35% or 40%;
(iii) said method causes a reduced IRR and/or hypersensitivity reaction leading to a reduction in the administration of one or more of a steroid, an analgesic, or a histamine receptor antagonist;
(iv) said subject does not receive administration of a steroid within X hours of any of the initiation of administration of said first dose, wherein X is less than 1 hour, 2 hours, 3 hours, 5 hours, 10 hours, 15 hours, 24 hours or 48 hours; or
(v) if said first and second dose regimen is provided to a porcine subject, the subject will show a reduced IRR and/or hypersensitivity reaction, relative to a subject exposed to a bolus dose, or the subject prior to treatment.

15. The method of claim 1, wherein the cationic lipid is selected from the group consisting of N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP, also referred to as N-(2,3-dioleoyloxy)propyl)-N,N,N-trimethylammonium chloride in U.S. Pat. No. 8,158,601), N-(I-(2,3-dioleyloxy)propyl)-N,N,N-trimethylammonium chloride (DOTMA, also referred to as N-(2,3-dioleyloxy)propyl-N,N—N-triethylammonium chloride in U.S. Pat. No. 8,158,601), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethylaminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), bis(3-pentyloctyl) 9-((4-(dimethylamino)butanoyl)oxy)heptadecanedioate, 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (also called DLin-M-C3-DMA, MC3, or M-C3; referred to as Formula I in U.S. Pat. No. 8,158,601, which is incorporated herein by reference; referred to herein as "MC3" "Formula I/MC3"), 1,1'-(2-(4-(2-((2-(bis(2-hydroxydodecyl)amino)ethyl)(2-hydroxydodecyl)amino)ethyl)piperazin-1-yl)ethylazanediyl) didodecan-2-ol (Tech G1), and a mixture thereof; and/or wherein the cationic lipid comprises from about 20 mol % to about 60 mol %, or about 40 mol % of the total lipid present in the formulation.

16. The method of claim 1, wherein the nucleic acid molecule is selected from the group consisting of a double stranded RNA (dsRNA) molecule, a single-stranded RNAi molecule, a microRNA (miRNA), an antisense RNA, a short hairpin RNA (shRNA), an antagomir, an mRNA, a decoy RNA, a DNA, plasmid, and an aptamer.

17. The method of claim 1, wherein:
(i) the first dose is administered at a first nucleic acid dose rate between 1.5 and 2 μg/kg/min, and the second dose is administered at a second nucleic acid dose rate between 4 and 6 μg/kg/min;
(ii) the first dose is administered at a first lipid dose rate between 15 and 25 μg/kg/min, and the second dose is administered at a second lipid dose rate between 55 and 75 μg/kg/min; or
(iii) both (i) and (ii).

18. The method of claim 1, wherein:
(i) the first dose is administered at between 0.5 and 1.5 mL/min, and the second dose is administered at between 2.5 and 3.5 mL/min;
(ii) the first dose is administered over a period of between 10 and 20 minutes, and the second dose is administered over a period of between 50 and 65 minutes; or
(iii) both (i) and (ii).

19. The method of claim 1, wherein:
(i) the amount of the first nucleic acid molecule administered in the first dose is between 20 and 30 μg/kg, and the amount of the second nucleic acid molecule administered in the second dose is between 250 and 300 μg/kg;
(ii) the amount of the lipid formulation administered in the first dose is between 250 and 400 μg/kg, and the amount of the lipid formulation administered in the second dose is between 2500 and 4000 μg/kg; or
(iii) both (i) and (ii).

20. The method of claim 1, wherein:
(i) the total nucleic acid dose in the first and the second doses is between 0.2 and 0.4 mg/kg;
(ii) the total lipid dose in the first and the second doses is between 3.0 and 4.5 mg/kg; or
(iii) both (i) and (ii).

21. The method of claim 1, wherein:
(i) the rate of administration of the nucleic acid molecule in the first dose is between 0.1 and 0.15 mg/min, and the rate of administration of the nucleic acid molecule in the second dose is between 0.3 and 0.4 mg/min;
(ii) the rate of administration of the lipid formulation in the first dose rate is between 1.0 and 1.5 mg/min, and the rate of administration of the lipid formulation in the second dose rate is between 3.5 and 4.5 mg/min; or
(iii) both (i) and (ii).

22. The method of claim 1, wherein:
(i) the amount of the nucleic acid molecule in the first dose is between 1.5 and 2.0 mg and the amount of the nucleic acid molecule in the second dose is between 15 and 25 mg;
(ii) the amount of the lipid formulation administered in the first dose is between 15 and 25 mg, and the amount of the lipid formulation administered in the second dose is between 200 and 300 mg; or
(iii) both (i) and (ii).

23. The method of claim 1, wherein the first dose is administered over a time period that is between 20% and 35% of the time period of administration of the second dose.

24. The method of claim 1, wherein the rate of administration of said first dose is about 20% to about 40% of the rate of administration of said second dose.

25. The method of claim 1, wherein:
(i) the first dose is administered at 1 mL/min, and the second dose is administered at between 3 mL/min;
(ii) the first dose is administered over a period of 15 minutes, and the second dose is administered over a period of 50 and 65 minutes; or
(iii) both (i) and (ii).

26. The method of claim 1, wherein one, two, or all of a)-c) of the following conditions is met:
a) the amount of said composition administered in said first dose is no more than 1/10 of the total amount of said composition administered;
b) the amount of said composition administered in said first dose is no more than 30 or 40 nucleic acids per kg body weight; or
c) the amount of said composition administered in said second dose is greater than 100 or 200 µg nucleic acids per kg body weight, and the second dose is greater than said first dose.

27. The method of claim 2, wherein one, two, or all of a)-c) of the following conditions is met:
a) the amount of said composition administered in said first dose is no more than 1/10 of the total amount of said composition administered;
b) the amount of said composition administered in said first dose is no more than 30 or 40 µg nucleic acids per kg body weight; or
c) the amount of said composition administered in said second dose is greater than 100 or 200 µg nucleic acids per kg body weight, and the second dose is greater than said first dose.

28. A method of reducing an infusion-related response (IRR), or a hypersensitivity reaction, or both, in a subject, to a composition comprising a lipid formulation and a nucleic acid molecule, said method comprising administering to a subject:
a first dose of said composition;
a second dose of said composition;
wherein the amount of said composition administered in said first dose is between 8% and 12% of the amount of said composition administered in said second dose;
wherein the first dose is administered over a time period that is no more than ½ of the time period over which the second dose is administered; and
wherein the rate of administration of said first dose is no more than ½ of the rate of administration of said second dose.

29. The method of claim 28, wherein one, two, three, four, or all of a)-e) of the following conditions is met:
a) the amount of said composition administered in said first dose is no more than ⅕ or 1/10 of the total amount of said composition administered;
b) the first dose is administered over a time period that is no more than ⅓ or ¼ of the time period over which the second dose is administered;
c) the rate of administration of said first dose is no more than ⅓ of the rate of administration of said second dose;
d) the amount of said composition administered in said first dose is no more than 30 or 40 µg nucleic acids per kg body weight
e) the amount of said composition administered in said second dose is greater than 100 or 200 µg nucleic acids per kg body weight.

30. The method of claim 1, wherein the nucleic acid molecule comprises a double stranded RNA (dsRNA).

31. The method of claim 1, wherein the nucleic acid molecule comprises a single-stranded RNA molecule.

32. The method of claim 1, wherein molecule the nucleic acid molecule comprises a sequence complementary to a target mRNA, wherein the target mRNA is chosen from an mRNA of: Factor VII, Eg5, PCSK9, TPX2, apoB, SAA, TTR, RSV, PDGF beta, Erb-B, Src, CRK, GRB2, RAS, MEKK, JNK, RAF, Erkl/2, PCNA(p21), MYB, JUN, FOS, BCL-2, HAMP, Activated Protein C, Cyclin D, VEGF, antithrombin 3, aminolevulinate synthase 1, alpha-1-antitrypsin, tmprss6, apoal, apoc3, bcl la, klf, angptl3, plk, PKN3, HBV, HCV, p53, angiopoietin, angiopoietin-like 3, complement component 3 (C3), or complement component 5 (C5).

33. The method of claim 2, wherein the nucleic acid molecule comprises a double stranded RNA (dsRNA).

34. The method of claim 2, wherein the target gene is chosen from a gene of: Factor VII, Eg5, PCSK9, TPX2, apoB, SAA, TTR, RSV, PDGF beta, Erb-B, Src, CRK, GRB2, RAS, MEKK, JNK, RAF, Erkl/2, PCNA(p21), MYB, JUN, FOS, BCL-2, HAMP, Activated Protein C, Cyclin D, VEGF, antithrombin 3, aminolevulinate synthase 1, alpha-1-antitrypsin, tmprss6, apoal, apoc3, bcl la, klf, angptl3, plk, PKN3, HBV, HCV, p53, angiopoietin, angiopoietin-like 3, complement component 3 (C3), or complement component 5 (C5).

35. The method of claim 1, wherein the non-cationic lipid is selected from the group consisting of distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, DOPE, POPC, EPC, ESM, polyethylene glycol-based polymers, and combinations thereof;
wherein the non-cationic lipid comprises from about 5 mol % to about 90 mol %, about 10 mol %, or about 58 mol % if cholesterol is included, of the total lipid present in the formulation.

36. The method of claim 1, wherein the PEG-lipid conjugate is a PEG-diacylglycerol (DAG), a PEG-dialkyloxypropyl (DAA), a PEG-phospholipid, a PEG-ceramide (Cer), or a mixture thereof.

37. The method of claim 1, wherein the lipid formulation comprises (6Z,9Z,28Z,31Z)-heptatriaconta-6,9,28,31-tetraen-19-y 14-(dimethylamino) butanoate (DLin-M-C3-DMA, MC3, or M-C3).

38. The method of claim 1, wherein the lipid formulation comprises about 50% of cationic lipid of Formula I/MC3, about 10% of a neutral lipid, about 38.5% of a sterol, and about 1.5% of PEG or a PEG-modified lipid.

39. The method of claim 1, wherein the lipid formulation comprises about 50% of cationic lipid of Formula I/MC3, about 10% of DSPC, about 38.5% of cholesterol, and about 1.5% of PEG-DMG.

40. The method of claim 2, wherein the nucleic acid molecule comprises a single stranded RNA molecule.

* * * * *

SEQUENCE LISTING

```
<160> NUMBER OF SEQ ID NOS: 6

<210> SEQ ID NO 1
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 1

Ala Ala Val Ala Leu Leu Pro Ala Val Leu Leu Ala Leu Leu Ala Pro
1               5                   10                  15

<210> SEQ ID NO 2
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 2

Ala Ala Leu Leu Pro Val Leu Leu Ala Ala Pro
1               5                   10
```

```
<210> SEQ ID NO 3
<211> LENGTH: 13
<212> TYPE: PRT
<213> ORGANISM: Human immunodeficiency virus

<400> SEQUENCE: 3

Gly Arg Lys Lys Arg Arg Gln Arg Arg Arg Pro Pro Gln
1               5                   10

<210> SEQ ID NO 4
<211> LENGTH: 16
<212> TYPE: PRT
<213> ORGANISM: Drosophila Antennapedia

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
gccuggaguu uauucggaat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
uuccgaauaa acuccaggct t                                              21
```